US012090204B2

(12) United States Patent
Kutschera et al.

(10) Patent No.: US 12,090,204 B2
(45) Date of Patent: Sep. 17, 2024

(54) PHOTODYNAMIC THERAPY COMPOSITIONS AND METHODS OF USE THEREOF

(71) Applicant: Pinnacle Biologics, Inc., Bannockburn, IL (US)

(72) Inventors: Glenn M. Kutschera, Bannockburn, IL (US); Thomas S. Mang, Bannockburn, IL (US)

(73) Assignee: Pinnacle Biologics, Inc., Bannockburn, IL (US)

( * ) Notice: Subject to any disclaimer, the term of this patent is extended or adjusted under 35 U.S.C. 154(b) by 0 days.

(21) Appl. No.: 17/471,777

(22) Filed: Sep. 10, 2021

(65) Prior Publication Data

US 2023/0047854 A1 Feb. 16, 2023
US 2023/0355768 A9 Nov. 9, 2023

Related U.S. Application Data

(60) Provisional application No. 63/223,835, filed on Jul. 20, 2021, provisional application No. 63/077,113, filed on Sep. 11, 2020.

(51) Int. Cl.
| | | |
|---|---|---|
| *A61K 41/00* | (2020.01) | |
| *A61K 9/00* | (2006.01) | |
| *A61K 9/06* | (2006.01) | |
| *A61K 47/02* | (2006.01) | |
| *A61K 47/20* | (2006.01) | |
| *A61P 31/04* | (2006.01) | |
| *A61P 31/10* | (2006.01) | |
| *A61P 31/16* | (2006.01) | |

(52) U.S. Cl.
CPC ........ *A61K 41/0071* (2013.01); *A61K 9/0014* (2013.01); *A61K 9/06* (2013.01); *A61K 47/02* (2013.01); *A61K 47/20* (2013.01); *A61P 31/04* (2018.01); *A61P 31/10* (2018.01); *A61P 31/16* (2018.01)

(58) Field of Classification Search
CPC .......... A61P 31/04; A61P 31/10; A61P 31/16; A61K 47/02; A61K 47/20; A61K 41/0071
See application file for complete search history.

(56) References Cited

U.S. PATENT DOCUMENTS

| | | | |
|---|---|---|---|
| 4,753,958 | A | 6/1988 | Weinstein et al. |
| 5,863,560 | A | 1/1999 | Osborne |
| 6,231,593 | B1 | 5/2001 | Meserol |
| 8,450,359 | B2 | 5/2013 | McCoy et al. |
| 2006/0265028 | A1 | 11/2006 | Houle et al. |
| 2008/0255498 | A1 | 10/2008 | Houle |
| 2008/0260697 | A1 | 10/2008 | Murthy et al. |
| 2009/0191254 | A1 | 7/2009 | Curtin et al. |
| 2022/0354953 | A1 | 11/2022 | Kutschera |

FOREIGN PATENT DOCUMENTS

| | | | |
|---|---|---|---|
| WO | WO2003039597 | A1 * | 5/2003 |
| WO | WO-2020084199 | A1 | 4/2020 |

OTHER PUBLICATIONS

Chang; Plast. Reconstr. Surg. 2005, 115, 1877-1886. doi: 10.1097/01.PRS.0000164684.69899.7B (Year: 2005).*
Triesscheijn; Oncologist 2006, 11, 1034-1044. https://doi.org/10.1634/theoncologist.11-9-1034 (Year: 2006).*
Photofrin (porfimer sodium) Prescribing Information, 13 pages, Apr. 2011. (Year: 2011).*
National Center for Biotechnology Information. "PubChem Compound Summary for Porfimer Sodium" PubChem, https://pubchem.ncbi.nlm.nih.gov/compound/Porfimer-Sodium. Accessed Sep. 15, 2023. (Year: 2023).*
Bernstein et al, "Combination of subatmospheric pressure dressing and gravity feed antibiotic instillation in the treatment of post-surgical diabetic foot wounds: A case series," Wounds 17(2):37-48 (2005).
Bodian, CA et al., "The Visual Analog Scale for Pain: Clinical Significance in Postoperative Patients," Anesthesiology 95:1356-1361 (2001).
Huang et al., Potassium Iodide Potentiates Broad-Spectrum Antimicrobial Photodynamic Inactivation Using Photofrin, ACS Infection Disease 3(4):320-328 (2017).
International Search Report and Written Opinion issued by the International Searching Authority for Application No. PCT/US2021049928, dated Feb. 16, 2022, 13 pages.
International Preliminary Report on Patentability issued by the International Searching Authority for Application No. PCT/US2021049928, dated Mar. 23, 2023, 10 pages.
International Search Report and Written Opinion for International Application No. PCT/US2022/037734, mailed Oct. 12, 2022, 6 pages.
Invitation to Pay issued by the International Searching Authority for Application No. PCT/US2021049928, dated Nov. 24, 2021, 2 pages.
Johnson, AP et al., "Dominance of EMRSA-15 and -16 among MRSA causing nosocomial bacteraemia in the UK: analysis of isolates from the European Antimicrobial Resistance Surveillance System (EARSS)," J. Antimicrobial Chemotherapy 48(1):141-156 (2001).
Lubrizol Technical Data Sheet, "Molecular Weight of Carbopol and Pemulen Polymers", dated Oct. 5, 2007, 3 pages; retrieved on Sep. 13, 2022 from https://www.lubrizol.com// media/Lubrizol/Health/TDS/TDS-222_Molecular_Weight_Carbopol_-Polymers.pdf.
Lui., et al., "Photodynamic Therapy in Dermatology," Archives of Dermatology, Dec. 1992, vol. 128, pp. 1631-1636.
Mordenti, J. et al., "The Use of Interspecies Scaling in Toxicokinetics," Toxicokinetics and New Drug Development, Yacobi et al., Eds., Pergamon Press, New York 42-96 (1989).
Ogura, M., et al., "Transdermal Delivery of Photosensitizer by the laser-Induced Stress Wave in 1-9, 26-35 Combination with Skin Heating," Japanese Journal of Applied Physics, Jul. 1, 2002, vol. 41, pp. L814-L816.
Wikipedia, "Porfimer sodium", 56,Jan. 23, 2021 (Jan. 23, 2021), 4 pages; retrieved on Sep. 13, 2022, from https://en.wikipedia.org/w/index.php?title=Porfimer_sodium&oldid=1002215081.

(Continued)

*Primary Examiner* — Daniel R Carcanague
(74) *Attorney, Agent, or Firm* — Cooley LLP

(57) ABSTRACT

A composition and method directed to the treatment of bacterial infections is provided.

18 Claims, 20 Drawing Sheets

(56) References Cited

OTHER PUBLICATIONS

Wolcott RD, et al., "Biofilm maturity studies indicate sharp debridement opens a time-dependent therapeutic window," J Wound Care 19:320-328 (2010).

Kaw et al., "A regimen to minimize pain during blue light photodynamic therapy of actinic keratoses: Bilaterally controlled, randomized trial of simultaneous versus conventional illumination," J Am Acad Dermatol 82(4):862-868 (2020).

PennMedicine, MRSA Infections (methicillin-resistant *Staphylococcus aureus*), 5 pages, [retrieved on Jan. 11, 2024]. Retrieved from the internet:https://www.pennmedicine.org/for-patients-and-visitors/patient-information/conditions-treated-a-to-z/ mrsa-methicillin-resistant-staphylococcus-aureus (Year: 2020).

\* cited by examiner

PHOTODYNAMIC THERAPY COMPOSITIONS AND METHODS OF USE THEREOF

CROSS-REFERENCE TO RELATED APPLICATIONS

This application claims priority to U.S. Provisional Application No. 63/077,113, filed Sep. 11, 2020, and U.S. Provisional Application No. 63/223,835, filed Jul. 20, 2021, the disclosures of which are herein incorporated by reference in their entirety for all purposes.

BACKGROUND OF THE INVENTION

Bacterial infections, especially those involving biofilms, are increasingly challenging to treat specifically due to antibiotic resistance. This poses challenging clinical problems particularly with skin and soft tissue infections (SSTI's), both uncomplicated skin and soft tissue infections (uSSTI's) and complicated skin and soft tissue infections (SSTIs), often referred to as acute bacterial skin and skin structure infections (ABSSSI). SSTIs are defined as infections of the epidermis, dermis or subcutaneous tissue. Prime examples can be demonstrated in mupirocin-resistant *S. aureus* (mupRSA) and methicillin-resistant *Staphylococcus aureus* (MRSA) infections. Antibiotic resistance is reaching critical stages worldwide. Given the magnitude of this problem and the overall results on morbidity and mortality, multidrug resistant organisms are a significant threat to public healthcare globally. While the need to develop new antimicrobials is essential, recent history has established that simply using this approach creates greater resistance rather than bring about elimination, of selective resistance. Further complicating the management of soft tissue infections is the paradox that bacterial isolates that might be susceptible to an antibacterial therapy in vitro does not necessarily predict susceptibility in an in vivo model or live subject where pharmacokinetic and pharmacodynamic factors can significantly alter antimicrobial activity.

While there is clearly a need for novel therapeutics, the development of new and effective antibiotics is both costly and time consuming and history has shown that this approach will not successfully lead to effective control nor elimination of resistance.

Photodynamic therapy (PDT) combines the use of non-toxic photosensitizers (PS) and low intensity visible non-thermal light that results in the production of cytotoxic species in the presence of oxygen. PDT has long been approved for use in the treatment of certain malignancies and other diseases in the United States (US) as well in many other countries. Early studies led to the development of porfimer sodium (Photofrin®, Concordia Laboratories Inc.), the first FDA approved PS for clinical use in the US. Since the development of this therapy, there have been numerous proposed and evaluated uses of PDT. While the combination of dyes and light activation has been applied to bacteria, viruses and fungi in vitro, there is currently no approved for use for treating microbial infections with this technology in the US, as such technology has been difficult to reproduce in vivo.

The formation of biofilm by pathogens is a critical factor in establishing persistent colonization in chronic disease and wound infection. Microbial biofilms are inherently resistant (10-100×) to most antibiotic regimens as well as possessing defense systems to host immunity. Biofilms are composed of microbial cells and extracellular polymeric substance matrix (EPS) which can account for a high percentage of the total organic material in the biofilm. Previous in vitro work has also focused on the evaluation of antimicrobial PDT (aPDT) on biofilm of various pathogens. Any such in vitro work with the combination of dyes and light activation when applied to "microbial biofilms has also been difficult to effectively reproduce in vivo.

Accordingly, there remains a need to develop compositions and methods of use thereof for effective photodynamic treatment of pathogens.

SUMMARY OF THE INVENTION

In one aspect, the present disclosure provides pharmaceutical compositions comprising a photosensitizer and one or more gelling agents.

In some embodiments the present disclosure provides pharmaceutical topical formulations comprising porfimer sodium and one or more pharmaceutical acceptable excipients.

In some embodiments, the present disclosure provides methods for treating an infected area such as a wound, comprising administering to a subject in need thereof any pharmaceutical composition or formulation of the present disclosure, wherein the composition is applied to the infected area; and light is applied to the infected area.

In some embodiments, the present disclosure provides methods for treating a microbial infection, comprising administering to a subject in need thereof a therapeutically effective amount of a composition a formulation from any one of claims herein, wherein the composition or formulation is applied to the infection; and light is applied to the infected area.

DETAILED DESCRIPTION

Figure 1A:
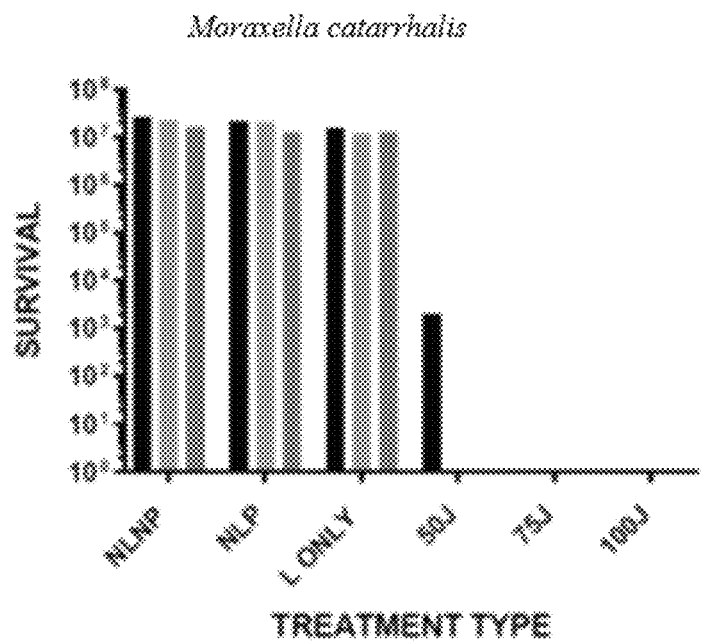
FIG. 1A shows the bactericidal effects of porfimer sodium aPDT on planktonic cultures of gram negative *M. catarrhalis*. NLNP corresponds to no laser, no porfimer. NLP corresponds to no laser but with porfimer solution. L only corresponds to laser only at highest dose. Light doses are in joules/cm$^2$. Power density was 150 mW/cm$^2$.

In one aspect, the present disclosure provides compositions and methods for the photodynamic treatment of infected areas. It has surprisingly been found that certain compositions are able to effectively treat difficult infections, such as MRSA. This is supported by in vivo animal trials, where conventional compositions failed.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988), The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the verb "comprise" as is used in this description and in the claims and its conjugations are used in its non-limiting sense to mean that items following the word are included, but items not specifically mentioned are not excluded. The present disclosure may suitably "comprise", "consist of", or "consist essentially of", the steps, elements, and/or reagents described in the claims.

Unless specifically stated or obvious from context, as used herein, the term "or" is understood to be inclusive. Unless specifically stated or obvious from context, as used herein, the terms "a", "an", and "the" are understood to be singular or plural.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

As disclosed herein, "photodynamic therapy" or "PDT" or antimicrobial photodynamic therapy (aPDT) involves the use of a chemical photosensitizer or a nontoxic photoactivatable dye, visible non-thermal light, and reactive oxygen. The therapy is based on the energy (absorbed as light via the photosensitizer) transferred to the oxygen molecules producing extremely reactive mediation, such as singlet oxygen and superoxide, that are noxious to the cells. Photodynamic therapy requires a light source for triggering the photosensitizer with a low power visible light at a particular wavelength. Most of the optical photosensitizers are actuated by light of 380 nm to 850 nm wavelengths corresponding to a light permeation depth of 0.2 cm to 1.5 cm.

As disclosed herein, PDT uses "photosensitizers" or "PS" that are activated by absorption of visible light to initially form the excited singlet state, followed by transition to the long-lived excited triplet state. This triplet state can undergo photochemical reactions in the presence of oxygen to form reactive oxygen species (including singlet oxygen) that can destroy pathogenic microbes. The dual-specificity of PDT relies on accumulation of the PS in infected tissue and also on localized light delivery. As disclosed herein, PSs can include but are not limited to porphyrin based photosensitizers and tetrapyrrole structures such as porphyrins, chlorins (HPPH; NPe6; Temoporfrin (Foscan), mTHPC)), and porphysomes as in: pyropheophorbide nanovesicles including, bacteriochlorophyll porphysomes, zinc pyropheophorbide porphysomes and pyrophcophyorbide porphysomes, and chlorin-like compounds (benzoporphyrin; Verteporfin, bacteriochlorins and phthalocyanines, purpurins (tin ethyl etiopurpurin); Metalloporphyrins (Texaphyrins); Pheophorbides (TOOKAD); Protoporphyrins (Levulan, Metvix, 5-ALA (PpIX)) and nonporphyrin based photosensitizers including phenothiazinium salts such as Methylene Blue, Toluidine Blue, Nile Blue, Cyanines, hypericin and Chalcogenpyrilium dyes; PPA904; benzophenothiazinium dye EtNBS; PS can also include the xanthene class of fluorescent dyes that includes fluorescein and Rose Bengal; Fullerenes (C60 fullerene coupled to polar diserinol groups or quarternary pyrrolidinium groups) Also Squaraogenines, BODIPY (boron-dipyrromethene) dye, Phenalenones; Hypericin, Hypocrellin, Riboflavin, Curcumin, Titanium dioxide. As used herein, the preferred PS is porfimer sodium (Photofrin®).

As disclosed herein, "potentiator of PDT" refers to for example, potassium iodide (KI) which has a potentiating effect on PDT. Addition of KI to a mixture of microbial cells and a PS that is subsequently excited by light can give many log units of additional killing. Addition of KI to porfimer sodium allows broad-spectrum PDT, including the eradication of Gram-negative bacteria. As disclosed herein, a potentiator of PDT can include inorganic salts, such as sodium azide, sodium thiocyanate, sodium bromide and potassium iodide, sodium and iodide, and potassium selenocyanate (KSeCN). In some embodiments, the potentiator of PDT is potassium iodide (KI).

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "managing" includes therapeutic treatments as defined above. Managing includes achieving a steady state level of infection as determined by known methods in the art. The steady state can include evaluation of one or more of the severity of the infection(s), the size and location of the infection(s), the number of different microbial pathogens present in the infection(s), the level of antibiotic tolerant or resistant microbial pathogens, the degree of response to treatment, such as with a PS composition disclosed herein, the degree of biofilm formation and reduction, and the side effects experienced by the subject. During management of an infection, the infection may fluctuate from increasing to lessening in severity, in the amount or extent of infection, amount of side effects experienced by the subject, or other subject outcome indicia. Over a period of time, such as days, months, or years, the degree of management of the infection can be determined by evaluation of the above factors to assess whether the clinical course of infection has improved, is bacteriostatic, or has worsened. In some embodiments, managing an infection include successful treatment of microbial pathogen(s) that are otherwise drug tolerant or drug resistant.

The term "lessen the severity" of infection(s) refers to an improvement in the clinical course of the infection on any measurable basis. Such basis can include measurable indices such as reducing the extent of infection(s), whether the infection(s) are considered acute, the number and identity of microbial pathogens causing the infection(s), the extent/spread/amount of microbial (e.g. bacterial and/or fungal) biofilms, and side effects experienced by the subject. In some embodiments, lessening the severity of an infection is determined by measuring an improvement in clinical signs and symptoms of infection. In some embodiments, lessening the severity involves halting a steady decline in outcome to achieve stabilized infection(s), resulting in the subject entering successful management of the infection(s). In other embodiments, lessening the severity can result in substantial to complete treatment of the infection(s).

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of an infection.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

A "response" to a method of treatment can include, among other things, a decrease in or amelioration of negative signs and symptoms, a decrease in the progression of an infection or symptoms thereof, an increase in beneficial symptoms or clinical outcomes, a lessening of side effects, stabilization of the infection, and partial or complete remedy of infection, partial or full wound closure, reduction in wound size, or complete or substantially complete re-epithelialization, among others.

"Antibiotic susceptibility or sensitivity" refers to whether a bacteria will be successfully treated by a given antibiotic. Similarly, "Antifungal susceptibility or sensitivity" refers to whether a fungi will be successfully treated by a given antibiotic. Testing for susceptibility can be performed by methods known in the art such as the Kirby-Bauer method, the Stokes method and Agar Broth dilution methods. The effectiveness of an antibiotic in killing the bacteria or preventing bacteria from multiplying can be observed as areas of reduced or stable amount, respectively, of bacterial growth on a medium such as a wafer, agar, or broth culture.

"Antimicrobial resistance" refers to the ability of a microbe to resist the effects of medication that once could successfully treat the microbe. Microbes resistant to multiple antimicrobials are called multidrug resistant (MDR). Resistance arises through one of three mechanisms: natural resistance in certain types of bacteria, genetic mutation, or by one species acquiring resistance from another. Mutations can lead to drug inactivation, alteration of the drug's binding site, alteration of metabolic pathways and decreasing drug permeability.

As used herein, the terms "prophylactic agent" and "prophylactic agents" refer to an agent, such as a PS composition of the present disclosure, which can be used in the prevention, management, or control of one or more signs and symptoms of an infected area, including a disease or disorder, in particular, disease or disorder associated with a microbial (e.g. bacterial and/or fungal) infection such as a SSTI and wound infections not limited to but including sacrococcygeal pilonidal sinus disease, sinusitis, soft tissue infections following marine injuries, onychomycosis and infections of the skin and soft tissues by opportunistic human pathogens.

As used herein, the terms "antibacterial activity", "antifungal activity" and "antimicrobial activity", with reference to a PS composition of the present disclosure, refers to the ability to kill and/or inhibit the growth or reproduction of a particular microorganism. In certain embodiments, antibacterial or antimicrobial activity is assessed by culturing bacteria, e.g., Gram-positive bacteria (e.g., *S. aureus*). Gram-negative bacteria (e.g., *Moraxella catarrhalis*) or atypical bacteria not classified as either Gram-positive or Gram-negative, or fungi (e.g., *C. albicans*) according to standard techniques (e.g., in liquid culture or on agar plates), contacting the culture with a PS composition of the present disclosure and monitoring cell growth after said contacting. For example, in a liquid culture, bacteria may be grown to an optical density ("OD") representative of a mid-point in exponential growth of the culture, the culture is exposed to one or more concentrations of one or more PS compounds of the present disclosure, or variants thereof, and the OD is monitored relative to a control culture. Decreased OD relative to a control culture is representative of antibacterial activity (e.g., exhibits lytic killing activity). Similarly, bacterial colonies can be allowed to form on an agar plate, the plate exposed to a PS composition of the present disclosure, or variants thereof, and subsequent growth of the colonies evaluated related to control plates. Decreased size of colonies, or decreased total numbers of colonies, indicate antibacterial activity.

"Biofilm" refers any syntrophic consortium of microorganisms in which cells stick to each other and often also to a surface. These adherent cells become embedded within a slimy extracellular matrix that is composed of extracellular polymeric substances (EPS). Upon formation of biofilms, microbial resistance to antibiotics is up to 1000 times greater compared to that of planktonic bacteria. Bacterial aggregates are clusters of laterally aligned cells can initiate biofilm development, which has a more complex and denser 3-D structure. In some embodiments, the biofilm may comprise one or more species of bacteria (e.g., *Moraxella catarrhalis* and *Staphylococcus aureus*) and/or one or more different phyla (e.g., bacteria and fungi).

The term "infection" is used herein in its broadest sense and refers to any infection, such as caused by a microorganism bacterial infection or fungal infection. Examples of such infections can be found in a number of well-known texts such as "Medical Microbiology" (Greenwood, D., Slack, R., Peutherer, J., Churchill Livingstone Press, 2002); "Mims' Pathogenesis of Infectious Disease" (Minis, C., Nash, A., Stephen, J., Academic Press, 2000); "Fields" Virology. (Fields, B N, Knipe D M, Howley, P M, Lippincott Williams and Wilkins, 2001); and "The Sanford Guide To Antimicrobial Therapy," 26th Edition, JP Sanford et al. (Antimicrobial Therapy, Inc. 1996), which is incorporated by reference herein.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of other active agents" would either completely lack other active agents, or so nearly completely lack other active agents that the effect would be the same as if it completely lacked other active agents. In other words, a composition that is "substantially free of an ingredient or element or another active agent may still contain such an item as long as there is no measurable effect thereof.

As used herein, "weight for weight" or "weight by weight" or "w/w", refers to the proportion of a particular substance within a mixture, as measured by weight or mass. "% wt" as used herein refers to the percent of the total weight of the composition.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The present invention relates to compositions, including pharmaceutical compositions, comprising a photosensitizer and one or more pharmaceutically acceptable excipients, and methods related to administering said compositions to a subject for treating a microbial infection.

Pharmaceutical Compositions

In some embodiments, the present disclosure provides a pharmaceutical composition comprising a photosensitizer, one or more gelling agents, and one or more pharmaceutically acceptable excipients or carriers. In some embodiments of the pharmaceutical compositions disclosed herein, the pharmaceutical composition comprises a photosensitizer, a gelling agent, one or more permeation enhancers, a humectant, a stabilizer, a solubilizer, and/or a preservative. In some embodiments, the pharmaceutical composition may also include one or more solvents, buffers, bodifying agents, antioxidants, stabilizers and surfactants. In another embodiments, the pharmaceutical composition comprises one or more photosensitizer, a gelling agent, one or more permeation enhancers, a humectant, a solubilizer, a preservative and/or a potentiator.

In another embodiment, the present disclosure provides a pharmaceutical composition comprising a photosensitizer one or more gelling agents, and one or more pharmaceutically acceptable excipients or carriers. In some embodiments of the pharmaceutical compositions disclosed herein, the pharmaceutical composition comprises a photosensitizer, a gelling agent, one or more permeation enhancers, a humectant, a stabilizer, a solubilizer, and/or a preservative.

In some embodiments, the pharmaceutical composition may also include one or more solvents, buffers, bodifying agents, antioxidants, and surfactants.

In some embodiments of the pharmaceutical compositions disclosed herein, the photosensitizer is selected from one or more of the group consisting of porphyrin based photosensitizers and tetrapyrrole structures such as porphyrins, chlorins (HPPH; NPe6; Temoporfrin (Foscan), mTHPC)), and porphysomes as in: pyropheophorbide nanovesicles including, bacteriochlorophyll porphysomes, zinc pyropheophorbide porphysomes and pyropheophyorbide porphysomes, and chlorin-like compounds (benzoporphyrin; Verteporfin, bacteriochlorins and phthalocyanines, purpurins (tin ethyl etiopurpurin); Metalloporphyrins (Texaphyrins); Pheophorbides (TOOKAD); Protoporphyrins (Levulan, Metvix, 5-ALA (PpIX)) and nonporphyrin based photosensitizers including phenothiazinium salts such as Methylene Blue, Toluidine Blue, Nile Blue, Cyanines, hypericin and Chalcogenpyrilium dyes; PPA904; benzophenothiazinium dye EtNBS; PS can also include the xanthene class of fluorescent dyes that includes fluorescein and Rose Bengal; Fullerenes (C60 fullerene coupled to polar diserinol groups or quarternary pyrrolidinium groups) Also Squaraogenines, BODIPY (boron-dipyrromethene) dye, Phenalenones; Hypericin, Hypocrellin, Riboflavin, Curcumin, Titanium dioxide. As used herein, the preferred PS is porfimer sodium (Photofrin®).

In some embodiments of the pharmaceutical compositions disclosed herein, the porfimer sodium is in an amount ranging from about 0.01% wt to about 1.0% wt; or about 0.05% wt to about 0.7% wt; or about 0.1% wt to about 0.5% wt; or about 0.15% wt to about 0.3% wt. In some embodiments, the porfimer sodium is an amount ranging from 0.01% wt to 1.0% wt; or 0.05% wt to 0.7% wt; or 0.1% wt to 0.5% wt; or 0.15% wt to 0.3% wt. In some embodiments of the pharmaceutical compositions disclosed herein, the porfimer sodium is present in an amount ranging of from about 0.01% wt, about 0.02% wt, 0.03% wt, 0.04% wt, about 0.05% wt, about 0.06% wt, about 0.07% wt, about 0.08% wt, about 0.09% wt, about 0.1% wt, about 0.2% wt, about 0.3% wt, about 0.4% wt, about 0.5% wt, about 0.6% wt, about 0.7% wt, about 0.8% wt, about 0.9% wt to about 1.0% wt, including all values and subranges therebetween. In some embodiments, the porfimer sodium is in an amount ranging from about 0.01% wt to about 1.0% wt; or about 0.05% wt to about 0.7% wt; or about 0.1% wt to about 0.5% wt. In some embodiments, the porfimer sodium is an amount ranging from 0.01% wt to 1.0% wt; or 0.05% wt to 0.7% wt; or 0.1% wt to 0.5% wt. In some embodiments, the porfimer sodium is an amount ranging from about 0.05% wt to about 0.15% wt; or about 0.15% wt to 0.25% wt; or 0.4% wt to 0.6% wt.

Gelling agents may be added to the pharmaceutical compositions of the present invention. Gelling agents are any suitable substance that is used to modify the viscosity of the composition. For example, gelling agents may be highly crosslinked or otherwise possess strong intermolecular interactions to increase the cohesion of the composition. Various gelling agents can be employed including, for example and without limitation, sugars or sugar derived alcohols, such as mannitol, sorbitol, and the like, starch and starch derivatives, cellulose derivatives, such as microcrystalline cellulose, sodium cahoxymethyl cellulose, methylcellulose, ethyl cellulose, hydroxyethyl cellulose, hydroxypropyl cellulose, and hydroxypropyl methylcellulose, bentonites, attapulgites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof, etc. Examples of suitable gelling agents include hydroxy propyl cellulose, acrylic acids such as Carbopol 980, and lecithins such as Lecithin-PLO.

For topical application to the skin, the pharmaceutical compositions of the present disclosure may be combined with one or a combination of gelling agents for topical formulations, which can include, but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, carbomer polymers such as carbomer homopolymers, carbomer copolymers, including Carbopol® polymers, and combinations thereof. Carbopol® polymers are polymers of acrylic acid cross-linked e.g., with polyalkenyl ethers or divinyl glycol. In some embodiments, the Carbopol® polymer is Carbopol® 71G, Carbopol® 971P, Carbopol® 974P, Carbopol® 980, Carbopol® 981, Carbopol& 5984, Carbopol® 934, Carbopol® 934P, Carbopol® 940, Carbopol® 941, and Carbopol® 1342. The compositions of the present invention comprise semi-solid and gel-like vehicles that include a polymer thickener, water, preservatives, active surfactants or emulsifiers, antioxidants, and a solvent or mixed solvent system. The solvent or mixed solvent system is important to the formation of the microparticulate to dissolved pharmaceutical ratio. The formation of the microparticulate, however, should not interfere with the ability of the polymer thickener or preservative systems to perform their functions.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B. F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.).

In some embodiments of the pharmaceutical compositions disclosed herein, the gelling agent is selected from one or more of the group consisting of a, carbomer, crosslinked, polyacrylic acid, lecithin, hydroxyethyl cellulose, hydroxypropyl cellulose, and hydroxypropyl methylcellulose. In some embodiments, the gelling agent is a polymer of acrylic acid cross-linked with polyalkenyl ethers or divinyl glycol. In some embodiments, the gelling agent is a carbomer. In some embodiments, the carbomer is Carbopol® 71G, Carbopol® 971P, Carbopol® 974P, Carbopol® 980, Carbopol® 981, Carbopol® 5984, Carbopol® 934, Carbopol® 934P, Carbopol® 940, Carbopol® 941, and/or Carbopol® 1342.

In some embodiments of the pharmaceutical compositions disclosed herein, the gelling agent is in an amount ranging from about 0.5% wt to about 3.0% wt, or from about 0.7% wt to about 2.0% wt, or from about 1.0% wt to about 1.75% wt. In some embodiments, the gelling agent is in an amount ranging from 0.5% wt to 3.0% wt, or from 0.7% wt to 2.0% wt, or from 1.0% wt to 1.75% wt, or from 1.1% wt to 1.6% wt, or from 1.2% wt to 1.5% wt including all values and subranges therebetween. In some embodiments, the gelling agent is in an amount ranging from about 0.5% wt to about 3.0% wt, or from about 0.7% wt to about 2.0% wt, or from about 0.5% wt to about 1.5% wt. In some embodiments, the gelling agent is in an amount ranging from 0.5% wt to 3.0% wt, or from 0.7% wt to 2.0% wt, or from 0.5% wt to 1.5% wt.

In some embodiments, the pharmaceutical composition or pharmaceutical topical formulation further comprises one or more permeation enhancers.

As defined herein, a "permeation enhancer" is taken to mean any substance which acts as a skin penetrant and enhances the ability for the active agent to pass through the epidermal tissue into dermal tissue, or through dermal tissue. In some embodiments, the permeation enhancer may be one or more of an alcohol, amide, fatty acid, ester, ether alcohol, surfactant, phospholipid, pyrrolidone or a terpene. In a specific embodiment, the permeation enhancer may be one or more of ethanol, isopropyl alcohol, decanol, octanol, propylene glycol, polyethylene glycol, Azone® (1-dodecylazacycloheptan-2-one or laurocapram, lauric acid, oleic acid, linoleic acid, ethyl acetate, butyl acetate, methyl acetate, isopropyl myristate, isopropyl palmitate, transcutol such as diethylene glycol monoethyl ether, sodium lauryl sulphate, benzalkonium chloride, cetylpyridinium chloride, cetyltrimethylammonium bromide; polysorbates (Tween® 20, Tween® 80, etc.), dodecyl betaine, dimethyl sulphoxide (DMSO), decylmethyl sulphoxide (DCMS), D-Limonene, L-menthol, 1,8-Cineole, N-methyl-1-2-pyrrolidone (NMP), N-methyl-1-2-pyrrolidone (NMP), 2-pyrrolidone (2P), 4-decyloxazolidin-2-one, phosphatidylcholine, acid phosphatase, papain, and phospholipase C.

Permeation enhancer may have also act as solvents, or have solvating effects, may act as a surface surfactant enhancer, and/or act as an emulsifier. Permeation enhancers that may be used include those known to one skilled in the art, polyols and esters including, glycol esters (e.g., polyethylene glycol, polyethylene glycol monolaurate) and butanediol; sulfoxides, including dimethylsulfoxide and decylmethylsulfoxide; ethers, including diethylene glycol monoethyl ether (e.g., Transcutol® P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; azones, polysorbates, alcohols, and any mixtures thereof. Further, one or more surfactants can also be used as a permeation or permeation enhancer. In some embodiments, the permeation enhancer is selected from one or more of the group consisting of propylene glycol, polyethylene glycol of average molecular weight from 200 to 4000, diethylene glycol monoethyl ether, Transcutol P, Polysorbate 80, polyoxylglycerides, Labrasol®, diethyl sebacate, diisopropyl adipate, dimethyl isosorbide, dimethyl sulfoxide, ethanol, Tween 80, Laureth-4, butanediol, polyethylene glycol monolaurate, diethylene glycol monoethyl ether, dimethylsulfoxide, decylmethylsulfoxide, lauric acid, oleic acid, valeric acid, isopropyl myristate, isopropyl palmitate, methyl propionate, ethyl oleate, and oleic acid. Suitable examples of permeation enhancers include hexylene glycol, propylene glycol SR, polyethylene glycol 400 SR, polyethylene glycol 300 LA, diethylene glycol monoethyl ether, and Polysorbate 80 SR.

In some embodiments, the permeation enhancer is selected from one or more of the group consisting of DMSO, diethylene glycol monoethyl ether, propylene glycol, polyethylene glycol, and the various forms, molecular weights and grades therein. In a specific embodiment, the permeation enhancer is selected from one or more of the group consisting of propylene glycol SR, polyethylene glycol 400 SR, polyethylene glycol 300 LA, diethylene glycol monoethyl ether, and Polysorbate 80 SR. In some embodiments, the permeation enhancer is selected from one or more of the group consisting of propylene glycol SR, DMSO, and diethylene glycol monoethyl ether.

In some embodiments of the pharmaceutical compositions disclosed herein, the one or more permeation enhancers is in an amount ranging from about 0.5% wt to about 70% wt, or from about 1% wt to about 60% wt, or from about 10% wt to about 60% wt, or from about 5% wt to about 30% wt, or from about 15% wt to about 30% wt. In some embodiments, the gelling agent is in an amount ranging from 0.5% wt to 50% wt, or from 10% wt to 40% wt, or from 15% wt to 30% wt. In some embodiments of the compositions disclosed herein, the permeation enhancer is in an amount ranging from about 0.5% wt, about 1% wt, about 5% wt, about 10% wt, about 11% wt, about 12% wt, about 13% wt, about 14% wt, about 15% wt, about 16% wt, about 17% wt, about 18% wt, about 19% wt, about 20% wt, about 21% wt, about 22% wt, about 23% wt, about 24% wt, about 25% wt, about 26% wt, about 27% wt, about 28% wt, about 29% wt, about 30% wt, about 31% wt, about 32% wt, about 33% wt, about 34% wt, about 35% wt, about 36% wt, about 37% wt, about 38% wt, about 39% wt, about 40% wt, about 41% wt, about 42% wt, about 43% wt, about 44% wt, about 45% wt, about 46% wt, about 47% wt, about 48% wt, about 49% wt, about 50% wt, about 51% wt, about 52% wt, about 53% wt, about 54% wt, about 55% wt, about 56% wt, about 57% wt, about 58% wt, about 59% wt, about 60% wt, about 61% wt, about 62% wt, about 63% wt, about 64% wt, about 65% wt, about 66% wt, about 67% wt, about 68% wt, about 69% wt, about 70% wt, including all subranges therebetween.

In some embodiments of the pharmaceutical compositions disclosed herein, the solubilizer is in an amount ranging from 1.0% wt to about 5% wt, or about 1% to about 3%, or about 2%. In some embodiments, the solubilizer is in an amount of about 1.0% wt, or about 2% wt, or about 3% wt, or about 4% wt, or about 5% wt. In some embodiments, the permeation enhancer is in an amount ranging from about 1.0% wt to about 60% wt, or about 20% wt to about 40% wt.

In some embodiments, the compositions disclosed herein comprise a potentiator of PDT. In a specific embodiment, the potentiator of PDT may be one or more inorganic salts, such as sodium azide, sodium thiocyanate, sodium bromide, potassium iodide (KI), sodium iodide, and potassium selenocyanate (KSeCN). In a specific embodiment, the potentiator of PDT is potassium iodide (KI). In some embodiments of the pharmaceutical compositions disclosed herein, the concentration of the potentiator of PDT (e.g., KI) is in an amount ranging from about 0.1 mM to about 1 M. In some embodiments, the potentiator of PDT the potentiator of PDT (e.g., KI) is in an amount ranging from about 10 mM to about 100 mM. For example, in some embodiments, the potentiator of PDT (e.g., KI) is in an amount ranging from about 10 mM, or about 20 nM, or about 30 mM, or about 40 mM, or about 50 mM, or about 60 mM, or about 70 mM, or about 80 mM, or about 90 mM, or about 100 mM or about 110 nM, or about 120 mM, or about 130 mM, or about 140 mM, or about 150 mM, or about 160 mM, or about 170 mM, or about 180 mM, or about 190 mM, or about 200 mM, or about 210 mM, or about 220 nM, or about 230 mM, or about 240 mM, or about 250 mM, or about 260 mM, or about 270 mM, or about 280 mM, or about 290 mM, or about 300, or about 310 mM, or about 320 nM, or about 330 mM, or about 340 mM, or about 350 mM, or about 360 mM, or about 370 mM, or about 380 mM, or about 390 mM, or about 400 mM, or about 410 mM, or about 420 nM, or about 430 mM, or about 440 mM, or about 450 mM, or about 460 mM, or about 470 mM, or about 480 mM, or about 490 mM, to about 500 mM, including all sub-ranges and values therebetween. In some embodiments, the potentiator of PDT the potentiator of PDT (e.g., KI) is in an amount of about 100 mM. In a specific embodiment, the potentiator of PDT in the amounts or ranges herein is KI.

In some embodiments, the potentiator of PDT the potentiator of PDT (e.g., KI) is in an amount ranging from about 0.01% wt to about 5% wt. For example, in some embodiments, the potentiator of PDT (e.g., KI) is in an amount ranging from about 0.1% wt, about 0.2% wt, about 0.3% wt, about 0.4% wt, about 0.5% wt, about 0.6% wt, about 0.7% wt, about 0.8% wt, about 0.9% wt, about 1% wt, about 1.1% wt, about 1.2% wt, about 1.3% wt, about 1.4% wt, about 1.5% wt, about 1.6% wt, about 1.7% wt, about 1.8% wt, about 1.9% wt, about 2.0% wt, about 2.1% wt, about 2.2% wt, about 2.3% wt, about 2.4% wt, about 2.5% wt, about 2.6% wt, about 2.7% wt, about 2.8% wt, about 2.9% wt, about 3.0% wt, about 3.1% wt, about 3.2% wt, about 3.3% wt, about 3.4% wt, about 3.5% wt, about 3.6% wt, about 3.7% wt, about 3.8% wt, about 3.9% wt, about 4.0% wt, about 4.2% wt, about 4.4% wt, about 4.6% wt, about 4.8% wt, about 5.0% wt, about 5.5% wt, about 6.0% wt, about 6.5% wt, about 7.0% wt, about 7.5% wt, about 8.0% wt, about 8.5% wt, about 9.0% wt, about 9.5% wt, about 10.0% wt, about 10.5% wt, about 11.0% wt, about 11.5% wt, about 12.0% wt, about 12.5% wt, about 13.0% wt, about 13.5% wt, about 14.0% wt, about 14.5% wt, to about 15.0% wt, including all sub-ranges and values therebetween. In some embodiments, the potentiator of PDT (e.g., KI) is in an amount ranging from about 0.5% wt to about 5% wt, or from about 1% wt to about 2% wt. In some embodiments, the potentiator of PDT (e.g., KI) is in an amount ranging from about 0.1% wt to about 2% wt, or from about 0.2% wt to about 1% wt. In a specific embodiment, the potentiator of PDT in the amounts or ranges herein is KI.

In some embodiments of the pharmaceutical compositions disclosed herein, the potentiator of PDT is selected from the group consisting of sodium azide, sodium thiocyanate, sodium bromide, potassium iodide, and sodium iodide. In some embodiments, the potentiator of PDT is potassium iodide (KI).

In some embodiments, the pharmaceutical composition or pharmaceutical topical formulation further comprises one or more surfactants. In some embodiments, the surfactant is a polysorbate, such as Polysorbate 80. Furthermore, other surfactants may be used instead of Polysorbate 80; for example sulfates such as sodium lauryl sulfate, and the related alkyl-ether sulfates sodium lauryl ether sulfate, and sodium myreth sulfate; polyethylene glycol, the fraction size of polyethylene glycol may be varied. Other suitable surfactants include alkyl-aryl ether phosphates, alkyl ether phosphates, and carboxylates, such as sodium stearate, or non-ionic surfactants such as ethoxylates, fatty acid esters of polyhydroxy compounds, fatty acid esters of sorbitol, fatty acid esters of sucrose, and alkyl polyglucosides.

In some embodiments of the pharmaceutical compositions disclosed herein, the surfactant is in an amount ranging from 0.01% wt to about 5% wt, including about 0.01%, about 0.05%, about 0.1% wt, about 0.2% wt, about 0.3% wt, about 0.4% wt, about 0.5% wt, about 0.6% wt, about 0.7% wt, about 0.8% wt, about 0.9% wt, about 1% wt, about 1.1% wt, about 1.2% wt, about 1.3% wt, about 1.4% wt, about 1.5% wt, about 1.6% wt, about 1.7% wt, about 1.8% wt, about 1.9% wt, about 2.0% wt, about 2.1% wt, about 2.2% wt, about 2.3% wt, about 2.4% wt, about 2.5% wt, about 2.6% wt, about 2.7% wt, about 2.8% wt, about 2.9% wt, about 3.0% wt, about 3.1% wt, about 3.2% wt, about 3.3% wt, about 3.4% wt, about 3.5% wt, about 3.6% wt, about 3.7% wt, about 3.8% wt, about 3.9% wt, about 4.0% wt, about 4.2% wt, about 4.4% wt, about 4.6% wt, about 4.8% wt, to about 5.0% wt, including all sub-ranges and values therebetween. In some embodiments, the solvent is in an amount ranging from about 0.5% wt to about 1.5% wt, or about 1% wt.

In some embodiments, the pharmaceutical composition or pharmaceutical topical formulation further comprises one or more solvents. Among the acceptable solvents that may be employed are water, Ringer's solution and isotonic sodium chloride solution. In addition, non-aqueous solvents may be employed. Examples of non-aqueous solvents suitable for use in the present application include, but are not limited to, propylene glycol, hexylene glycol, polyethylene glycol, vegetable oils such as olive oil, and injectable organic esters such as ethyl oleate. In some embodiments, the solvent is hexylene glycol.

In some embodiments of the pharmaceutical compositions disclosed herein, the solvent is in an amount ranging from 0.01% wt to about 5% wt, including about 0.01%, about 0.05%, about 0.1% wt, about 0.2% wt, about 0.3% wt, about 0.4% wt, about 0.5% wt, about 0.6% wt, about 0.7% wt, about 0.8% wt, about 0.9% wt, about 1% wt, about 1.1% wt, about 1.2% wt, about 1.3% wt, about 1.4% wt, about 1.5% wt, about 1.6% wt, about 1.7% wt, about 1.8% wt, about 1.9% wt, about 2.0% wt, about 2.1% wt, about 2.2% wt, about 2.3% wt, about 2.4% wt, about 2.5% wt, about 2.6% wt, about 2.7% wt, about 2.8% wt, about 2.9% wt, about 3.0% wt, about 3.1% wt, about 3.2% wt, about 3.3% wt, about 3.4% wt, about 3.5% wt, about 3.6% wt, about 3.7% wt, about 3.8% wt, about 3.9% wt, about 4.0% wt, about 4.2% wt, about 4.4% wt, about 4.6% wt, about 4.8% wt, to about 5.0% wt, including all sub-ranges and values therebetween. In some embodiments, the surfactant is in an amount ranging from about 1% wt to about 3% wt, or about 2% wt.

In some embodiments of the pharmaceutical compositions disclosed herein, the pharmaceutical composition is a topical formulation. In some embodiments, the topical formulation comprises porfimer sodium and when applied to the skin, infected area, or wound of a subject, provides at least 0.01% percent of the porfimer sodium in the epidermal-to-dermal layer of the subject. In some embodiments at least 0.03% of the porfimer sodium is retained. In some embodiments, at least 0.04% of the porfimer sodium is retained.

In some embodiments of the pharmaceutical compositions disclosed herein, the topical formulation is applied under the following conditions as described in Example 7. In some embodiments at least 0.03% of the porfimer sodium is retained in the epidermis. In some embodiments, at least 0.04% of the porfimer sodium is retained in the epidermis in conditions as described in Example 7.

In some embodiments, the present disclosure provides a pharmaceutical topical formulation containing porfimer sodium and one or more pharmaceutical acceptable excipients, wherein when applied to the skin, infected area, or wound of a subject, provides at least 0.01% percent of the porfimer in the epidermal-to-dermal layer of the subject. In some embodiments, the present disclosure provides a pharmaceutical topical formulation containing porfimer sodium and one or more pharmaceutical acceptable excipients, wherein when applied to the skin, infected area, or wound of a subject, provides at least 0.03 percent of the porfimer in the epidermal-to-dermal layer of the subject. In some embodiments, the pharmaceutical topical formulation when applied to the skin, infected area, or wound of a subject, provides at least 0.04% percent of the porfimer in the epidermal-to-dermal layer of the subject.

In one embodiment, the pharmaceutical compositions of the present invention are comprised of porfimer sodium and are stable compositions relative to the prior art. In some embodiments of the pharmaceutical topical formulations disclosed herein, the composition, after 40° C./75% RH for 4 weeks, has a total impurities less than 20% by HPLC. In some embodiments of the pharmaceutical composition of the present disclosure is a topical formulation. In some embodiments, the composition of the present disclosure, after 40° C./75% RH for 4 weeks, has a total impurities less than 20% by HPLC. In some embodiments, the composition of the present disclosure, after 40° C./75% RH for 4 weeks, has a total impurities less than 19% by HPLC. In some embodiments, the composition of the present disclosure, after 40° C./75% RH for 4 weeks, has a total impurities less than 18% by HPLC. In some embodiments, the composition of the present disclosure, after 40° C./75% RH for 4 weeks, has a total impurities less than 17% by HPLC. In some embodiments, the composition of the present disclosure, after 40° C./75% RH for 4 weeks, has a total impurities less than 16% by HPLC. In some embodiments, the composition of the present disclosure, after 40° C./75% RH for 4 weeks, has a total impurities less than 15% by HPLC. In some embodiments, the composition of the present disclosure, after 40° C./75% RH for 4 weeks, has a total impurities less than 14% by HPLC. In some embodiments, the composition of the present disclosure, after 40° C./75% RH for 4 weeks, has a total impurities less than 13% by HPLC. In some embodiments, the composition of the present disclosure, after 40° C./75% RH for 4 weeks, has a total impurities less than 12% by HPLC.

In some embodiments, the composition of the present disclosure, after 25° C./60% RH for 4 weeks, has a total impurities less than 20% by HPLC. In some embodiments, the composition of the present disclosure, after 25° C./60% RH for 4 weeks, has a total impurities less than 19% by HPLC. In some embodiments, the composition of the present disclosure, after 25° C./60% RH for 4 weeks, has a total impurities less than 18% by HPLC. In some embodiments, the composition of the present disclosure, after 25° C./60% RH for 4 weeks, has a total impurities less than 17% by HPLC. In some embodiments, the composition of the present disclosure, after 25° C./60% RH for 4 weeks, has a total impurities less than 16% by HPLC. In some embodiments, the composition of the present disclosure, after 25° C./60% RH for 4 weeks, has a total impurities less than 15% by HPLC. In some embodiments, the composition of the present disclosure, after 25° C./60% RH for 4 weeks, has a total impurities less than 14% by HPLC. In some embodiments, the composition of the present disclosure, after 25° C./60% RH for 4 weeks, has a total impurities less than 13% by HPLC. In some embodiments, the composition of the present disclosure, after 25° C./60% RH for 4 weeks, has a total impurities less than 12% by HPLC.

In some embodiments, the composition of the present disclosure, after 5° C./60% RH for 4 weeks, has a total impurities less than 20% by HPLC. In some embodiments, the composition of the present disclosure, after 5° C./60% RH for 4 weeks, has a total impurities less than 19% by HPLC. In some embodiments, the composition of the present disclosure, after 5° C./60% RH for 4 weeks, has a total impurities less than 18% by HPLC. In some embodiments, the composition of the present disclosure, after 5° C./60% RH for 4 weeks, has a total impurities less than 17% by HPLC. In some embodiments, the composition of the present disclosure, after 5° C./60% RH for 4 weeks, has a total impurities less than 16% by HPLC. In some embodiments, the composition of the present disclosure, after 5° C./60% RH for 4 weeks, has a total impurities less than 5% by HPLC. In some embodiments, the composition of the present disclosure, after 5° C./60% RH for 4 weeks, has a total impurities less than 14% by HPLC. In some embodiments, the composition of the present disclosure, after 5° C./60% RH for 4 weeks, has a total impurities less than 13% by HPLC. In some embodiments, the composition of the present disclosure, after 5° C./60% RH for 4 weeks, has a total impurities less than 12% by HPLC.

In other embodiments, the composition of the present disclosure, after 5° C./60% RH for 4 weeks, has an impurity of hematoporphyrin (HP) of less than 5%, 4%, 3%, or 2% by HPLC. In other embodiments, the composition of the present disclosure, after 25° C./60% RH for 4 weeks, has an impurity of hematoporphyrin (HP) of less than 5%, 4%, 3%, or 2% by HPLC. In other embodiments, the composition of the present disclosure, after 40° C./75% RH for 4 weeks, has an impurity of hematoporphyrin (HP) of less than 5%, 4%, 3%, or 2% by HPLC.

In other embodiments, the composition of the present disclosure, after 5° C./60% RH for 4 weeks, has an impurity of total hydroxyvinyl deuteroporphyrin (HVD) (isomers 1 and 2) of less than 10%, 9%, 8%, 7%, 6%, or 5% by HPLC. In other embodiments, the composition of the present disclosure, after 25° C./60% RH for 4 weeks, has an impurity of total hydroxyvinyl deuteroporphyrin (HVD) (isomers 1 and 2) of less than 10%, 9%, 8%, 7%, 6%, or 5% by HPLC. In other embodiments, the composition of the present disclosure, after 40° C./75% RH for 4 weeks, has an impurity of total hydroxyvinyl deuteroporphyrin (HVD) (isomers 1 and 2) of less than 10%, 9%, 8%, 7%, 6%, or 5% by HPLC.

In other embodiments, the composition of the present disclosure, after 5° C./60% RH for 4 weeks, has an impurity of protoporphyrin (PP) of less than 5%, 4%, 3%, or 2% by HPLC. In other embodiments, the composition of the present disclosure, after 25° C./60% RH for 4 weeks, has an impurity of protoporphyrin (PP) of less than 5%, 4%, 3%, or 2% by HPLC. In other embodiments, the composition of the present disclosure, after 40° C./75% RH for 4 weeks, has an impurity of protoporphyrin (PP) of less than 5%, 4%, 3%, or 2% by HPLC.

The compositions of the present disclosure can be utilized to treat a subject in need thereof. In certain embodiments, the subject is a mammal such as a human, or a non-human mammal. When administered to subject, such as a human, the composition or the compound may be administered as a pharmaceutical composition comprising, for example, a compound of the disclosure and a pharmaceutically acceptable carrier. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, methyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols and sugar alcohols, such as glycerin, sorbitol, mannitol, xylitol, erythritol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances, including salts such as sodium chloride, employed in pharmaceutical formulations. In some embodiments, when such pharmaceutical compositions are for human administration, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as lyophile for reconstitution, powder, solution, syrup, injection or the like. The composition can also be present in a solution suitable for topical administration.

In some embodiments, the pharmaceutical compositions of the present disclosure are formulated for topical administration, e.g., to an infected area, which can include a superficial and/or subcutaneous skin infection (e.g., bacterial and/or fungal infections). In some embodiments, the compositions of the present disclosure are formulated for topical administration to an area of non-intact skin. Non-intact skin can include, but is not limited to, skin and soft tissue infections, skin lesions, vesicles, chronic ulcers, cysts, blisters, bullae, open sores such as decubitus ulcers (bed sores) and other pressure sores, cellulitis sores, erysipelas lesions, wounds, burn wounds, carbuncles, furuncles, cutaneous ulcers, or other conditions where the skin is damaged, broken, cracked, breached and/or otherwise compromised. Topical formulations generally include a sterile buffer, such as a sterile PBS, water, or saline buffer, or a sterile SM buffer. A variety of buffers may be used in the context of the present disclosure and will be readily apparent to a person having ordinary skill in the art. For example, in some embodiments, suitable buffers include sodium or potassium citrate, citric acid, phosphate buffers such as sodium phosphate, boric acid, sodium bicarbonate and various mixed phosphate buffers including combinations of $Na_2HPO_4$, $NaH_2PO_4$ and $KH_2PO_4$. In some embodiments, sodium phosphate buffer is used. In some embodiments, sodium citrate buffer is used. Accordingly, the formulation pH may vary from about 5 to about 10. In some embodiments, the formulation pH is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10. In some embodiments, the formulation pH is about 7.4.

For topical application to the skin, the pharmaceutical compositions of the present disclosure may be combined with one or a combination of carriers for topical formulations. Carriers for topical formulations may comprise semi-solid and/or gel-like vehicles, which may include a polymer thickener, water, preservatives, active surfactants, emulsifiers, and/or a solvent or mixed solvent system. U.S. Pat. No. 5,863,560 discloses a number of different carrier combinations that can aid in the exposure of skin to a medicament, and its contents are incorporated herein by reference. The carrier may or may not involve a controlled-release formulation, e.g., as disclosed in US 2008/0260697, the contents of which are incorporated herein by reference. In some embodiments, the carrier may or may not involve a viscous formulation, e.g., a gel, e.g., as disclosed in US 2009/0191254, the contents of which are incorporated herein by reference.

In some embodiments, topical pharmaceutical compositions of the present disclosure are provided in a hermetically sealed container. The container may a vial, syringe, tube, bottle, ampoule (e.g. blow-fill-seal polypropylene ampules), sachet, or the like; and may comprise or consist of glass, plastic, or other suitable material. Ampoules, for example, generally are produced industrially from short lengths of glass tubing, shaped by heating with gas torches and gravity. Computer vision techniques often are employed, e.g., for quality control. The filling and sealing of ampoules may be done by automated machinery. Blank ampoules can be purchased from scientific glass supply houses and sealed, e.g., with a small gas torch, preferably under inert atmospheres. In some embodiments, the container also may be filled with an inert gas, in addition to the pharmaceutical composition. In some embodiments, the composition is provided in an ampoule, or other suitable container, and transferred for use to a vehicle suitable for direct contact with non-intact skin, e.g., a patch, wipe, bandage, dressing, as described below.

In some embodiments, topical administration of a pharmaceutical composition of the present disclosure comprises use of a dressing. The pharmaceutical composition of the present disclosure may be incorporated into a dressing and/or applied separately along with the use of a dressing. A dressing promotes healing by keeping a wound moist, creating a barrier against infection, and/or keeping the surrounding skin dry, and limiting the exposure of the PDT active ingredients to light. The degree of moisture in a wound is to be considered when treating topical wounds (e.g. skin and soft tissue infections). High levels of exudate warrant the choice of a moisture-absorbing material, including but not limited to alginates, foams, collagen-alginate combinations, carboxymethylcellulose materials, or gauze. Low exudate and desiccated wounds generally respond well to hydrogels. Hydrogel sheets often comprise three-dimensional networks of cross-linked hydrophilic polymers. Amorphous hydrogels are similar in composition to hydrogel sheets but lack the cross-linking. The gel also may comprise additional ingredients, such as collagens, alginate, or complex carbohydrates. Alginate dressings often comprise calcium or calcium-sodium salts of natural polysaccharides derived from brown seaweed. When the alginate material comes into contact with sodium-rich wound exudates, an ion exchange takes place, producing a hydrophilic gel. Additional dressing choices include but are not limited to films including adhesive-backing films, gels, and foams including silicone-coated foams, hydrocolloids, collagen-based dressings, absorbent polymers, and the like. Hydrocolloid dressings often comprise adhesive, absorbent, and elastomeric components. Carboxymethylcellulose, for example, is a common absorptive ingredient. Hydrofiber dressing also often comprise carboxymethylcellulose, for example, sodium carboxymethylcellulose. Foam dressings often comprise a polymer, often polyurethane, with small, open cells that are able to hold fluids. Some varieties of foam dressings have a waterproof film covering the top surface and may have an adhesive coating on the wound contact side or on the wound border. Film dressings often comprise a single thin transparent sheet of polyurethane coated on one side with an adhesive. The sheet is permeable to gases and water vapor but impermeable to wound fluids. Hydrofiber dressings often comprise sodium carboxymethylcellulose fibers. Collagen-based dressings often comprise purified collagen derived from bovine, porcine, equine, or avian sources. Collagen-based dressings are believed to aid wound healing e.g., by stimulating fibroblast production.

In some embodiments, topical administration of a pharmaceutical composition of the present disclosure comprises instillation. The pharmaceutical compositions of the present disclosure may be incorporated into an instillation and/or applied separately along with the use of an instillation. Instillation refers to administration by introduction of the fluid pharmaceutical composition gradually, e.g., drop by drop of the fluid. Typical instillation therapy instills fluid into a wound under a low positive pressure. Devices for use in instillation include, e.g., Kritter-type instillation catheters (see, e.g., Brent H. et al. 2005. Wounds 17(2):37-48). Techniques known in the art to improve instillation and distribution of the fluid include, but are not limited to, filling a wound with instillation fluid, applying porous wound fillers, and/or combining with negative pressure wound therapy.

Modes of administration described herein and/or known in the art may be used to deliver desired dosages of compositions of the disclosure and in accordance with suitable dosage regimens. Dosages and dosage regimens may vary depending on the particular formulation, route of administration, condition being treated, and other factors. Animal experiments may provide reliable guidance for the determination of effective doses in human therapy, e.g., as within the skill of the ordinary physician. Interspecies scaling of effective doses can be performed by one of ordinary skill in the art following the principles described, e.g., by Mordenti, J. et al. "The use of interspecies scaling in toxicokinetics" in Toxicokinetics and New Drug Development, Yacobi et al., Eds., Pergamon Press, New York 1989, pp 42-96.

The formulations may conveniently be presented in unit dosage form and can be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect.

Compositions can also be formulated so as to provide slow or controlled release of the active ingredient therein using, for example, hydroxypropylmethyl cellulose in varying proportions to provide the desired release profile, other polymer matrices, liposomes, porphysomes, nanoparticles and/or microspheres. They can be sterilized by, for example, filtration through a bacteria-retaining filter, or by incorporating sterilizing agents in the form of sterile solid compositions that can be dissolved in sterile water, or some other sterile injectable medium immediately before use.

Liquid dosage forms useful for topical administration include pharmaceutically acceptable emulsions, lyophiles for reconstitution, microemulsions, solutions, suspensions, gels, syrups and elixirs. In addition to the active ingredient, the liquid dosage forms can contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (such as cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the topical compositions can also include adjuvants such as wetting agents, emulsifying and suspending agents, and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound can be mixed under sterile conditions with a pharmaceutically acceptable carrier, and with any preservatives or buffers that can be required. The ointments, pastes, creams and gels can contain, in addition to an active compound, one or more excipients or carriers, such as animal and vegetable fats, oils, waxes, paraffins, starch, tragacanth, cellulose derivatives, polyethylene glycols, silicones, bentonites, silicic acid, talc, polymers, salts, and zinc oxide, or mixtures thereof. In some embodiments, the PS composition is in the form of an aqueous solution. In some embodiments, the excipient comprises a salt selected from sodium chloride. In some embodiments, the excipient comprises sodium chloride.

In some cases, in order to prolong the effect of a drug, it is desirable to slow the absorption of the drug. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally administered drug form is accomplished by dissolving or suspending the drug in an oil vehicle.

Actual dosage levels of the active ingredients in the pharmaceutical compositions can be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect, or the frequency in which the therapy is delivered to the patient. It is generally understood that the effective amount of the compound will vary according to the weight, sex, age, and medical history of the subject. Other factors which influence the effective amount can include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable dose of an active compound used in the compositions and methods of the disclosure will be that amount of the compound that is the lowest dose effective to produce a therapeutic effect. Such an effective dose will generally depend upon the factors described above.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. In some embodiments, the antioxidant is phenoxyethanol.

In some embodiments of the pharmaceutical compositions disclosed herein, the antioxidant is in an amount ranging from 0.01% wt to about 5% wt, including about 0.01%, about 0.05%, about 0.1% wt, about 0.2% wt, about 0.3% wt, about 0.4% wt, about 0.5% wt, about 0.6% wt, about 0.7% wt, about 0.8% wt, about 0.9% wt, about 1% wt, about 1.1% wt, about 1.2% wt, about 1.3% wt, about 1.4% wt, about 1.5% wt, about 1.6% wt, about 1.7% wt, about 1.8% wt, about 1.9% wt, about 2.0% wt, about 2.1% wt, about 2.2% wt, about 2.3% wt, about 2.4% wt, about 2.5% wt, about 2.6% wt, about 2.7% wt, about 2.8% wt, about 2.9% wt, about 3.0% wt, about 3.1% wt, about 3.2% wt, about 3.3% wt, about 3.4% wt, about 3.5% wt, about 3.6% wt, about 3.7% wt, about 3.8% wt, about 3.9% wt, about 4.0% wt, about 4.2% wt, about 4.4% wt, about 4.6% wt, about 4.8% wt, to about 5.0% wt, including all sub-ranges and values therebetween. In some embodiments, the antioxidant is in an amount ranging from 0.5% wt to about 1.5% wt, or about 1.0% wt.

The topical mode of delivery may include a smear (e.g. finger swipe or with an applicator), a spray, a foam, a bandage, a time-release patch, a liquid-absorbed wipe, and combinations thereof. In some embodiments, the compositions of the present disclosure are provided, either directly or in a carrier(s), in a patch, wipe, bandage, dressing, or other vehicle suitable for direct contact with the skin, in particular, a SSTI.

Without wishing to be bound by theory, it is believed that this success is due to the composition in combination with the photodynamic agent, porfimer sodium. The composition is able to stabilize the porfimer sodium. Further, inclusion of skin penetrants and other solvents allow the controlled release and permeation of porfimer sodium. Additionally, drying of the composition on the surface of the tissue is remedied by selection of particular compositions, especially those including a humectant. Further, selection of the appropriate viscosity of composition allows effective skin contact that enhances spreading which keeping the active agent localized to the infection site.

Methods of Use

In some embodiments, the present disclosure provides methods for treating a topical skin infection, comprising administering to a subject in need thereof a therapeutically effective amount of a composition containing porfimer sodium, wherein the composition is applied to the skin infection (e.g. applied to the surface of the infection). In some embodiments, the skin infection is a skin and soft tissue infection (SSTI), the acute bacterial skin and skin structure infections (ABSSSI), both complicated and uncomplicated.

In some embodiments, the present disclosure provides methods for treating an infected area, comprising administering to a subject in need thereof any pharmaceutical composition or formulation of the present disclosure, wherein the composition is applied to the infected area (e.g., applied to the surface of the wound); and light is applied to the infected area. In some embodiment, the light ranges from about 380 nm to about 850 nm in wavelength. In some embodiments, the light ranges from about 400 nm to about 700 nm in wavelength. In some embodiments, the light is about 630 nm in wavelength. In some embodiments, the present disclosure provides a method for treating a microbial infection, comprising administering to a subject in need thereof a therapeutically effective amount of a composition a formulation of the present disclosure, wherein the composition or formulation is applied to the infection; and light is applied to the infected area. In some embodiments, the light ranges from about 380 nm to about 850 nm in wavelength. In some embodiments, the light ranges from about 400 nm to about 700 nm in wavelength. In some embodiments, the light is about 630 nm in wavelength. In some embodiments, the infected area is a wound. In a specific embodiment, the wound is a topical wound. In some embodiments, the area or topical wound is infected by one or more bacterial and/or fungal pathogens. In some embodiments, the area or topical wound is infected by antibiotic resistant bacterial pathogens.

Topical treatment provides the advantages of avoiding systemic adverse effects, providing increased target site concentration, and allowing the use of agents not available for systemic therapy, and avoiding the microbial resistance mechanisms associated with systemic therapies such as, but not limited to, biofilms. In some embodiments, mechanical debridement may be used to improve topical treatment because it reduces the bioburden of bacteria present and also opens a time-dependent therapeutic window for topical antimicrobial therapy (TAT) (Wolcott R D, et al. 2010. J Wound Care 19:320-328).

In some embodiments, the infected area is infected with one or more Gram positive bacteria. In some embodiments, the infected area is infected with one or more Gram negative bacteria. In some embodiments, the infected area is infected with one or more fungal pathogens. In some embodiments, the infected area is infected with Gram positive bacteria *Staphylococcus aureus*(+), *Staphylococcus aureus* MRSA (+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), or with Gram negative bacteria *Prevotella*(−), *Porphyromonas gingivalis* (−), *Salmonella enterica*(−), *Escherichia coli*(−), *Yersinia intermedia*(−), *Acinetobacter baumannii*(−), *Neisseria gonorrhea*(−), *Haemophilus influenza*(−), *Fusobacterium nucleatum*(−), or *Moraxella catarrhalis*(−). In some embodiments the infected area is infected with *Candida* spp., *Candida albicans*, *Candida glabrata*, *Candida parasilosis*, *Candida krusei*, *Candida tropicalis*, and/or *Candida guilli-*

*ermondi*. In some embodiments, the infected area is infected with one or more of the following Gram positive bacterial pathogens: *Staphylococcus aureus*(+), *Staphylococcus aureus* MRSA(+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), or with Gram negative bacteria *Prevotella*(−), *Porphyromonas gingivalis*(−), *Salmonella enterica*(−), *Escherichia coli*(−), *Yersinia intermedia*(−), *Acinetobacter baumannii*(−), *Neisseria gonorrhea*(−), *Haemophilus influenza*(−), *Fusobacterium nucleatum*(−), or *Moraxella catarrhalis*(−). In some embodiments, the infected area is infected with one or more of the following fungal pathogens: *Candida, C. albicans, C. glabrata, C. parasilosis, C. krusei, C. tropicalis, C. guilliermondi*. In some embodiments, the infected are is a wound. In a specific embodiment, the wound is a topical wound.

In some embodiments, the porfimer sodium compositions of the present disclosure have activity against bacterial flora found in chronic sinusitis in adults bacterial sinusitis including: *Streptococcus pneumonia* (Gram positive facultative anaerobe), *Moraxella catarrhalis* (Gram-negative, aerobe), *Staphylococcus aureus* (Gram-positive, facultative anaerobic), Methicillin-resistant *Staphylococcus aureus* (MRSA) (Gram positive facultative anaerobe), *Prevotella* spp. (Gram-negative, obligate anaerobe), *Peptostreptococcus* spp. (Gram-positive, anaerobic), *Fusobacterium nucleatum* (Gram-negative, anaerobic), *Porphyromonas gingivalis* (Gram-negative, anaerobic), *S. pneumoniae* (Gram positive facultative anaerobe) and *Propionibacterium acnes* (Gram-positive, anaerobic).

Biofilms of *S. aureus* and other bacteria that are present in infections like SSTIs increase the difficulty of successful infection management and reduction. Combinations of SSTI-relevant bacteria forming multispecies biofilms containing e.g. *S. aureus* have demonstrated greater resistance, virulence and pathogenicity than comparable single-species biofilms. The presence of such complex biofilms in SSTI patients is considered to be largely responsible for the chronic, persistent nature of these infections.

In some embodiments, the bacterial pathogen exhibits resistance to one or more antibiotics. Of particular concern are the methicillin-resistant *Staphylococcus aureus* strains (MRSA). MRSA remained an uncommon occurrence in hospital setting until the 1990's, when there was an explosion in MRSA prevalence in hospitals. MRSA now is considered endemic to hospitals, especially in the UK (Johnson A P et al. 2001 J. Antimicrobial Chemotherapy 48(1): 143-144). Moreover, MRSA presents a new threat in diabetic foot infections (Retrieved Jan. 17, 2009, from CDC: Centers for Disease Control and Prevention Web site).

The porfimer sodium compositions of the present disclosure have activity against a plurality of bacterial and fungal strains. In some embodiments, the porfimer sodium compositions have activity in-vitro and in-vivo against a plurality of strains including but not limited to Gram positive bacteria *Staphylococcus aureus*(+), *Staphylococcus aureus* MRSA (+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), or with Gram negative bacteria *Prevotella*(−), *Porphyromonas gingivalis* (−), *Salmonella enterica*(−), *Escherichia coli*(−), *Yersinia intermedia*(−), *Acinetobacter baumannii*(−), *Neisseria gonorrhea*(−), *Haemophilus influenza*(−). *Fusobacterium nucleatum*(−), or *Moraxella catarrhalis*(−) or one or more of the following fungal pathogens: *Candida, C. albicans, C. glabrata, C. parasilosis, C. krusei, C. tropicalis, C. guilliermondi*.

Accordingly, some embodiments of the present disclosure provide methods of treating and/or preventing infections and wounds associated with Gram positive bacteria *Staphylococcus aureus*(+), *Staphylococcus aureus* MRSA(+), *Peptostreptococcus anaerobius*(+), *Proprionibacterium acnes* (+) (now referred to as *Cutibacterium acnes*), *Bacillus thuringiensis*(+), *Bacillus atrophaeus*(+), *Streptococcus Mutans*(+), *Streptococcus pneumoniae*(+), or with Gram negative bacteria *Prevotella*(−), *Porphyromonas gingivalis* (−), *Salmonella enterica*(−), *Escherichia coli*(−), *Yersinia intermedia*(−), *Acinetobacter baumannii*(−), *Neisseria gonorrhea*(−), *Haemophilus influenza*(−), *Fusobacterium nucleatum*(−), or *Moraxella catarrhalis*(−) or *Candida* spp., *Candida albicans, Candida glabrata, Candida parasilosis, Candida krusei, Candida tropicalis*, and/or *Candida guilliermondi*.

In some specific embodiments, the methods of treating and/or preventing infections or wounds are associated with *Staphylococcus aureus, Staphylococcus aureus* MRSA, *P. anaerobius, P. acnes, B. thuringiensis, Bacillus atrophaeus, S. mutans, S. pneumoniae, Prevotella, P. gingivalis, S. enterica, E. coli, Y. intermedia, A. baumannii, N. gonorrhoea, H. influenza, F. nucleatum, M. catarrhalis* or one or more of the following fungal pathogens: *Candida* spp., *C. albicans, C. glabrata, C. parasilosis, C. krusei, C. tropicalis, C. guilliermondi* in both humans and animals using the porfimer sodium compositions. In other aspects, the present disclosure provides methods of treating and/or preventing infections associated with related species or strains of these bacteria. In some embodiments, the bacterial infection is a SSTI. *Staphylococcus aureus, Staphylococcus aureus* MRSA, *P. anaerobius, P. acnes, B. thuringiensis, B. atrophaeus, S. mutans, S. pneumoniae, Prevotella, P. gingivalis, S. enterica, E. coli, Y. intermedia, A. baumannii, N. gonorrhoea, H. influenza, F. nucleatum, M. catarrhalis* are responsible for many severe opportunistic infections particularly in individuals with SSTIs.

The pharmaceutical compositions of the present disclosure are contemplated for treating and/or preventing a wound, associated with *Staphylococcus aureus, Staphylococcus aureus* MRSA, *P. anaerobius, P. acnes, B. thuringiensis, B. atrophaeus, S. mutans, S. pneumoniae, Prevotella* spp., *P. gingivalis, S. enterica, E. coli, Y. intermedia, A. baumannii, N. gonorrhoea, H. influenza, F. nucleatum, M. catarrhalis*. In some embodiments, the wound is infected with one or more of the following fungal pathogens: *Candida* spp., *C. albicans, C. glabrata, C. parasilosis, C. krusei, C. tropicalis, C. guilliermondi* or associated with other species or strains of bacteria, including, but not limited to, infected area such as infections of the skin, infections in and around wounds, chronic ulcers, ulcers associated with burn wounds, post-operative infections, infections associated with catheters and surgical drains, and infections of the blood.

PDT using porfimer sodium compositions of the present disclosure find use as an effective noninvasive or minimally invasive treatment for oral, head & neck, superficial and/or subcutaneous infections (e.g., bacterial and/or fungal infections) including, but not limited to, infections resulting from sinusitis, wounds, open fractures, surgical implants, and surgical procedures. In some embodiments, the compositions find use in treating and/or preventing bacterial infections associated with areas of non-intact skin, including but not limited to, infections associated with cutaneous ulcers, skin lesions, vesicles, cysts, blisters, bullae, open sores such as decubitus ulcers (bed sores) and other pressure sores, chronic ulcers, cellulitis, impetigo and sores associated therewith, erysipelas and lesions associated therewith, wounds, burns and wounds associated therewith, carbuncles, furuncles or other conditions where the skin is damaged, cracked, broken, breached, and/or otherwise compromised.

In any of the embodiments described herein, the porfimer sodium compositions may be used to treat an infection (e.g. SSTI, ABSSSI) of one or more of the following fungal pathogens: Candida, spp., C. albicans, C. glabrata, C. parasilosis, C. krusei, C. tropicalis, C. guilliermondi.

In some embodiments of the methods for treating an infected area, after administration of the porfimer sodium composition, one or more of the following occurs: (i) reducing and or dispersing a microbial (e.g. bacterial and/or fungal) biofilm, (ii) impairing growth or formation of a microbial (e.g. bacterial and/or fungal) biofilm, and (iii) preventing reformation or spread of a microbial (e.g. bacterial and/or fungal) biofilm. In some embodiments, the porfimer sodium composition treats, manages, and/or lessens the severity of a skin and soft tissue bacterial or fungal infection by one or both of: (i) prevention of the infection by the bacterial or fungal pathogen; and/or (ii) reduction of the bacterial or fungal pathogen. In some embodiments, the porfimer sodium composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm formation by the bacterial or fungal pathogen; (iv) inhibition of biofilm or microbial pathogen invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement. In some embodiments, the subject experiences two or more of the recited outcomes. In some embodiments, the subject experiences three or more of the recited outcomes. In some embodiments, the subject experiences four or more of the recited outcomes. In some embodiments, the subject experiences all of the recited outcomes.

In some embodiments of the methods of the present disclosure, after administration of the composition or formulation, one or more of the following occurs: (i) reducing and or dispersing a bacterial and/or fungal biofilm, (ii) impairing growth or formation of a bacterial and/or fungal biofilm, and (iii) preventing reformation or spread of a bacterial and/or fungal biofilm. In some embodiments, the subject experiences at least one of the recited outcomes. In some embodiments, the subject experiences at least two of the recited outcomes. In some embodiments, the subject experiences all of the recited outcomes. In some embodiments of the methods for treating an infected area, the subject experiences one or more of the following outcomes following the completion of dosing: less reinfection/relapse; resolution or improvement in signs and/or symptoms of infection that include redness, swelling, induration, exudate, pain, warmth (at site of infection) or fever; improved quality of life; eradication of insulting pathogens and/or biofilm; reduced need for concurrent systemic antibiotics.

In some embodiments, the methods for the photodynamic treatment include treating an infection without or the minimization of adverse reactions or side effects due to photodynamic treatment. In a specific embodiment, when the composition and then light is applied to the, infection, skin or wound of the subject, there is a minimalization of adverse side effects, such as the minimization of pain, edema, pruritis and/or erythema. In a specific embodiment, the photodynamic agent is porfimer sodium. In another specific embodiment, the adverse side effects are minimalized more than other photodynamic treatment agents when applied topically to a subject. Indeed, one of the most significant drawbacks of the topical use of photodynamic agents is significant pain during light application. For example, the topical application of both 5-ALA and methyl-ALA are known to cause specific pain during light application, likely due to the fact that the drug localizes in hair follicles, nerve endings, epidermal cells and sebaceous glands. This requires novel methods to reduce pain during therapy in this field.

Accordingly, embodiments of the present invention include a method for treating wounds in a subject, comprising administering to the subject in need thereof any pharmaceutical composition or formulation described herein, wherein the composition is applied to the subject; and light is applied to the subject, wherein there is a minimalization of adverse side effects, such as the minimization of pain, edema, pruritis and/or erythema. In a specific embodiment, the pharmaceutical composition comprises a photosensitizer and one or more gelling agents. In a specific embodiment, the photosensitizer is porfimer sodium (Photofrin®).

In a specific embodiment, the subject does not suffer from pain when the light is applied to the infection, wound or skin of the subject. In another embodiment, the subject does not suffer from pain per the visual analog scale of pain when the light is applied to the infection, wound or skin of the subject. See, e.g., Bodian C A, Freedman G, Hossain S, Eisenkraft J B, Beilin Y. *The Visual Analog Scale for Pain. Anesthesiology* 2001: 95:1356-61. In a specific embodiment, the subject suffers from a level of pain of 10, 9, 8, 7, 6, 5, 4, 3, 2, 1 or less per the visual analog scale of pain when the light is applied to the subject. In a specific embodiment, the subject suffers from a level of pain of 5, 4, 3, 2, 1 or less per the visual analog scale of pain when the light is applied to the subject. In a specific embodiment, the subject suffers from a level of pain of 3, 2, 1 or less per the visual analog scale of pain when the light is applied to the subject. In a specific embodiment, the subject suffers from a level of pain of 2, 1 or less per the visual analog scale of pain when the light is applied to the subject.

In a specific embodiment of the methods herein, the pharmaceutical composition is applied to the infection and/or skin of the subject for about 1, 2, 3, 4, 5, 6, 7, 8, 9, 10, 11, 12, 12, 14, 14, 16, 17, 18, 19, 20, 21, 22, 23, 24, 25, 26, 27, 28, 29, 30, 35, 40, 45, 50, 55, 60, or 120 minutes. In another embodiment, the light is applied to the subject for about 1, 2, 3, 4, 5, 6, 7, 8, 9, 10, 11, 12, 12, 14, 14, 16, 17, 18, 19, 20, 21, 22, 23, 24, 25, 26, 27, 28, 29, 30, 35, 40, 45, 50, 55, 60, or 120 minutes.

In a specific embodiment, the composition is applied to the subject for about 15 or 30 minutes, and light is applied for about 5-25 minutes. In another embodiment, the subject does not develop erythematous lesions. In another embodiment, the subject does not develop erythematous lesions higher than 1 or 2 per the erythema scale from treatment on the subject, In some embodiments of the methods disclosed herein, the porfimer sodium composition is administered three times per day, two times per day, once daily, every other day, once every three days, three times per week, once every week, once every other week, once every month, or once every other month. In some embodiments, the composition is administered once daily or three times per week. In some embodiments, the subject is administered multiple doses of the porfimer sodium composition daily or weekly for a length of time ranging from about one week to about 12 weeks. In some embodiments, the subject is administered multiple doses of the porfimer sodium composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the porfimer sodium composition daily or weekly for a length of about 4 weeks to about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

Embodiments

1. A pharmaceutical composition comprising a photosensitizer and one or more gelling agents.

2. The pharmaceutical composition of embodiment 1, wherein the photosensitizer is selected from one or more of the group consisting of porphyrins, chlorins (HPPH; NPe6; Temoporfrin (Foscan), mTHPC)), and porphysomes as in: pyropheophorbide nanovesicles including, bacteriochlorophyll porphysomes, zinc pyropheophorbide porphysomes and pyropheophyorbide porphysomes, and chlorin-like compounds (benzoporphyrin; Verteporfin, bacteriochlorins and phthalocyanines, purpurins (tin ethyl etiopurpurin); Metalloporphyrins (Texaphyrins); Pheophorbides (TOOKAD); Protoporphyrins (Levulan, Metvix, 5-ALA (PpIX)) and nonporphyrin based photosensitizers including phenothiazinium salts such as Methylene Blue, Toluidine Blue, Nile Blue, Cyanines, hypericin and Chalcogenpyrilium dyes; PPA904; benzophenothiazinium dye EtNBS; the xanthene class of fluorescent dyes that includes fluorescein and Rose Bengal; Fullerenes (C60 fullerene coupled to polar diserinol groups or quarternary pyrrolidinium groups); Squaraogenines, BODIPY (boron-dipyrromethene) dye, Phenalenones; Hypericin, Hypocrellin, Riboflavin, Curcumin, Titanium dioxide and porfimer sodium (Photofrin®).

3. The pharmaceutical composition of embodiment 1, wherein the photosensitizer is porfimer sodium.

4. The pharmaceutical composition of embodiment 3, wherein the porfimer sodium is in an amount ranging from about 0.01% wt to about 1.0% wt; or about 0.05% wt to about 0.7% wt; or about 0.1% wt to about 0.5% wt; or about 0.15% wt to about 0.3% wt.

5. The pharmaceutical composition of embodiment 3, wherein the porfimer sodium is an amount ranging from 0.01% wt to 1.0% wt; or 0.05% wt to 0.7% wt; or 0.1% wt to 0.5% wt; or 0.15% wt to 0.3% wt.

6. The pharmaceutical composition of any one of embodiments 1-5, wherein the gelling agent is selected from one or more of the group consisting of a Carbopol polymer, carbomer, crosslinked, polyacrylic acid, lecithin such as Lecithin-PLO, hydroxyethyl cellulose, hydroxypropyl cellulose, and hydroxypropyl methylcellulose 7. The pharmaceutical composition of embodiment 6, wherein at least one gelling agent is a carbomer 8. The pharmaceutical composition of embodiment 7, wherein the gelling agent is a polymer of acrylic acid cross-linked with polyalkenyl ethers or divinyl glycol.

9. The pharmaceutical composition of embodiment 7, wherein the cabomer is a Carbopol polymer Carbopol® 71G, Carbopol® 971P, Carbopol® 974P, Carbopol® 980, Carbopol® 981, Carbopol® 5984, Carbopol® 934, Carbopol® 934P, Carbopol® 940, Carbopol® 941, and/or Carbopol® 1342.

10. The pharmaceutical composition of any one of embodiments 1-9, wherein the gelling agent is in an amount ranging from about 0.5% wt to about 3.0% wt, or from about 0.7% wt to about 2.0% wt, or from about 1.0% wt to about 1.75% wt.

11. The pharmaceutical composition of any one of embodiments 1-9, wherein the gelling agent is in an amount ranging from 0.5% wt to 3.0% wt, or from 0.7% wt to 2.0% wt, or from 1.0% wt to 1.75% wt.

12. The pharmaceutical composition of any one of embodiments 1-10, wherein the pharmaceutical composition further comprises one or more permeation enhancers.

13. The pharmaceutical composition of embodiment 7, wherein the permeation enhancer is selected from one or more of the group consisting of propylene glycol SR, polyethylene glycol 400 SR, polyethylene glycol 300 LA, diethylene glycol monoethyl ether, DMSO, and Polysorbate 80 SR.

14. The pharmaceutical composition of embodiment 13, wherein the permeation enhancer is selected from one or more of the group consisting of propylene glycol SR, DMSO, and diethylene glycol monoethyl ether.

15. The pharmaceutical composition of any one of embodiments 12-14 wherein the one or more permeation enhancers is in an amount ranging from about 1.0% to about 60%, or about 5% to about 30%, or about 20% to about 50%, or about 10% to about 40%, or about about 5% to about 15%.

16. The pharmaceutical composition of any one of embodiments 12-15, wherein the pharmaceutical composition comprises a photosensitizer, a gelling agent, one or more permeation enhancers, a humectant, a solubilizer, and a preservative.

17. The pharmaceutical composition of embodiment 16, wherein:
 i) the humectant is in an amount ranging from about 10% wt to about 20% wt, or about 15% wt;
 ii) the solubilizer is in an amount ranging from 1.0% wt to about 5% wt, or about 1% to about 3%, or about 2%; and/or
 iii) the preservative is in an amount ranging from 0.5% wt to about 5% wt, or about 0.5% wt to about 2% wt, or about 1% wt to about 3% wt.

18. The pharmaceutical composition of any one of embodiments 1-17, wherein the pharmaceutical composition is a topical formulation.

19. The pharmaceutical composition of embodiment 18, wherein the topical formulation comprises porfimer sodium and when applied to human skin under the conditions as provided in Example 7, provides at least 0.03% percent of the porfimer in the epidermis of the subject.

20. The pharmaceutical composition of embodiment 18, wherein the topical formulation comprises porfimer sodium and when applied to woundless human skin of a subject, provides at least 0.03% percent of the porfimer in the epidermal-dermal layer of the subject. 21. The pharmaceutical composition of embodiment 19 or 20, wherein the composition, after 40° C./75% RH for 4 weeks, has a total impurities less than 20% by HPLC.

22. A pharmaceutical topical formulation comprising porfimer sodium and one or more pharmaceutical acceptable excipients, wherein when applied to the, infected area, or wound of a subject, provides at least 0.03% percent of the porfimer in the dermis of the subject.

23. The pharmaceutical topical formulation of embodiment 19, wherein the topical formulation provides at least 0.04% percent of the porfimer in the epidermis of the subject.

24. The pharmaceutical topical formulation of embodiment 22 or 23, wherein the composition, after 40° C./75% RH for 4 weeks, has a total impurities less than 20% by HPLC.

25. The pharmaceutical topical formulation of any one of embodiments 22-24, wherein the pharmaceutical topical formulation further comprises a gelling agent, one or more permeation enhancers.

26. A method for treating an infected area, comprising administering to a subject in need thereof any pharmaceutical composition or formulation of any one of embodiments 1-25, wherein the composition is applied to the infected area; and light is applied to the infected area.

27. The method of embodiment 26, wherein the light ranges from about 380 nm to about 850 nm in wavelength.

28. The method of embodiment 27, wherein the light is about 630 nm in wavelength.

29. The method of any one of embodiments 26-28 wherein the infected area is infected with Gram positive bacteria *Staphylococcus aureus*(+), *Staphylococcus aureus* MRSA(+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), and/or with Gram negative bacteria *Prevotella*(−), *Porphyromonas gingivalis*(−), *Salmonella enterica*(−), *Escherichia coli*(−), *Yersinia intermedia*(−), *Acinetobacter baumannii* (−), *Neisseria gonorrhea*(−), *Haemophilus influenza*(−). *Fusobacterium nucleatum*(−), or *Moraxella catarrhalis*(−) and/or with *Candida* spp., *Candida albicans, Candida glabrata, Candida parasilosis, Candida krusei, Candida tropicalis*, and/or *Candida guilliermondi*.

30. The method of any one of embodiments 26-29, wherein after administration of the composition or formulation, one or more of the following occurs: (i) reducing and or dispersing a bacterial and/or fungal biofilm, (ii) impairing growth or formation of a bacterial and/or fungal biofilm, and (iii) preventing reformation or spread of a bacterial and/or fungal biofilm.

31. A method for treating a microbial infection, comprising administering to a subject in need thereof a therapeutically effective amount of a composition a formulation from any one of embodiments 1-25, wherein the composition or formulation is applied to the infection; and light is applied to the infected area.

32. The method of embodiment 31, wherein the light ranges from about 380 nm to about 850 nm in wavelength.

33. The method of embodiment 32, wherein the light is about 630 nm in wavelength.

34. The method of any one of embodiments 31-33, wherein the infected area is infected with Gram positive bacteria *Staphylococcus aureus*(+), *Staphylococcus aureus* MRSA(+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), and/or with Gram negative bacteria *Prevotella*(−), *Porphyromonas gingivalis*(−), *Salmonella enterica*(−), *Escherichia coli*(−), *Yersinia intermedia*(−), *Acinetobacter baumannii* (−), *Neisseria gonorrhea*(−), *Haemophilus influenza*(−), *Fusobacterium nucleatum*(−), or *Moraxella catarrhalis*(−) and/or with *Candida* spp., *Candida albicans, Candida glabrata, Candida parasilosis, Candida krusei, Candida tropicalis*, and/or *Candida guilliermondi*.

35. The method of embodiment 34, wherein the infected area is infected with *Staphylococcus aureus* MRSA.

36. The method of any embodiment of embodiments 26-35, wherein the infected area is a wound.

37. The method of embodiment 37, wherein the wound is a topical wound.

38. The method any one of embodiments 26-37, wherein at least 0.03% of the porfimer remains in the dermis of the subject.

39. The method of embodiment 38, wherein at least 0.04% of the porfimer remains in the dermis of the subject.

40. A pharmaceutical composition comprising porfimer sodium (Photofrin®) and one or more gelling agents.

41. The pharmaceutical composition of embodiment 40, wherein the porfimer sodium ranges from about 0.1% wt to about 1.0% wt.

42. The pharmaceutical composition of embodiment 41, wherein the porfimer sodium is about 0.5% wt.

43. The pharmaceutical composition of any one of embodiments 40-42, wherein the composition additional comprises about 1% wt to about 2% wt potassium iodide (KI).

44. The pharmaceutical composition of embodiment 43, wherein the KI is about 1.5% wt to about 1.7% wt 45. The pharmaceutical composition of any one of embodiments 40-44, wherein the composition additionally comprises a gelling agent selected from one or more of the group consisting of a Carbopol polymer, carbomer, crosslinked, polyacrylic acid, lecithin such as Lecithin-PLO, hydroxyethyl cellulose, hydroxypropyl cellulose, and hydroxypropyl methylcellulose.

46. The pharmaceutical composition of any one of embodiments 40-45, wherein the pharmaceutical composition further comprises one or more permeation enhancers.

47. The pharmaceutical composition of embodiment 46, wherein the permeation enhancer is selected from one or more of the group consisting of propylene glycol (such as SR), polyethylene glycol 400 SR, polyethylene glycol 300 LA, diethylene glycol monoethyl ether, DMSO, and Polysorbate 80 SR.

48. The pharmaceutical composition of embodiment 47, wherein the permeation enhancer is selected from one or more of the group consisting of propylene glycol, DMSO, and diethylene glycol monoethyl ether.

49. The pharmaceutical composition of any one of embodiments 46-48, wherein the one or more permeation enhancers is in an amount ranging from about 1.0% wt to about 60% wt, or about 5% wt to about 30% wt, or about 20% wt to about 50% wt, or about 10% wt to about 40% wt, or about 5% wt to about 15% wt.

50. The pharmaceutical composition of any one of embodiments 46-49, wherein at least one of the permeation enhancers is DMSO.

51. The pharmaceutical composition of embodiment 50, wherein the DMSO is at about 5% wt to about 20% wt.

52. The pharmaceutical composition of embodiment 51, wherein the DMSO is at about 5% wt, or about 6% wt, or about 7% wt, or about 8% wt, or about 9% wt, or about 10% wt, or about 11% wt, or about 12% wt, or about 13% wt, or about 14% wt, or about 15% wt, or about 16% wt, or about 17% wt, or about or about 18% wt, or about 19% wt, or about 20% wt.

53. The pharmaceutical composition of embodiment 52, wherein the DMSO is at about 5% wt, 10% wt or 20% wt.

54. The pharmaceutical composition of any one of embodiments 40-53, wherein the pharmaceutical composition comprises a photosensitizer, a gelling agent, one or more permeation enhancers, a humectant, a solubilizer, and a preservative.

55. The pharmaceutical composition of any one of embodiments 40-54, wherein the pharmaceutical composition is a topical formulation.

56. A method for treating an infected area, comprising administering to a subject in need thereof any pharmaceutical composition or formulation of any one of embodiments 40-55, wherein the composition is applied to the infected area; and light is applied to the infected area.

57. The method of embodiment 56, wherein the light ranges from about 380 nm to about 850 nm in wavelength.

58. The method of embodiment 57, wherein the light is about 630 nm in wavelength.

59. The method of any one of embodiments 56-58, wherein the infected area is infected with Gram positive bacteria *Staphylococcus aureus*(+), *Staphylococcus aureus* MRSA(+), *Peptostreptococcus anaerobius*(+), *Proprionibacterium acnes*(+) (now referred to as *Cutibacterium acnes*), *Bacillus thuringiensis*(+), *Bacillus atrophaeus*(+), *Streptococcus Mutans*(+), *Streptococcus pneumoniae*(+), and/or with Gram negative bacteria *Prevotella*(−), *Porphyromonas gingivalis*(−), *Salmonella enterica*(−), *Escherichia coli*(−), *Yersinia intermedia*(−), *Acinetobacter baumannii* (−), *Neisseria gonorrhea*(−), *Haemophilus influenza*(−), *Fusobacterium nucleatum*(−), or *Moraxella catarrhalis*(−) and/or with *Candida* spp., *Candida albicans*, *Candida glabrata*, *Candida parasilosis*, *Candida krusei*, *Candida tropicalis*, and/or *Candida guilliermondi*.

Methodological Development

The following (Parts 1, 2 & 3) describe the methods used in experiments detailed in this application.

Part 1. In Vitro Methodology Bacteria

Bacteria were routinely cultured using tryptic soy broth or agar at 37° C. in a 5% $CO_2$ incubator. Bacteria were isolated and suspended with 0.9% NaCl to an Optical Density (OD) of 0.1 taken at 630 nm, to generate the inoculum used for either planktonic or biofilm assays.

Experiments using planktonic cultures were carried out using *M. catarrhalis*, as a standard for further comparisons and to determine the effective drug concentration, porfimer sodium incubation time and light dose parameters which would provide an effective cell kill at the level of 5-7 logs. Once determined the experiments were repeated for all other bacterial strains examined.

The colony forming units (CFU) per mL of the starting inoculum for every experiment was determined by dilution plating. Control samples were exposed to laser at 630 nm in the absence of porfimer sodium, porfimer sodium in the absence of laser exposure, or in saline alone in the absence of porfimer sodium and 630 nm laser light. All experimental samples were dilution plated to enumerate viable CFU's. Three independent replicates were performed for each reaction condition per strain per assay.

Lyophilized porfimer sodium (Photofrin®; PF, source Pinnacle) powder was reconstituted in normal saline to a final concentration of 2.5 mg/ml. Once reconstituted, the drug was light protected. The reconstituted drug was drawn directly from this stock solution and diluted in each sample according to the final drug concentration desired for a particular experiment.

Bacteria were exposed to 630 nm laser light via a fiber optic with a lens affixed to the distal end to provide a uniform diverging light field. The accuracy of the wavelength delivered was routinely checked using an Optometrics USA Inc. 1 nm/div monochromator. Power output of the laser was measured using a UDT/Gamma Scientific 371 optical power meter and an integrating sphere. The light intensity delivered was maintained at 150 $mW/cm^2$.

Part 2: In Vitro Methodology: Yeast Strains

*Candida albicans* ATCC 90028, *C. glabrata* ATCC 90030, *C. parasilosis* 22019, *C. krusei* 6258 and *C. tropicalis* 42678 were used for direct comparison of susceptibility to killing by aPDT using porfimer sodium. Cells were transferred from a 16 h SdA plate (Difco Sabouraud Dextrose Agar, Becton Dickson, Sparks, MD) into RPMI 1640 (GIBCO Invitrogen, Grand Island, NY USA) with the addition of 5% newborn calf serum (Crane Laboratories, Syracuse NY USA). Cells were grown with shaking at 37 C until the log growth phase was reached. Cells were centrifuged for 2 min at 14,000 rpm resuspended in 0.85% NaCl and adjusted to an OD of 0.10 at 600 nm.

Yeast Isolates

Strains form the oral mucosa of adults with *Candida* infections *C. albicans*, (1 fluconisol resistant), *C. guilliermondi*, (1 amphotericin resistant), *C. parasilosis* (1 fluconisol sensitive) and *C. krusei* (1 fluconisol and amphotericin resistant). Each isolate was grown on SDA (Saouraud Dextrose Agar) in a humidified incubator at 32 C. Inoculums were prepared from individual colonies on the SDA into 5 ml of sterile 0.85% saline to a density of 0.5 McFarland standards to equalize yeast cell density.

Fungal cultures were exposed to 630 nm laser light via a fiber optic with a lens affixed to the distal end to provide a uniform diverging light field. The accuracy of the wavelength delivered was routinely checked using an Optometrics USA Inc. 1 nm/div monochromator. Power output of the laser was measured using a UDT/Gamma Scientific 371 optical power meter and an integrating sphere. The light intensity delivered was maintained at 150 $mW/cm^2$.

Part 3: In Vivo Methodology

Preparation of Bacterial Inoculum

Bacteria strains were obtained from ATCC (Manassas, VA). Bacteria were propagated from glycerol stock store at −80° C. A stab of the glycerol stock was used to inoculate 5 mL of trypticase soy broth. The cultures were incubated overnight at 37° C. with shaking at 250 rpm. The following day, a portion of overnight culture was used to prepare a streak plate onto an Oxacillin screen plate which was incubated overnight at 37° C. and single colony isolates of freshly plated bacteria were used to prepare bacterial inoculum. The morning of wounding an infection, a portion of overnight culture was used to inoculate 50 mL of trypticase soy broth and the newly inoculated media was incubated at 37° C. with shaking at 250 rpm until log phase growth was reached. The bacteria were pelleted by centrifugation at 4,000 rpm at 4° C. for 10 minutes in a Sorval tabletop centrifuge. The culture supernatant was discarded, and the bacterial pellets were suspended in a volume of sterile PBS to yield a concentration of $2 \times 10^7$ CFU/mL.

Determination of Microbial Load on Wound Surface

Wounds were swabbed with a sterile cotton tipped applicator in a serpentine motion starting at the upper left-hand margin of the wound and ending at the bottom right wound margin. A dry sterile cotton tipped applicator was used for all wounds. The swabs were placed into 14 mL falcon tubes containing 1 mL of sterile PBS. The tubes were vigorously vortexed and serial 10-fold dilutions of the PBS in the tubes containing the swabs were prepared. One hundred microliters of select dilutions for wound groups were plated onto agar plates. The plates were incubated at 35-37° C. and colonies enumerated manually. The data are reported as CFU/swab normalized to the volume of PBS in which the swabs were placed.

Determination of Microbial Load in Tissue Biopsy Samples

Tissue samples were obtained using an 8 mm biopsy punch. The biopsy punch was placed into a homogenization tube containing 1 mL of sterile PBS and stainless steel homogenization beads and the tissues were homogenized in a Reich MM300 mixer mill homogenizer. Serial 10-fold dilutions of the tissue homogenates were prepared in sterile PBS and 100 microliters of select dilutions for each wound were plated onto agar plates. The plates were incubated at 35-37° C. and the colonies were enumerated manually. Microbial loads were normalized at $CFU/mm^2$ of tissue surface area per punch.

EXAMPLES

The following examples are provided to illustrate the present disclosure, and should not be construed as limiting thereof.

Example 1: The In Vitro Antimicrobial Efficacy of Photodynamic Therapy with Porfimer Sodium This study evaluated the bactericidal efficacy of porfimer sodium based photodynamic therapy against standard and antibiotic resistant bacterial strains in planktonic and biofilm cultures. The primary efficacy endpoint was the overall cell kill analysis as determined by the enumeration of viable colony forming assays post PDT treatments as analyzed using the unpaired students two-tailed t test on log transformed data.

Methods:

Bacterial colonies were isolated and suspended in 0.9% NaCl to an optical density (OD) of 0.099.9, (0.8-0.12 is the optimum range) taken at 630 nm.

Planktonic cultures were prepared by adding bacteria to glass vials with saline and porfimer sodium to a final concentration ranging from 125 µg/ml to 150 µg/ml.

Biofilms were formed on glass coupons in culture dishes containing a bacterial inoculum for 48 hours under conditions specific to the strain. The glass coupon attached biofilms were then rinsed with saline, by dipping method, prior to the administration of the porfimer sodium. The biofilms were incubated in the dark for 15-30 minutes with a reconstituted saline solution of porfimer sodium at final concentrations ranging from 75 µg/ml-250 µg/ml. The porfimer sodium treated biofilms were then exposed to light doses at 630 nm light of 50-200 $J/cm^2$ at a power density of 150 milliwatts per $cm^2$. The light was delivered using a fiberoptic with a lens attached at the distal end to provide a uniform light field over the area of the samples being treated. The accuracy of the wavelength delivered was routinely checked using an Optometrics USA Inc. 1 nm/div monochromator. Power output of the laser was measured using a UDT/Gamma Scientific 371 optical power meter and an integrating sphere. Control samples were 1) bacterial suspensions without any light or porfimer sodium (NLNP); and 2) porfimer sodium alone in bacterial suspension without any light (NLP) and 3) light alone (L). The light alone control was exposed to the highest light dose used in that particular experiment. Light doses are in $joules/cm^2$. Power density was 150 $mW/cm^2$ for each in vitro trial. The experimental groups were conducted in triplicate. Each bar represents a replicate sample.

Figure 1B:
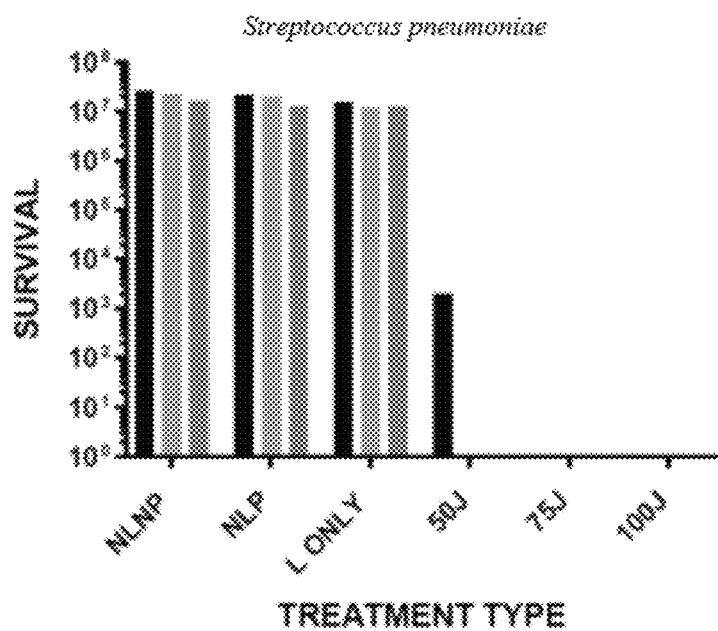
FIG. 1B shows the bactericidal effects of porfimer sodium aPDT on planktonic cultures of gram positive *Streptococcus pneumoniae*. NLNP corresponds to no laser, no porfimer. NLP corresponds to no laser but with porfimer solution. L only corresponds to laser only at highest dose. Light doses are in joules/cm$^2$. Power density was 150 mW/cm$^2$.

Results:

As shown in FIG. 1A and FIG. 1B, planktonic cultures of *M. catarrhalis* and *Streptococcus pneumoniae* treated with a porfimer sodium dose of 125 µg/ml, incubated for 10 minutes and exposed to light doses from 50-100 $J/cm^2$ provided consistent bacterial cell kill of *M. catarrhalis* at 6-7 logs. The data by conventional criteria is considered extremely statistically significant at all light dose levels with a P value of less than 0.0001 ($P<0.0001$).

Figure 2:
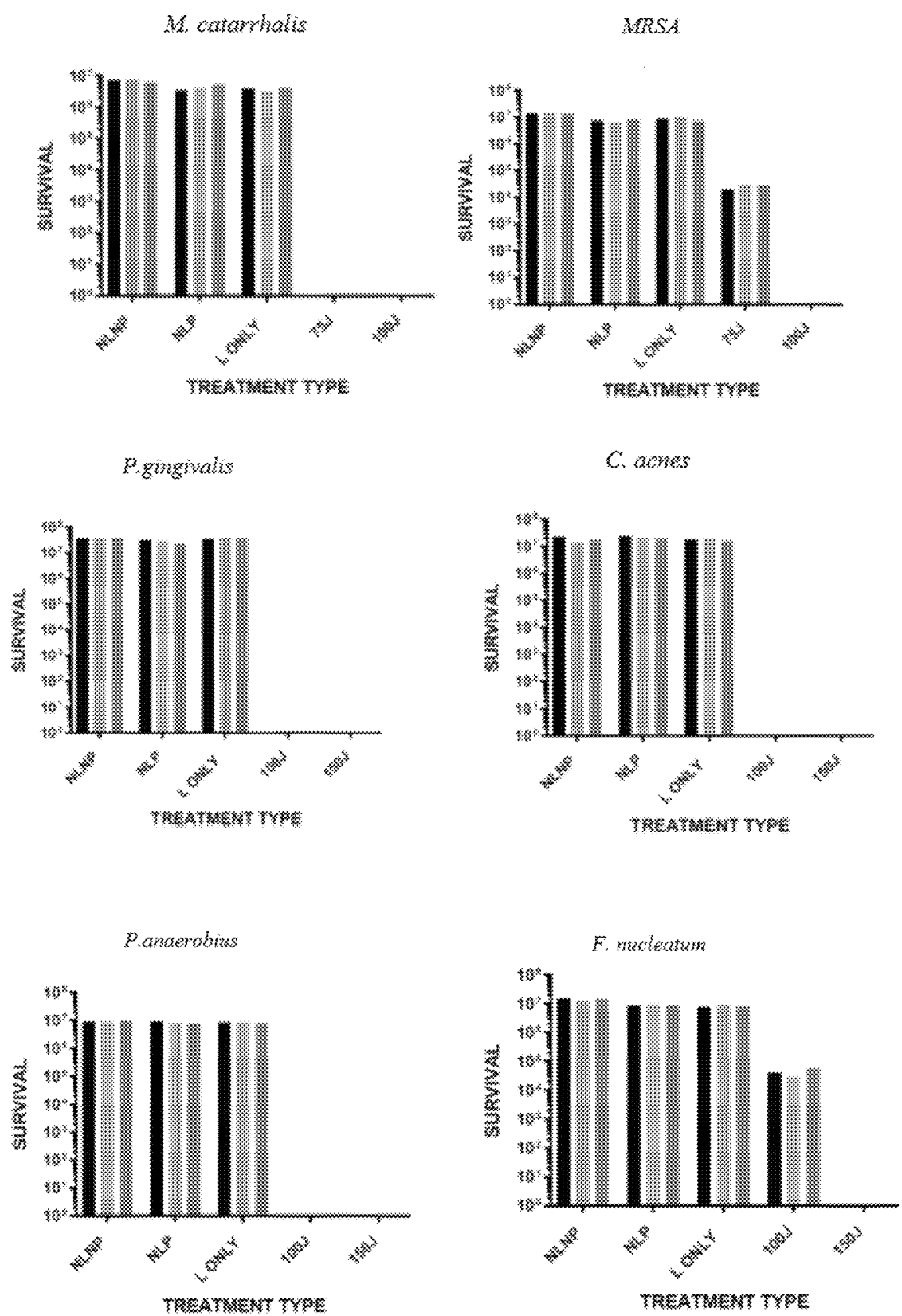
FIG. 2 shows representative CFU data from experiments conducted on 48 hour biofilms of various strains.

FIG. 2 depicts representative CFU data from experiments conducted on 48 hour biofilms of *Moraxella catarrhalis*, Methicillin resistant *Staphylococcus aureus* (MRSA), *Porphymonas gingivalis*, *Cutibacterium acnes*, *Peptostreptococcus anaerobius*, and *Fusobacterium nucleatum*. These results show aPDT with porfimer sodium decreased the viability of the bacteria in biofilm from greater than 2-7 logs depending on the dose. All strains examined showed complete reduction at the highest light doses used in the experiment (~7 log reduction). The CFU data was determined to be very statistically significant ($P=0.007$; MRSA at 75 $J/cm^2$ and *F. nucleatum* at 100 $J/cm^2$) to extremely statistically significant (P less than 0.0001) for all other CFU data depicted.

Representative data of experiments conducted on multiple bacterial planktonic or biofilm cultures is shown in Table 1. Rate of kill expressed is the highest given the specific parameters examined. As a matter of reference, a 3-log kill reduces the colony to 1,000 bacteria after a 99.9% reduction; A 4-log kill reduces the colony to 100 bacteria after a 99.99% reduction; A 5-log kill reduces the colony to 10 bacteria after a 99.999% reduction; A 6-log kill reduces the colony to 1 MRSA bacterium after a 99.9999% reduction.

TABLE 1

Bactericidal effects of porfimer sodium aPDT on bacterial planktonic or biofilm cultures.

| Culture | Species | Rate of kill | Wavelength | Light Dose | Photosensitizer Porfimer Sodium |
|---|---|---|---|---|---|
| Planktonic | *P. anaerobius* (+) | 75 J/cm2 5Log | 630 nm | 50-100 J/cm2 | 150 µg/mL |
| | *P. acnes* (+) | 75 J/cm2 7Log | | | |
| | *Prevotella* (−) | 75 J/cm2 7Log | | | |

TABLE 1-continued

Bactericidal effects of porfimer sodium aPDT on bacterial planktonic or biofilm cultures.

| Culture | Species | Rate of kill | Wavelength | Light Dose | Photosensitizer Porfimer Sodium |
|---|---|---|---|---|---|
| | P. gingivalis (−) | 75 J/cm2 7Log | | | |
| | S. aureus (+) | >7Log | 630 nm | 200 J/cm2 | 125 μg/mL |
| | MRSA (+) | >6Log | | | |
| | B. thurigiensis (+) | >6Log | | | |
| | B. atrophaeus (+) | 6Log | | | |
| | S. enterica (−) | 6Log | | | |
| | E. coli (−) | <1Log | | | |
| | Y. intermedia (−) | 7Log | | | |
| | A. baumannii (−) | 1Log | | | |
| | N. gonorrhoea (−) | 4Log | | | |
| | H. influenza (−) | 4Log | | | |
| | S. Mutans (+) | >7Log | | | |
| | S. pneumo (+) | >4Log | | 100 J/cm2 | |
| | F. nucleatum (−) | 3Log | | 50 J/cm2 | |
| | M. catarrhalis (−) | 7Log | | 200 J/cm2 | |
| Biofilm | P. anaerobius (+) | 100 J/cm2 >6Log | 630 nm | 75-100 J/cm2 | 250 μg/mL |
| | P. acnes (+) | 100 J/cm2 7Log | | | |
| | S. aureus (+) | 75 J/cm2 >6Log | | | |
| | MRSA (+) | 100 J/cm2 7Log | | | |
| | M. catarrhalis (−) | 75 J/cm2 >6Log | | | |
| | F. nucleatum (−) | 100 J/cm2 3Log | | | |
| | P. gingivalis (−) | 100 J/cm2 7Log | | | |

The above in vitro data demonstrates that porfimer sodium photodynamic therapy is an extremely effective means of reducing bacterial loads in vitro, resulting in 5-6 log reductions (>99% reduction) in planktonic and biofilm bacterial populations. Further, laser-only experiments reveal that light illumination is not responsible for any reduction in bacterial counts.

Example 2: In Vitro Experiments in Yeast

Methods:

Yeast cells of Candida albicans ATCC 90028, C. glabrata ATCC 90030, C. parasilosis 22019, C. krusei 6258 and C. tropicalis 42678 were used for direct comparison of susceptibility to killing by aPDT using porfimer sodium were transferred from a 16h SdA plate (Difco Sabouraud Dextrose Agar, Becton Dickson, Sparks, MD) into RPMI 1640 (GIBCO Invitrogen, Grand Island, NY USA) with the addition of 5% newborn calf serum (crane Laboratories, Syracuse NY USA). Cells were grown with shaking at 37 C until the log growth phase was reached. Cells were centrifuged for 2 min at 14,000 rpm resuspended in 0.85% NaCl and adjusted to an OD of 0.10 at 600 nm.

Additional experiments were conducted using strains from the oral mucosa of adults with Candida infections C. albicans, (1 fluconisol resistant), C. guilliermondi, (1 amphotericin resistant), C. parasilosis (1 fluconisol sensitive) and C. krusei (1 fluconisol and amphotericin resistant). Each isolate was grown on SDA (Saouraud Dextrose Agar) in a humidified incubator at 32 C. Inoculums were prepared from individual colonies on the SDA into 5 ml of sterile 0.85% saline to a density of 0.5 McFarland standards to equalize yeast cell density. Cultures were then exposed to 630 nm laser light via a fiber optic with a lens affixed to the distal end to provide a uniform diverging light field. Cultures were exposed to 150 mW/cm$^2$ for light doses of 45-135 J/cm$^2$.

Figure 3:
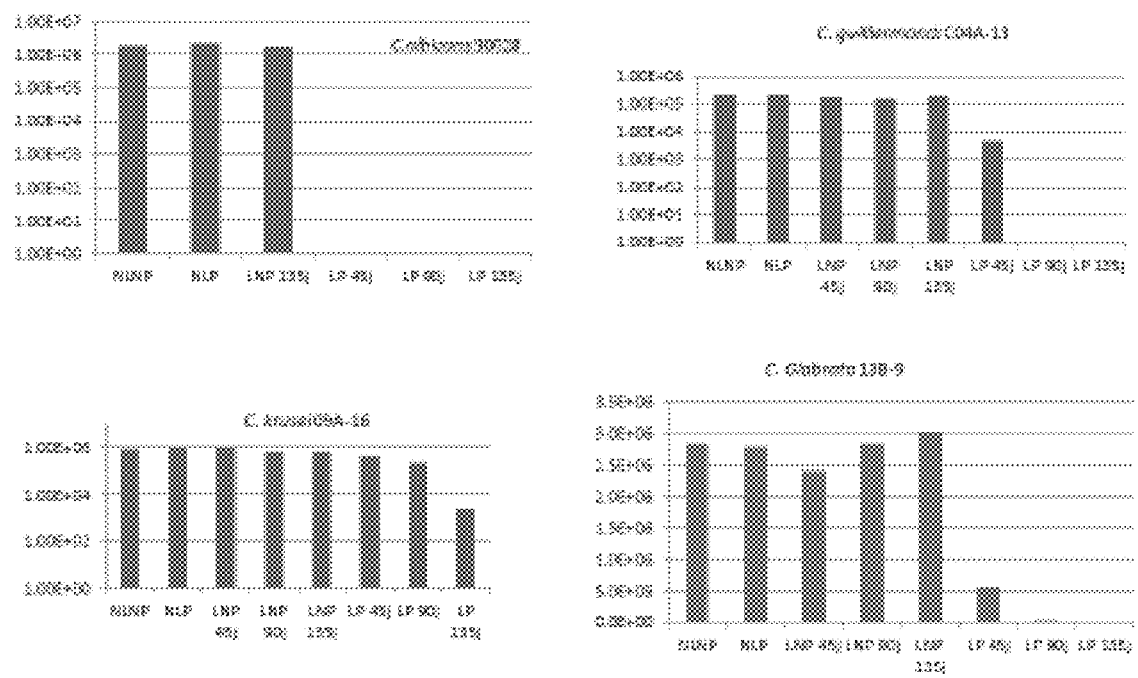
FIG. 3 shows phototoxicity of porfimer sodium induced PDT in strains from the oral mucosa of adults with *Candida* infections *C. guilliermondi*, (1 amphotericin resistant), *C. glabrata* and *C. krusei* (1 fluconisol and amphotericin resistant) compared to the standard *C. albicans* ATCC 90028.

Results:

FIG. 3 shows phototoxicity of porfimer sodium induced PDT conducted using strains from the oral mucosa of adults with Candida infections C. albicans, (1 fluconisol resistant), C. guilliermondi, (1 amphotericin resistant), C. glabrata and C. krusei (1 fluconisol and amphotericin resistant).

Figure 4:
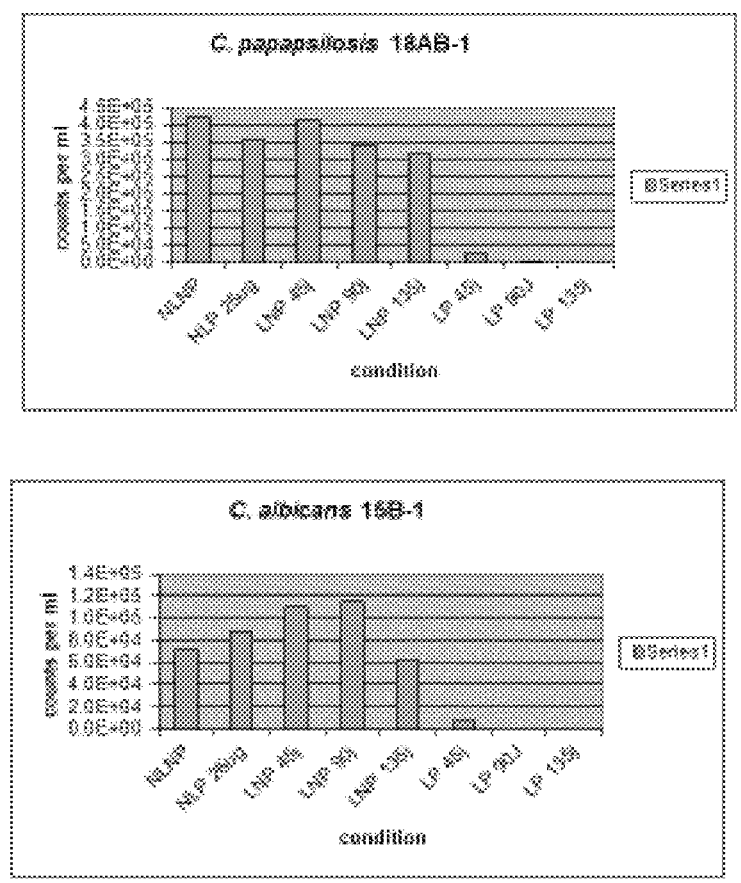
FIG. 4 shows phototoxicity of porfimer sodium induced PDT in strains from the oral mucosa of adults with *Candida* infections *C. albicans*, (1 fluconisol resistant) and *C. parasilosis* (1 fluconisol sensitive).

FIG. 4 shows phototoxicity of porfimer sodium induced PDT in strains from the oral mucosa of adults with Candida infections C. albicans, (1 fluconisol resistant) and C. parasilosis (1 fluconisol sensitive).

Figure 5A:
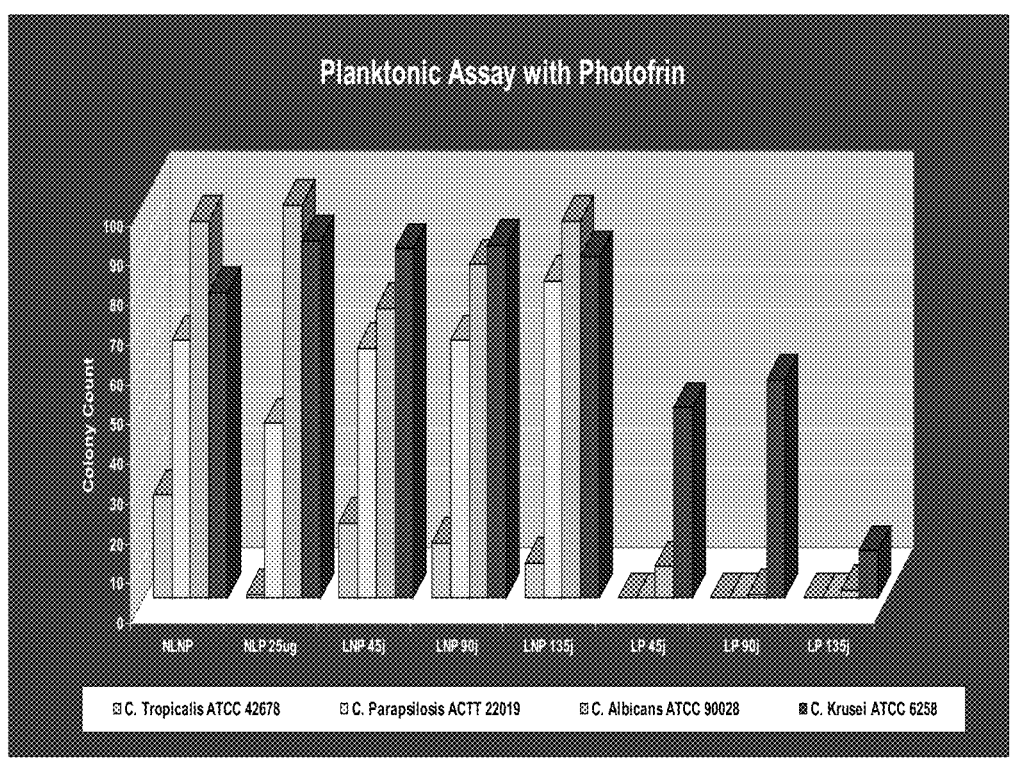
FIG. 5A shows phototoxicity of porfimer sodium and increasing light dose, on colony forming ability of various ATCC *Candida* cultures.
Figure 5B:
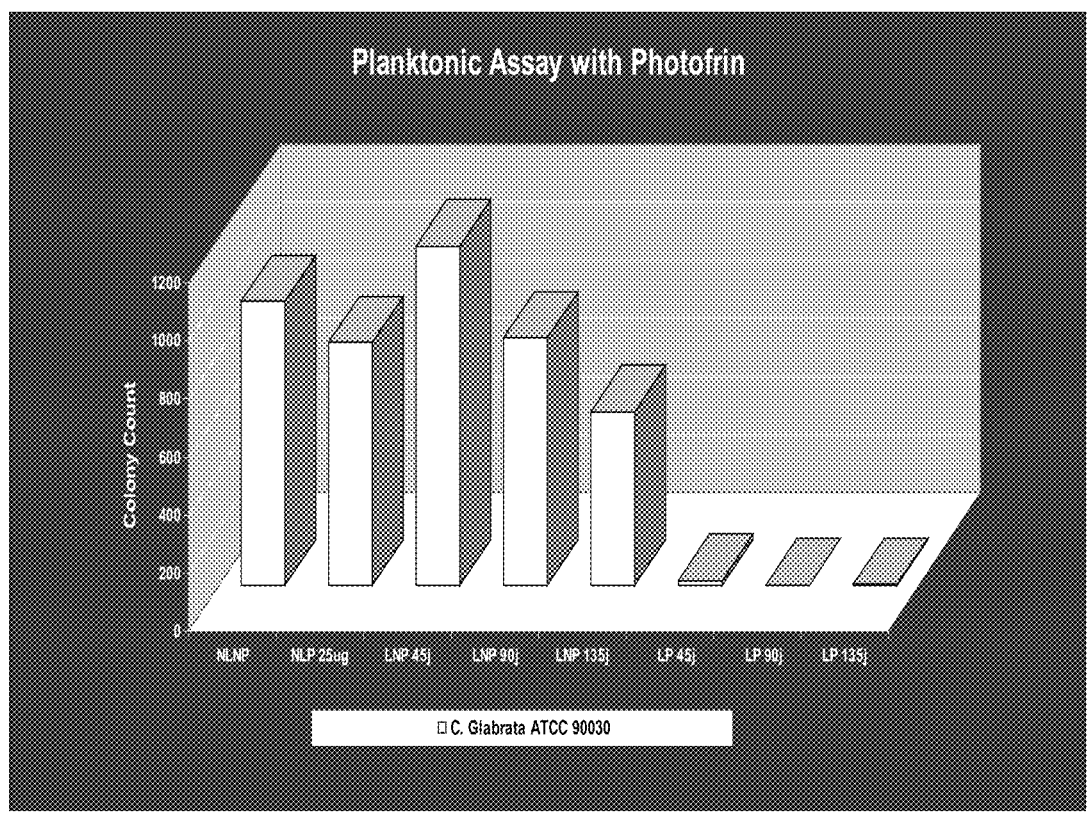
FIG. 5B shows phototoxicity of porfimer sodium and increasing 630 nm light doses on the colony forming ability of ATCC cultures of *C. glabrata*.

FIG. 5A shows the phototoxicity of porfimer sodium and increasing light dose, on colony forming ability of various ATCC Candida cultures. FIG. 5B shows phototoxicity of porfimer sodium and increasing 630 nm light doses on the colony forming ability of ATCC cultures of C. glabrata Example 3: In Vivo Evaluation of Sodium Saline Solution in Abraded Skin Wounds Infected with Staphylococcus aureus, Moraxella catarrhalis, or Haemophilus influenza This study evaluated the antimicrobial activity and local safety of porfimer sodium when applied to abraded wounds in Yorkshire pigs.

Methods:

On Day −2 of the study, pigs were anesthetized and the skin aseptically prepared. Superficial wounds were created using the tape strip method until punctate bleeding was observed. Also on Day −2, eight wounds per pig were inoculated with one of three bacterial cultures (*Haemophilus influenza*, *Moraxella catarrhalis*, or *Staphylococcus aureus*) at a concentration of $10^7$-$10^8$ CFUs per mL. There were two control sites on each side. Two control sites received bacteria and two did not receive bacteria. The wounds were covered, analgesia in the form of buprenorphine (IM, 0.03 mg/kg) was provided, and the animals were recovered from anesthesia.

On Day 0, culture swabs were collected from each wound prior to dosing. Six wounds per pig were treated with the test article and the laser light treatment. Culture swabs were collected from the test wounds 1 hour following laser light treatment and the animals were recovered from anesthesia. On Day 1, culture swabs were collected from the treated wounds and two wounds per pig were treated a second time with the test article and the laser light treatment. Culture swabs were collected from these test wounds 1 hour following laser light treatment and the animals were recovered from anesthesia. On Day 2, culture swabs were collected from each wound just prior to euthanasia.

Porfimer sodium administration: to prepare the test article, 75 mg of porfimer sodium was reconstituted with the currently FDA approved method of 31.8 mL of 0.9% sodium chloride, resulting in a stock solution of 2.5 mg/mL. Due to concerns about stability of the solution, the solution was used immediately. A 10 ml solution at a concentration of 0.3 mg/ml (300 mcg/ml), in 0.9% Sodium Chloride Injection (USP) was prepared. 300 µg of porfimer sodium was applied as a saline solution to infected wounds (except controls) and incubated for 30 minutes prior to activation. The sites were exposed to a 630 nm laser light for up to 20 minutes. The light source, a 630PDT laser. Each wound was exposed to 200 J/cm².

Figure 6:
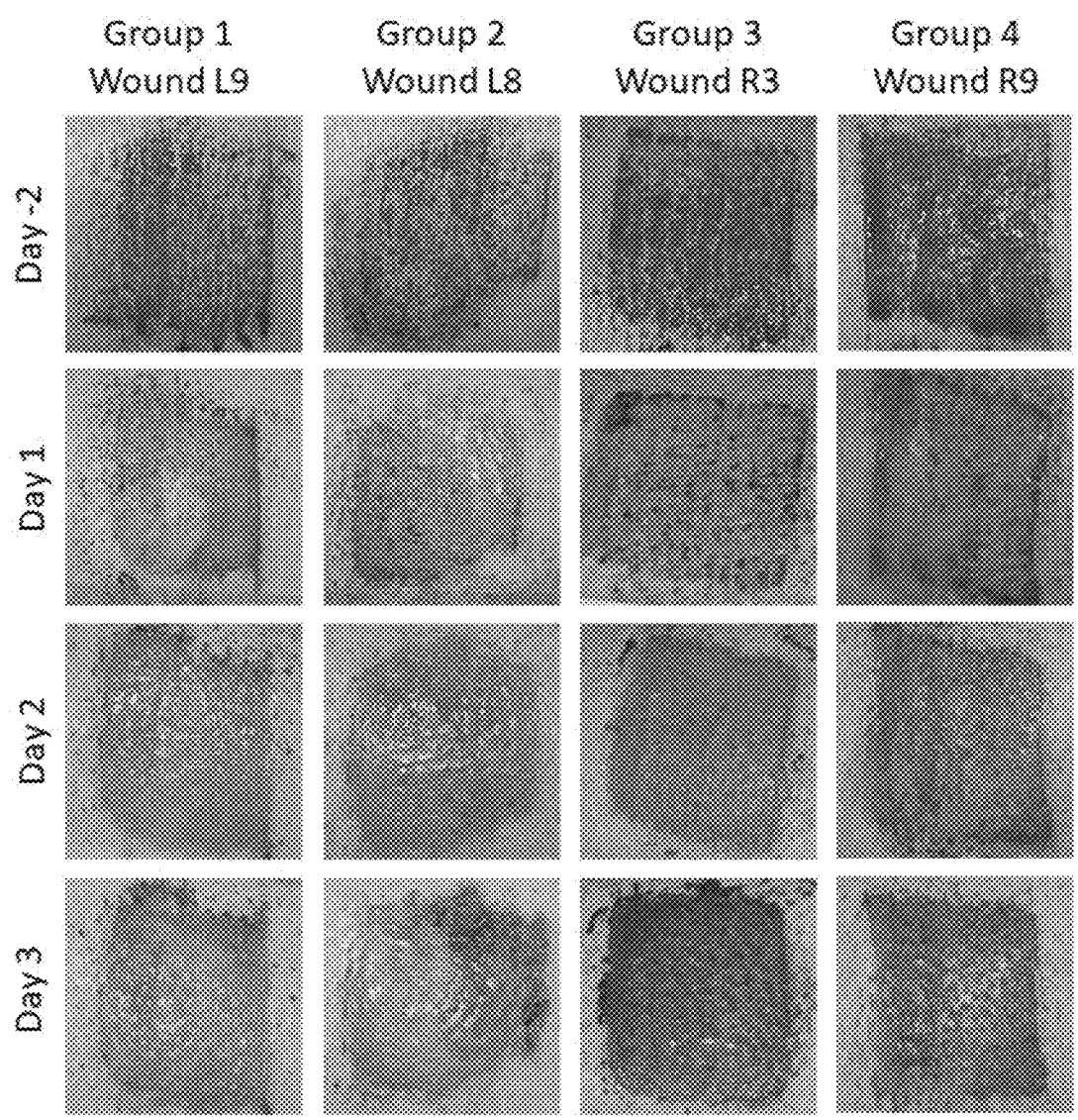
FIG. 6 shows representative wounds from the in-vivo study outlined in Example 3. Images were taken of individual wounds over the course of the study. Day-2 are newly created wounds prior to infection with bacteria. Day 1 are wounds following infection and a 48-hour incubation. Day 2 are wounds one day following first treatment, but prior to second treatment. Day 3 are wounds just prior to biopsy collections.

Results:

FIG. 6 shows representative wounds. Images were taken of individual wounds over the course of the study. Day −2 are newly created wounds prior to infection with bacteria. Day 1 are wounds following infection and a 48-hour incubation. Day 2 are wounds one day following first treatment, but prior to second treatment. Day 3 are wounds just prior to biopsy collections. The results are summarized in Table 2, below. Notably, the summary indicates the use of different formulations. Sites 1, 2, 6 and 7 include a formulation of porfimer sodium comprising a hydrogel. Sites 3 and 8 included formulations of porfimer sodium in saline, i.e., without a hydrogel. In Table 2, sites 5 and 10 represent non-infected control sites, and sites 4 and 9 represent untreated, infected controls.

TABLE 2

Comparison of Log survival per site (Log CFU/site)

| Sites | Test day | Description | Sa | Mc | Hi |
|---|---|---|---|---|---|
| 2 | 0 | Pre-treatment | $2.0 \times 10^4$ | $1.6 \times 10^4$ | 0 |
|  | 0 | 1 h-post tx | $2.9 \times 10^5$ | $2.6 \times 10^4$ | $1.2 \times 10^2$ |
|  | 1 | Pre $2^{nd}$ tx | $2.8 \times 10^5$ | $1.0 \times 10^6$ | $2.3 \times 10^3$ |
|  | 1 | 1 h-post $2^{nd}$ tx | $2.2 \times 10^4$ | $9.4 \times 10^4$ | $1.0 \times 10^4$ |
|  | 2 | Terminal | $1.2 \times 10^5$ | $5.8 \times 10^5$ | $2.0 \times 10^2$ |

TABLE 2-continued

Comparison of Log survival per site (Log CFU/site)

| Sites | Test day | Description | Sa | Mc | Hi |
|---|---|---|---|---|---|
| 7 | 0 | Pre-tx | $1.0 \times 10^3$ | NOC | $1.0 \times 10^4$ |
|  | 0 | 1 h-post tx | $6.5 \times 10^3$ | NOC | $1.3 \times 10^4$ |
|  | 1 | Pre $2^{nd}$ tx | $1.4 \times 10^6$ | $3.6 \times 10^4$ | $2.0 \times 10^4$ |
|  | 1 | 1 h-post $2^{nd}$ tx | $2.1 \times 10^5$ | $8 \times 10^1$ | $9.2 \times 10^2$ |
|  | 2 | Terminal | $1.3 \times 10^6$ | $7.4 \times 10^5$ | $5.8 \times 10^4$ |
| 1 | 0 | Pre-treatment | $1.3 \times 10^4$ | $6.2 \times 10^3$ | $8.0 \times 10^3$ |
|  | 0 | 1 h-post tx | $1.2 \times 10^4$ | $8.0 \times 10^3$ | $6.3 \times 10^3$ |
|  | 1 | 24 h post tx | $2.6 \times 10^6$ | $7.6 \times 10^5$ | $3.0 \times 10^5$ |
|  | 2 | Terminal | $1.18 \times 10^7$ | $1.0 \times 10^6$ | $1.8 \times 10^7$ |
| 6 | 0 | Pre-treatment | $2.0 \times 10^4$ | $4.0 \times 10^2$ | $3.7 \times 10^3$ |
|  | 0 | 1 h post tx | $2.6 \times 10^5$ | $2.0 \times 10^3$ | $8.4 \times 10^3$ |
|  | 1 | 24 h post tx | $1.7 \times 10^6$ | $1.1 \times 10^5$ | $3.0 \times 10^5$ |
|  | 2 | Terminal | $8.6 \times 10^4$ | $1.7 \times 10^6$ | $9.5 \times 10^4$ |
| 3 | 0 | Pre-treatment | $2.6 \times 10^4$ | $1.7 \times 10^3$ | $5.0 \times 10^5$ |
|  | 0 | 1 h post tx | $2.8 \times 10^5$ | $8.0 \times 10^2$ | $4.4 \times 10^3$ |
|  | 1 | 24 h post tx | $1.7 \times 10^4$ | $6.6 \times 10^5$ | $1.0 \times 10^2$ |
|  | 2 | Terminal | $1.8 \times 10^4$ | $3.1 \times 10^6$ | $2.0 \times 10^2$ |
| 8 | 0 | Pre-treatment | $1.9 \times 10^4$ | $3 \times 10^1$ | $1.0 \times 10^4$ |
|  | 0 | 1 h post tx | $1.5 \times 10^4$ | $5.4 \times 10^3$ | $5.9 \times 10^3$ |
|  | 1 | 24 h post tx | $2.8 \times 10^5$ | $1.1 \times 10^3$ | $4.2 \times 10^4$ |
|  | 2 | Terminal | $6.7 \times 10^4$ | $3.0 \times 10^4$ | $2.7 \times 10^4$ |
| 4 | 0 | Pre-treatment | $2.7 \times 10^4$ | $8.4 \times 10^3$ | $1.0 \times 10^5$ |
|  | 2 | Terminal | $8.1 \times 10^5$ | $7.1 \times 10^3$ | $4.6 \times 10^4$ |
| 9 | 0 | Pre-treatment | $9.7 \times 10^3$ | $2.5 \times 10^2$ | $1.1 \times 10^4$ |
|  | 2 | Terminal | $2.3 \times 10^5$ | $1.8 \times 10^4$ | $5.0 \times 10^3$ |
| 5 | 0 | Pre-treatment | NOC | NOC | NOC |
|  | 2 | Terminal | NOC | $1.0 \times 10^4$ | $8.0 \times 10^1$ |
| 10 | 0 | Pre-treatment | NOC | $1.4 \times 10^4$ | NOC |
|  | 2 | Terminal | NOC | $2 \times 10^1$ | $5.5 \times 10^2$ |

Description: 1) pre-treatment - sample taken immediately prior to application of test article; 2) 1 hour post-dose - sample taken 1 hour after the completion of the light dose delivery; 3) Pre-2nd treatment; (if given) sample taken 24 hr post 1st light dose and immediately prior to application of test article for 2nd light dose; 4) 1 h post Post 2nd treatment - sample taken at one hour after the light dose has been delivered; 5) 24 h post treatment - sample taken at 24 hours after the light treatment; 6) Terminal - sample taken at termination of the study.

Description: 1) pre-treatment—sample taken immediately prior to application of test article; 2) 1 hour post-dose—sample taken 1 hour after the completion of the light dose delivery; 3) Pre-2nd treatment; (if given) sample taken 24 hr post 1st light dose and immediately prior to application of test article for 2nd light dose; 4) 1 h post Post 2nd treatment—sample taken at one hour after the light dose has been delivered; 5) 24 h post treatment—sample taken at 24 hours after the light treatment; 6) Terminal—sample taken at termination of the study.

As expected, there were no organisms observed at the non-infected control sites (5 & 10), while the untreated control sites (4 & 9) showed growth of the selected test strains. Sites 1, 3, 6, and 8 were treated once with the laser and porfimer sodium (LPO). Sites 4, 5, 9, and 10 were not treated with the laser or porfimer sodium (NLNP). Sites 2 and 7 were treated twice with the laser and porfimer sodium test article (LPT).

Table 2 shows the average $\log_{10}$ CFU per site for each bacteria strain for Sites 2 and 7, 1 and 6, 3 and 8, 4 and 9, and 5 and 10. For Sites 2 and 7, there was a slight decrease in the average $\log_{10}$ CFU per site for each bacteria strain 1 hour after the second dose was applied, however, the average logo CFU per site increased or remained the same 24 hours later at the terminal time point. Similarly, histopathological observations showed no significant difference between treated sites and control sites. Porfimer sodium did not provide antimicrobial activity when applied to wounds inoculated with *Staphylococcus aureus*, *Moraxella catarrhalis*, or *Haemophilus influenza* in this study.

Example 4: In Vivo Evaluation of Porfimer Sodium Saline Solution in Abraded Skin Wounds with MRSA Infections This study evaluated the ability of porfimer sodium to reduce/eliminate microbial colonization and biofilm from surgical sites in a partial thickness would healing model. The study was conducted in a single female Yorkshire pig over the course of five days. A dermatome was used to create 20 partial thickness wounds. Sixteen of the wounds were infected with methicillin-resistant *Staphylococcus aureus* (MRSA), and four were designated as uninfected controls. The wounds were bandaged and the bacterial biofilm allowed to develop for 48 hours.

TABLE 3

Treatment Groups

| Treatment | Group | Number | Bacteria ($2 \times 10^6$ CFU/wound) | Light intensity ($J/cm^2$) |
|---|---|---|---|---|
| Uninfected/ Untreated | 1 | 4 | N/A | N/A |
| Infected/ Untreated | 2 | 4 | *Staphylococcus aureus* ATCC BAA 1768 | N/A |
| Infected/ porfimer sodium | 3 | 6 | *Staphylococcus aureus* ATCC BAA 1768 | 150 |
| Infected/ porfimer sodium | 4 | 6 | *Staphylococcus aureus* ATCC BAA 1768 | 200 |

Designated infected wounds were subjected to two courses of treatment with the test article at a periodicity of 24 hours. Article dose concentration of 1.0 mg/mL of porfimer sodium was prepared as described in Example 3, and used immediately, with the exception of two wounds (L6 and L7) where the test article (reconstituted porfimer sodium) was mixed 1:1 with NeilMed NasalGel.

Treatments consisted of application of the test article followed by photoactivation with one or two intensities of light, 150 $J/cm^2$ or 200 $J/cm^2$ (Table 3). Wounds were evaluated for microbial load prior to each course of treatment, immediately following the final treatment and 24 hours following the final treatment. Tissue specimens from infected and non-infected wounds were harvested for histology of biofilm formation at each treatment time point. Tissue specimens from treated wounds were harvested 24 hours following the final treatments for histology.

Results:

The results of the microbial load analysis are summarized in Table 4.

TABLE 4

Porfimer Sodium Induced aPDT on Wounds Infected with MRSA C32-101 *S. aureus* in wound swabs and tissue

| Wound | Group | WOUND SWABS (CFU/mL) | | | TISSUE BIOPSY (CFU/mm$^2$) 24 hr. after treatment 2 |
|---|---|---|---|---|---|
| | | Pre-Treat 1 | Pre-treat 2 | Immediately Post-Treat 2 | 24 hr. Post-Treat 2 | |
| L3* | 1 | 5.70E+05 | 4.90E+04 | N/A | 6.50E+02 | 1.06E+02 |
| L9 | 1 | 0.00E+00 | 0.00E+00 | N/A | 8.80E+01 | 0.00E+00 |
| R6 | 1 | 0.00E+00 | L20E+02 | N/A | 4.35E+02 | 1.09E.01 |
| R10 | 1 | 0.00E+00 | 0.00E+00 | N/A | 1.80E+01 | 5.57E+01 |
| L4 | 2 | 4.00E+03 | 1.98E+05 | N/A | 9.00E+02 | 4.58E+03 |
| L8 | 2 | 3.40E+04 | 5.90E+00 | N/A | 3.15E+03 | 2.42E+03 |
| RI | 2 | 1.86E+05 | 3.86E+06 | N/A | 2.00E+03 | 8.26E+02 |
| R2 | 2 | 1.11E+05 | 4.14E+06 | N/A | 1.05E+04 | 8.06E+02 |
| L1 | 3 | 6.30E+05 | 8.80E+04 | N/A | 1.14E+04 | 4.28E+03 |
| L7 | 3 | 1.94E+06 | 1.06E+03 | 7.40E+04 | 1.60E+03 | 1.08E+04 |
| R3 | 3 | 3.03E+06 | 6.60E+05 | 1.92E+05 | 1.17E+04 | 1.57E+04 |
| R7 | 3 | 2.88E+05 | 2.74E+03 | N/A | 3.50E+02 | 2.78E+03 |
| R8 | 3 | 4.00E+03 | 4.20E+04 | N/A | 2.65E+03 | 4.73E+03 |
| L5 | 3 | 5.40E+04 | 3.45E+05 | 6.16E+03 | 4.30E+03 | 1.05E+04 |
| L2 | 4 | 2.42E+05 | 1.40E+04 | 4.20E+04 | 1.55E+03 | 6.27E+03 |
| L6* | 4 | 0.00E+00 | 1.74E+03 | 1.44E+05 | 1.15E+03 | 3.44E+03 |
| L10 | 4 | 2.60E+04 | 2.00E+04 | N/A | 1.79E+02 | 5.47E+02 |
| R4 | 4 | 2.29E+06 | 1.50E+06 | 2.80E+04 | 1.75E+03 | 1.11E+03 |
| R5* | 4 | 0.00E+00 | 1.44E+06 | N/A | 3.15E+03 | 8.35E+03 |
| R9* | 4 | 0.00E+00 | 7.60E+00 | N/A | 2.31E+02 | 3.36E+03 |

Group 1 = uninfected controls;
Group 2 = infected/untreated controls,
Group 3 = 150 J/cm2 treatment; and
Group 4 = 200 J/cm2 treatment;
*Data for wounds R3, L6, R5, and R9 were excluded from determination of results.

The mean microbial loads from the wound swabs (Table 4) is depicted in Table 5, below. The calculated mean microbial load in Group 1. The values for Group 4 do not include the data from wounds L6, R5, and R9 in which MRSA was not detected Pretreat 1 swabs.

TABLE 5

Mean Microbial Loads of Wound Specimens

| Specimen | Group 1 | | | Group 2 | | | Group 3 | | | Group 4 | | |
|---|---|---|---|---|---|---|---|---|---|---|---|---|
| | N | Mean[1] | SEM | N | Mean[1] | SEM | N | Mean[1] | SEM | N | Mean[1] | SEM |
| Pretreat 1 (swab) | 3 | 0.00E+00 | 0.00E+00 | 4 | 8.38E+04 | 4.09E+04 | 6 | 9.91E+05 | 5.01E+05 | 3 | 8.53E+05 | 7.21E+05 |
| Pretreat 2 (swab) | 3 | 4.00E+01 | 4.00E+01 | 4 | 2.05E+06 | 1.13E+06 | 6 | 1.90E+05 | 1.08E+05 | 3 | 5.11E+05 | 4.94E+05 |
| Posttreat 2 (swab) | 3 | 1.80E+02 | 1.29E+02 | 4 | 4.14E+03 | 2.17E+03 | 6 | 5.33E+03 | 2.04E+03 | 3 | 1.16E+03 | 4.94E+02 |
| Tissue | 3 | 2.22E+01 | 1.70E+01 | 4 | 2.16E+03 | 8.91E+02 | 6 | 8.13E+03 | 2.04E+03 | 3 | 2.64E+03 | 1.82E+03 |

The mean microbial loads for Group 1 (uninfected controls) swabs increased over the course of the study from no detectable MRSA prior to treatment to 40 CFU/swab following the first treatment and 180 CFU/swab following the second treatment. The presence of MRSA, albeit at low amounts, in these control specimens is likely due to cross-contamination of the wounds as a result of the challenges of maintaining aseptic regions on the surface of the animal during the study.

The mean microbial loads for Group 2 (infected, untreated) swab specimens increased 24.5-fold in pre-treatment 2 and variable amounts in subsequent sampling.

The mean microbial loads in the Group 3 (infected, porfimer sodium, 150 J/cm$^2$) and Group 4 (infected, porfimer sodium, 200 J/cm$^2$) wound swabs decreased by 5.2 and 1.7-fold respectively, following porfimer sodium treatment 1 on SD1 (Study Day 1) to SD2 (Study Day 2). An additional 36- and 250-fold decrease was observed following Treatment 2; and an overall 186-fold and 735-fold decrease was observed over the course of treatment from SD1 (Study Day 1) to SD3 (Study Day 3), respectively.

In summary, microbial load results demonstrated a decrease in MRSA colony forming units in swabs from treated wounds following the first application of porfimer sodium followed by 630 nm illumination compared to untreated infection controls. The observed decrease was 186-fold for treatment Group 3, and 735-fold for treatment Group 4. Both of these are larger than the observed decrease for the untreated Group 2 wounds, which exhibited a decrease in bacterial load of 20-fold. This decrease in the untreated group must take into consideration wound physiology such as antimicrobial peptides and other known factors.

The data shows inconsistency in the results when porfimer sodium mixed in saline, is applied directly to the infected wounds. Multiple difficulties were presented using this application method. First and foremost, applying the saline mixture presented difficulties in maintaining a consistent amount of the drug on the infected wound. As a liquid the solution simply flowed off of the wound. This presented an application and consistency of drug delivery issue but also may have contributed to cross contamination of wounds and the surrounding skin. The use of the NeilMed nasal gel did not provide an improvement.

A significant reduction of antimicrobial efficacy is noted in the wounds which have biofilm and are treated with photodynamic therapy compared to planktonic cultures treated in the same manner. This clearly demonstrates the concept that biofilm infections are difficult to eradicate despite the data demonstrating the ability of photodynamic therapy to do so in planktonic cultures. Thus, prompting the development of formulations designed to increase the drug delivery and enhanced permeation into exopolysaccharide matrix which encases the bacteria in the in vivo wound model.

Example 5: Porfimer Sodium Formulations 1-6

The application of successful in vitro work with conventional porfimer sodium solutions to in vivo studies proved extremely challenging. Overall, the in vivo studies described in Examples 2 and 3 showed that antimicrobial photodynamic therapy with conventional FDA approved porfimer sodium preparations gave negative or mixed results in models of abraded wounds, despite promising result in vitro (see Example 1). Similarly, formulations containing conventional reconstituted porfimer sodium, such as mixed with thickening agent, did not improve in vivo efficacy (Example 3). Another problem identified in the in vivo trial described in Example 3 was potential drying of the wound. Further, it was hypothesized that poor skin permeation of the porfimer sodium was effected in saline solution. Conventional FDA approved porfimer sodium preparations have poor stability once reconstituted into solution. As such, reconstituted porfimer sodium must be used immediately, or within 24 hours, upon reconstitution.

The compositions of more complex and advanced porfimer sodium (0.2% w/w) formulations Formulation 1-Formulation 6 prepared are outlined in Table 6 below.

TABLE 6

Topical Porfimer Sodium Formulations 1-6

| | | % w/w | | | | | |
|---|---|---|---|---|---|---|---|
| | | Water-based Formulation | Anhydrous Formulations | | | | |
| Ingredient | Functionality | 1 | 2 | 3 | 4 | 5 | 6 |
| Porfimer sodium | API | 0.2 | 0.2 | 0.2 | 0.2 | 0.2 | 0.2 |
| Phosphate buffered saline | Buffer | 20.0 | | | | | |

TABLE 6-continued

Topical Porfimer Sodium Formulations 1-6

| | | % w/w | | | | | |
|---|---|---|---|---|---|---|---|
| | | Water-based Formulation | Anhydrous Formulations | | | | |
| Ingredient | Functionality | 1 | 2 | 3 | 4 | 5 | 6 |
| Propylene glycol SR | Preservative; Humectant; Stabilizing Agent; Solubilizing Agent; Permeation Enhancer | 37.3 | 57.3 | 57.3 | 30.0 | 20.0 | 20.0 |
| Polyethylene glycol 400 SR | Solvent; Permeation Enhancer | | | | | 57.8 | 20.0 |
| Polyethylene glycol 300 LA | Solvent; Permeation Enhancer | 20.0 | 20.0 | | 46.8 | | |
| Diethylene glycol monoethyl ether | Solubilizing Agent; Permeation Enhancer | | | 20.0 | | | 22.8 |
| Polysorbate 80 | Emulsifier; Solubilizing Agent; Permeation Enhancer; Surfactant | 2.0 | 2.0 | 2.0 | 2.0 | 2.0 | 2.0 |
| Glycerin | Preservative; Emollient; Humectant; Solvent | 15 | 15 | 15 | 15 | 15 | 15 |
| Benzyl alcohol | Solubilizing Agent; Preservative | 2.0 | 2.0 | 2.0 | 2.0 | 2.0 | 2.0 |
| Phenoxy ethanol | Preservative/ Antioxidant | 1.0 | 1.0 | 1.0 | 1.0 | 1.0 | 1.0 |
| Hexylene glycol | Solvent; Permeation Enhancer | 1.0 | 1.0 | 1.0 | 1.0 | 1.0 | 1.0 |
| Hydroxy propyl cellulose | Emulsifying Agent; Stabilizing Agent; Gelling agent | 1.5 | 1.5 | | | | |
| Carbomer | Emulsifying Agent; Stabilizer; Rheology Modifier; Gelling Agent | | | 1.5 | 2.0 | | |
| Lecithin | Emollient; Emulsifying Agent; Solubilizing Agent | | | | | 1.0 | |
| Stearyl alcohol | Bodifying agent | | | | | | 1.0 |
| Polyethylene glycol 4000 | Solvent; Surfactent | | | | | | 15.0 |

Example 6: Stability and Skin Permeation Studies on Formulations 1-5

Stability Studies

The stability of porfimer sodium formulations 1 through 5 were tested. Each formulation was tested for physical and chemical stability. Physical testing includes appearance (visual description and color, of the product), pH and microscopy. Chemical testing includes, assay (% LC) and impurities, specifically looking for degradation products of porfimer sodium. Specific impurities/degradation products analyzed for detection by HPLC retention time include hematoporphyrin (HP) and hydroxyvinyl deuteroporphyrin (HVD) (isomers 1 and 2) which are hydrolysis products of porfimer sodium and protoporphyrin (PP), which is a dehydration product. The total impurities is an accumulation of these impurities.

Environmental Chambers are maintained at the following condition temperature (° C.) and relative humidity (RH): Long term storage: 25±2° C./60±5% RH. Refrigerated: 5±3° C. Accelerated storage: 40±2° C./75±5% RH. The results are summarized in FIG. 9 and Table 7 below.

TABLE 7

| | | | Photofrin Sodium | | | | | |
|---|---|---|---|---|---|---|---|---|
| Formulation | Timepoint | Condition | Assay (%) | Hp | HvD1 | HvD2 | Pp | Total impurities (% by HPLC) |
| 1 | T0 (Initial) | RT | 104.4 | 2.25 | 2.40 | 7.00 | 4.32 | 15.97 |
| | T2wk | 5° C. | 109.5 | 2.75 | 2.57 | 7.69 | 4.34 | 17.35 |
| | | 25° C./60% RH | 109.5 | 3.22 | 2.88 | 8.07 | 4.56 | 18.73 |
| | | 40° C./75% RH | 104.5 | 5.52 | 4.29 | 9.19 | 4.36 | 23.36 |
| | T4wk | 5° C./60% RH | 108.9 | 2.22 | 2.28 | 6.91 | 3.59 | 15.01 |
| | | 25° C./60% RH | 109.7 | 3.24 | 2.94 | 7.69 | 4.03 | 17.91 |
| | | 40° C./75% RH | 95.8 | 6.28 | 4.69 | 9.19 | 4.19 | 24.35 |
| 2 | T0 (Initial) | | 85.0 | 1.52 | 1.62 | 5.21 | 3.50 | 11.85 |
| | T2wk | 5° C. | 91.8 | 1.79 | 1.75 | 5.99 | 3.80 | 13.33 |
| | | 25° C./60% RH | 81.3 | 1.82 | 1.59 | 5.44 | 3.41 | 12.26 |
| | | 40° C./75% RH | 84.1 | 2.91 | 1.75 | 5.81 | 3.33 | 13.79 |
| | T4wk | 5° C./60% RH | 93.2 | 1.61 | 1.31 | 5.34 | 3.23 | 11.50 |
| | | 25° C./60% RH | 91.6 | 1.88 | 1.40 | 5.24 | 3.29 | 11.81 |
| | | 40° C./75% RH | 80.7 | 3.32 | 1.85 | 5.85 | 3.21 | 14.24 |

TABLE 7-continued

| | | | Photofrin Sodium | | | | | |
|---|---|---|---|---|---|---|---|---|
| Formulation | Timepoint | Condition | Assay (%) | Hp | HvD1 | HvD2 | Pp | Total impurities (% by HPLC) |
| 3 | T0 (Initial) | | 94.0 | 2.15 | 2.02 | 6.10 | 3.61 | 13.88 |
| | T2wk | 5° C. | 100.6 | 2.55 | 2.03 | 6.56 | 3.86 | 15.00 |
| | | 25° C./60% RH | 95.2 | 2.81 | 2.00 | 6.45 | 3.74 | 15.00 |
| | | 40° C./75% RH | 89.5 | 4.89 | 2.34 | 6.94 | 3.25 | 17.41 |
| | T4wk | 5° C./60% RH | 104.8 | 2.26 | 1.57 | 6.10 | 3.49 | 13.42 |
| | | 25° C./60% RH | 93.5 | 2.81 | 1.66 | 5.62 | 3.03 | 13.11 |
| | | 40° C./75% RH | 79.1 | 4.91 | 2.10 | 5.66 | 3.00 | 15.67 |
| 4 | T0 (Initial) | | 80.7 | 1.40 | 1.56 | 4.90 | 3.12 | 10.98 |
| | T2wk | 5° C. | 90.4 | 1.64 | 1.66 | 5.77 | 3.53 | 12.60 |
| | | 25° C./60% RH | 84.2 | 1.70 | 1.62 | 5.38 | 3.20 | 11.90 |
| | | 40° C./75% RH | 74.3 | 2.42 | 1.66 | 5.78 | 2.57 | 12.42 |
| | T4wk | 5° C./60% RH | 87.0 | 1.40 | 1.17 | 4.97 | 2.88 | 10.42 |
| | | 25° C./60% RH | 84.3 | 1.65 | 1.24 | 4.72 | 2.78 | 10.38 |
| | | 40° C./75% RH | 65.9 | 2.23 | 1.37 | 4.08 | 2.52 | 10.20 |
| 5 | T0 (Initial) | | 97.7 | 1.93 | 1.94 | 5.96 | 3.88 | 13.71 |
| | T2wk | 5° C. | 101.5 | 2.22 | 2.17 | 7.02 | 4.37 | 15.78 |
| | | 25° C./60% RH | 99.9 | 2.52 | 2.11 | 6.55 | 3.97 | 15.15 |
| | | 40° C./75% RH | 105.4 | 3.03 | 1.92 | 6.77 | 4.23 | 15.95 |
| | T4wk | 5° C. | 101.10 | 2.02 | 1.27 | 5.69 | 3.30 | 12.28 |
| | | 25° C./60% RH | 104.1 | 2.43 | 1.54 | 6.16 | 3.68 | 13.80 |
| | | 40° C./75% RH | 102.4 | 3.07 | 1.77 | 6.45 | 3.93 | 15.21 |

As shown in Table 7, formulations 3 and 5 were physically and chemically stable for 4 weeks at 5° C., 25° C./60% RH and 40° C./75% RH except for formulation 1 that shows more than 24% impurities at 40° C. This was a surprising and unexpected result, given that porfimer sodium is only stable for 24 hours when reconstituted with saline.

Example 7: Skin Permeation Studies

A study was completed to show the ability of the formulation to deliver the drug into human skin in an in vitro setting, while retaining the API within the appropriate skin layers. The study design parameters is shown in Table 8 below.

TABLE 8

Skin Permeation Study Groups

| Formulations | Porfimer Sodium Concentration | Numbers of Donors | Replicates | Formulation Dose Volume (μL) |
|---|---|---|---|---|
| Formulation 2 | 0.2% w/w | 1 | 5 | 7.8 |
| Formulation 3 | 0.2% w/w | 1 | 5 | 7.8 |
| Formulation 4 | 0.2% w/w | 1 | 5 | 7.8 |
| Formulation 5 | 0.2% w/w | 1 | 5 | 7.8 |

In this experiment, TEWL for each diffusion cell would was measured and recorded before test article applications. A range of not more than 25 g/m2/h will be acceptable for this study. An automated in-line flow through diffusion cell system (PermeGear Collector FC 33, Version 3.1) was used to assess drug in the skin permeation experiment. Test articles were uniformly dispensed onto the skin tissue surface using a positive displacement pipette, set to deliver 7.8 μL. The study was performed under dark environment and closed to ambient conditions. Fractions were collected at intervals as indicated in the protocol for up to 24-hour time point. Precautions should be taken to prevent exposure of light in samples. Fractions were collected immediately capped and stored in aluminum foil at −20° C. At the end of the testing time, the surface of the tissue was cleaned under dark environment, with 1 dry cotton swab, 1 wet cotton swab in wash solvent (Hexane: Acetonitrile 1:9 v/v), and 1 dry cotton swab followed by three consecutive tape strips. The swabs and the tape strips were analyzed upon request. The washed and tape stripped skin was placed on aluminum foil with dermis side down and will be processed in a dark environment. The samples were placed in an oven set at 60° C. for approximately 2.0 minutes. Tweezers were used to separate the epidermis from the dermis. The separated samples were placed in respective pre-weighed labelled vials and weight of tissues were recorded.

Epidermal and dermal samples were processed and homogenized while maintaining a dark environment using the following protocol: 500 μL of homogenizing mixture, Water: Acetonitrile, 1:1 (v/v), was added to the labelled tubes containing the skin samples. The dermis is homogenized at 10,000 RPM, 4×30 seconds, 45 seconds pause period. The epidermis is then homogenized at 10,000 RPM, 2×30 seconds, 45 seconds pause period. After homogenization is completed, 1000 μL of acetonitrile is added, vortexed briefly, then sonicated for 10 minutes in water bath. The vials were centrifuged and supernatant will be used for mass spectrometry analysis. The following samples were analyzed for drug content: Receptor solution samples at different time-points; skin samples (epidermis and dermis for each cell at the final time point), tape strips and cotton swabs analyzed for mass balance determination. The permeation profile of each drug formulation into the receiving fluid and permeation of each drug formulation into the epidermis and dermis at the final time point were calculated.

Figure 9:
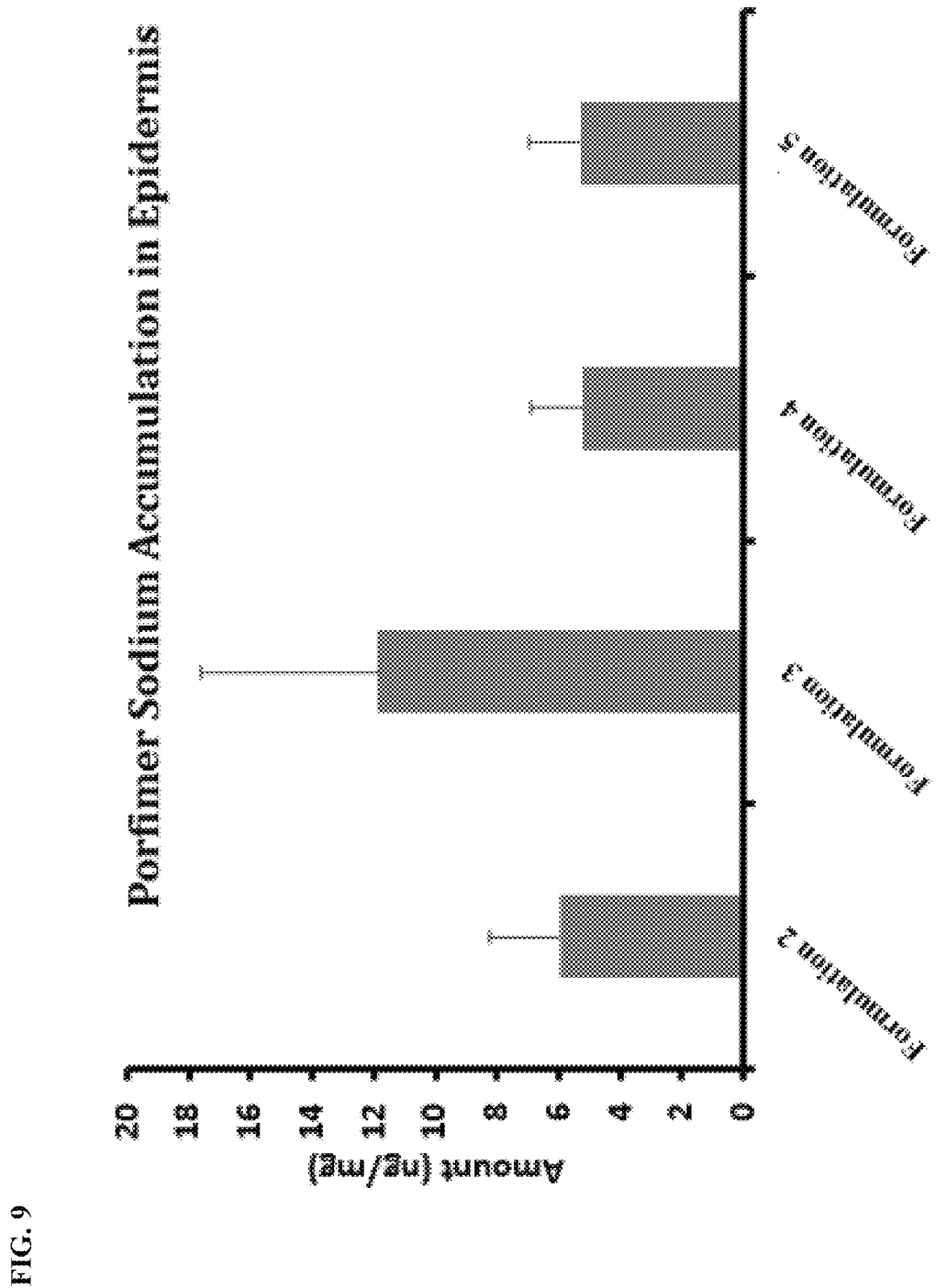
FIG. 9 shows porfimer sodium accumulation in epidermis for formulations Formulation 2, Formulation 3, Formulation 4, and Formulation 5 in the stability studies outlined in Example 7.
Figure 10:
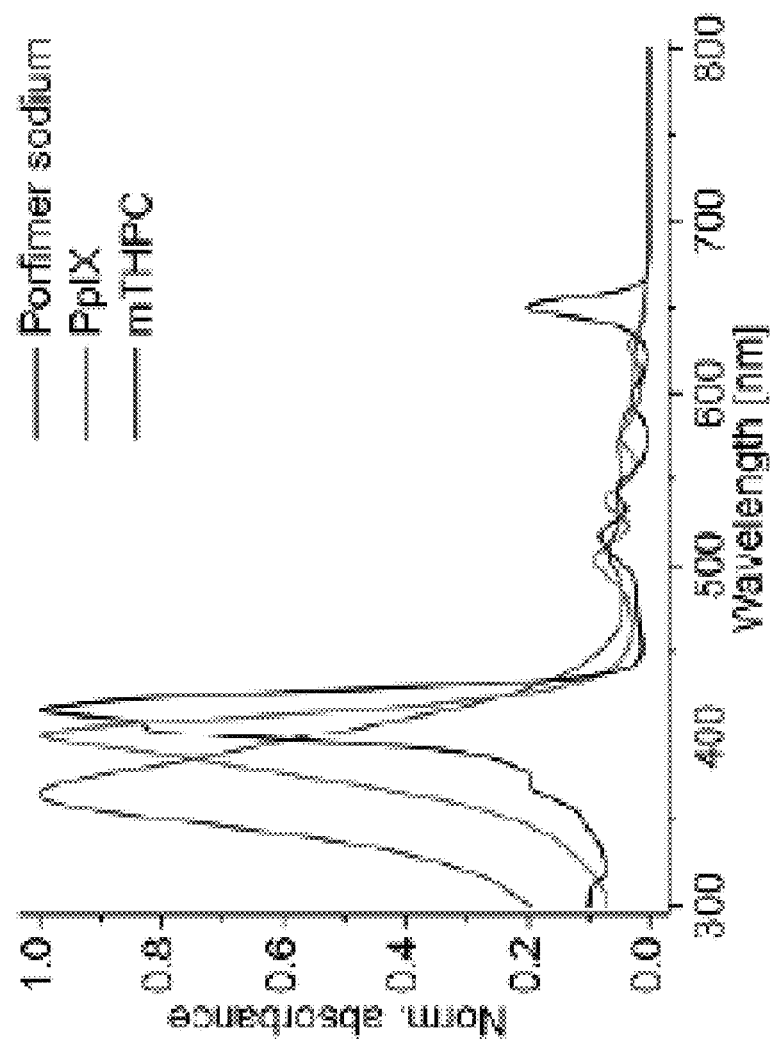
FIG. 10 shows the wavelength active range of porfimer sodium, PpIX and mTHPC.
Figure 11:
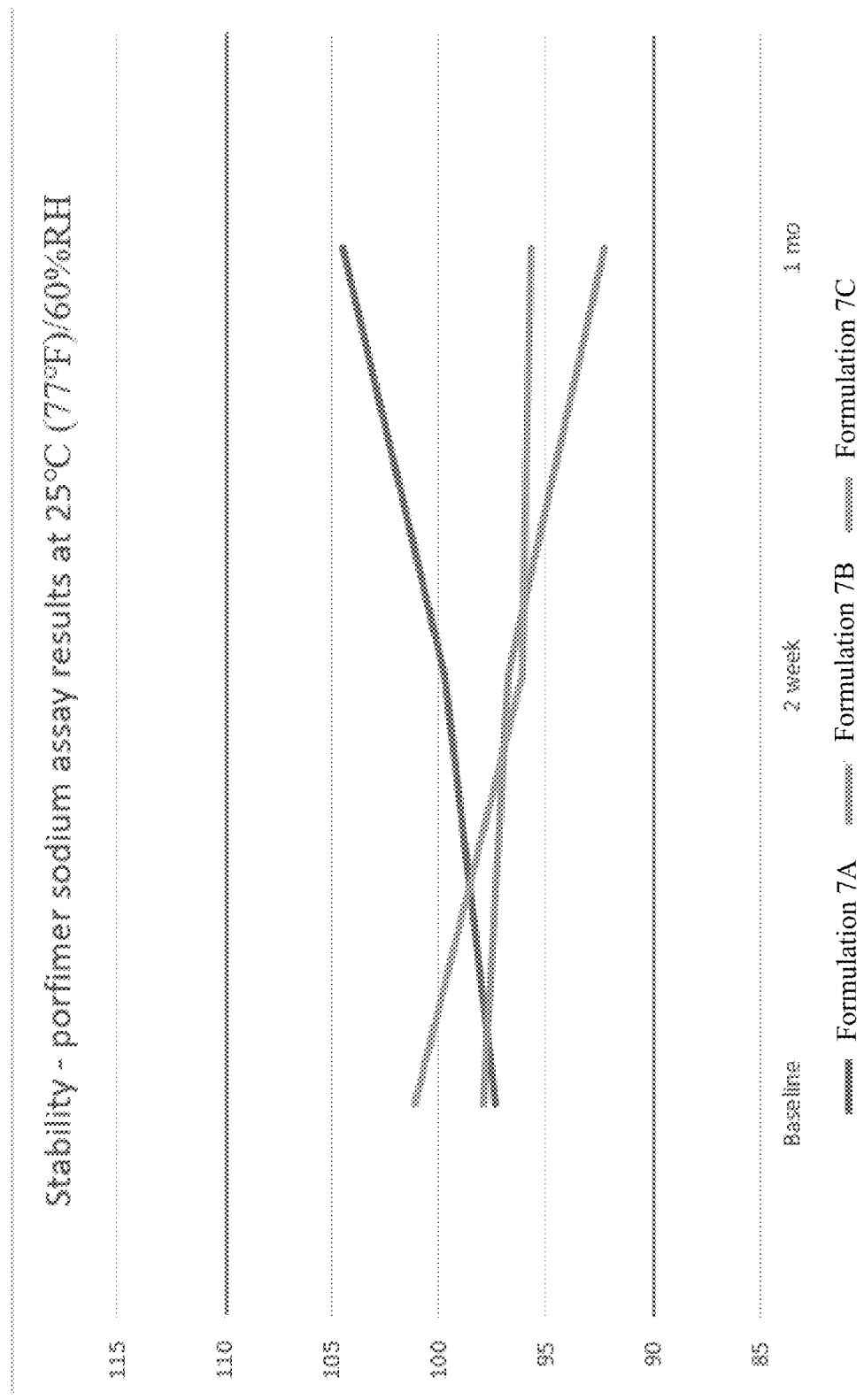
FIG. 11 shows the results of stability tests for formulations 7A, 7B, and 7C at 25° C./60% RH.
Figure 12:
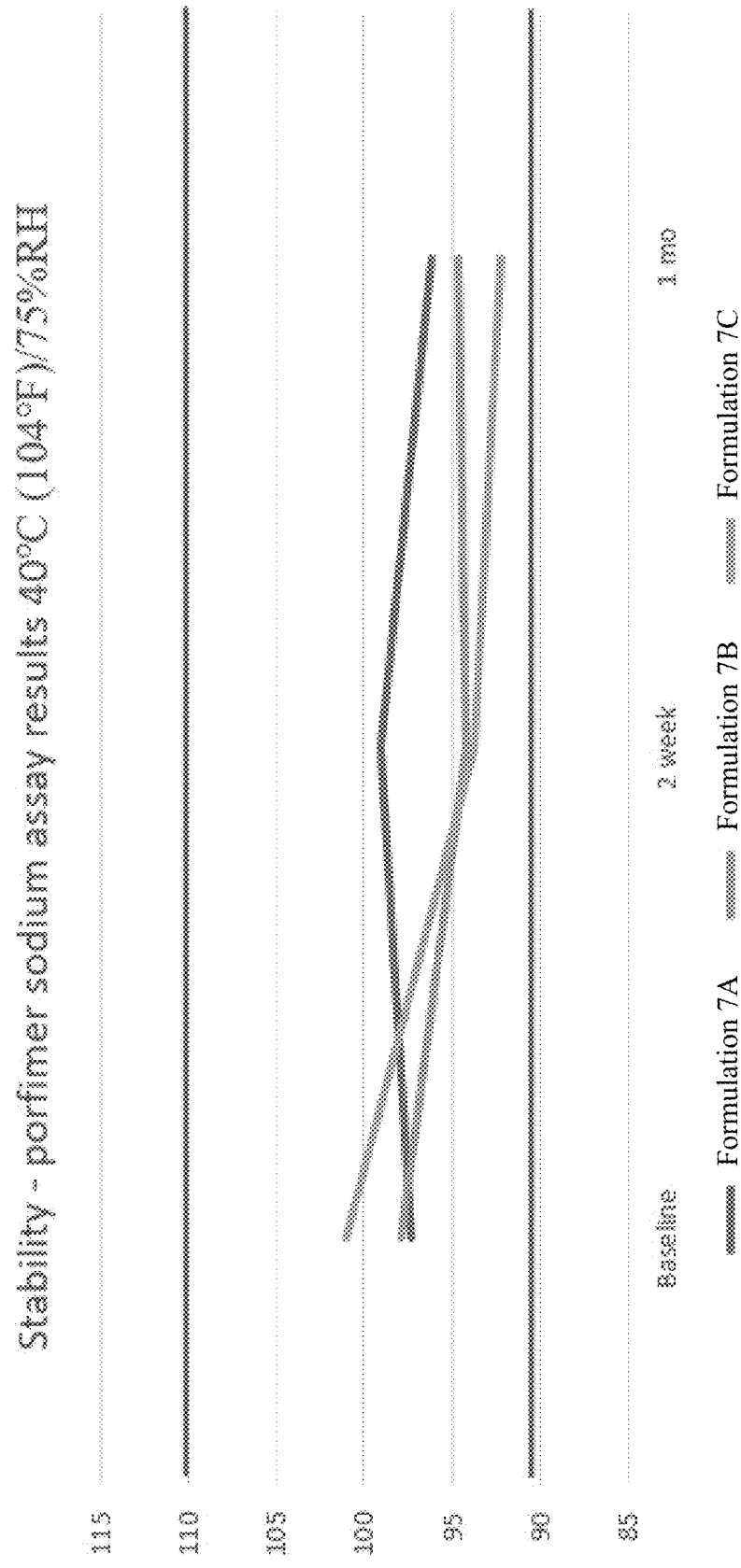
FIG. 12 shows the results of stability tests for formulations 7A, 7B, and 7C at 40° C./75% RH.
Figure 13:
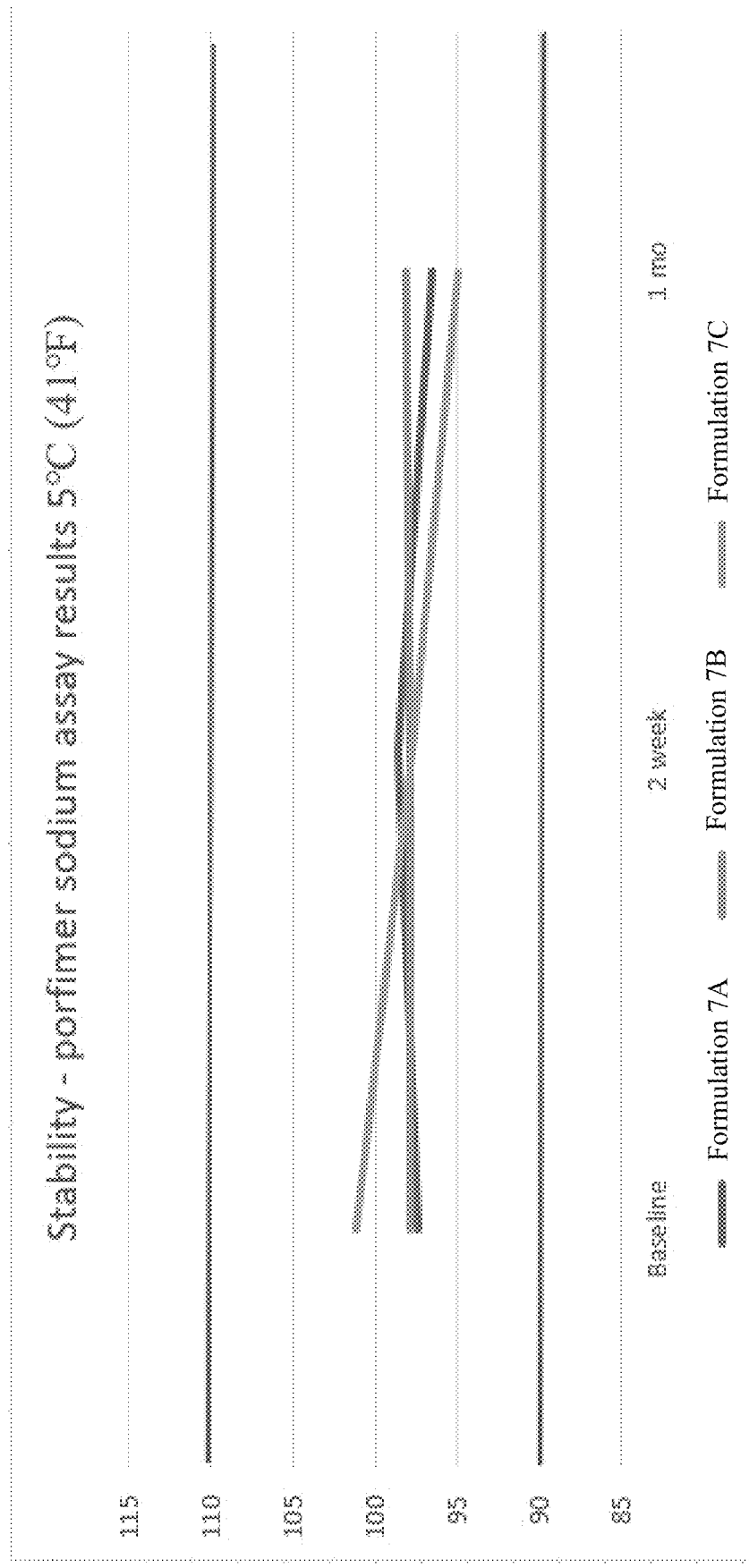
FIG. 13 shows the results of stability tests for formulations 7A, 7B, and 7C at 5° C.
Figure 14:
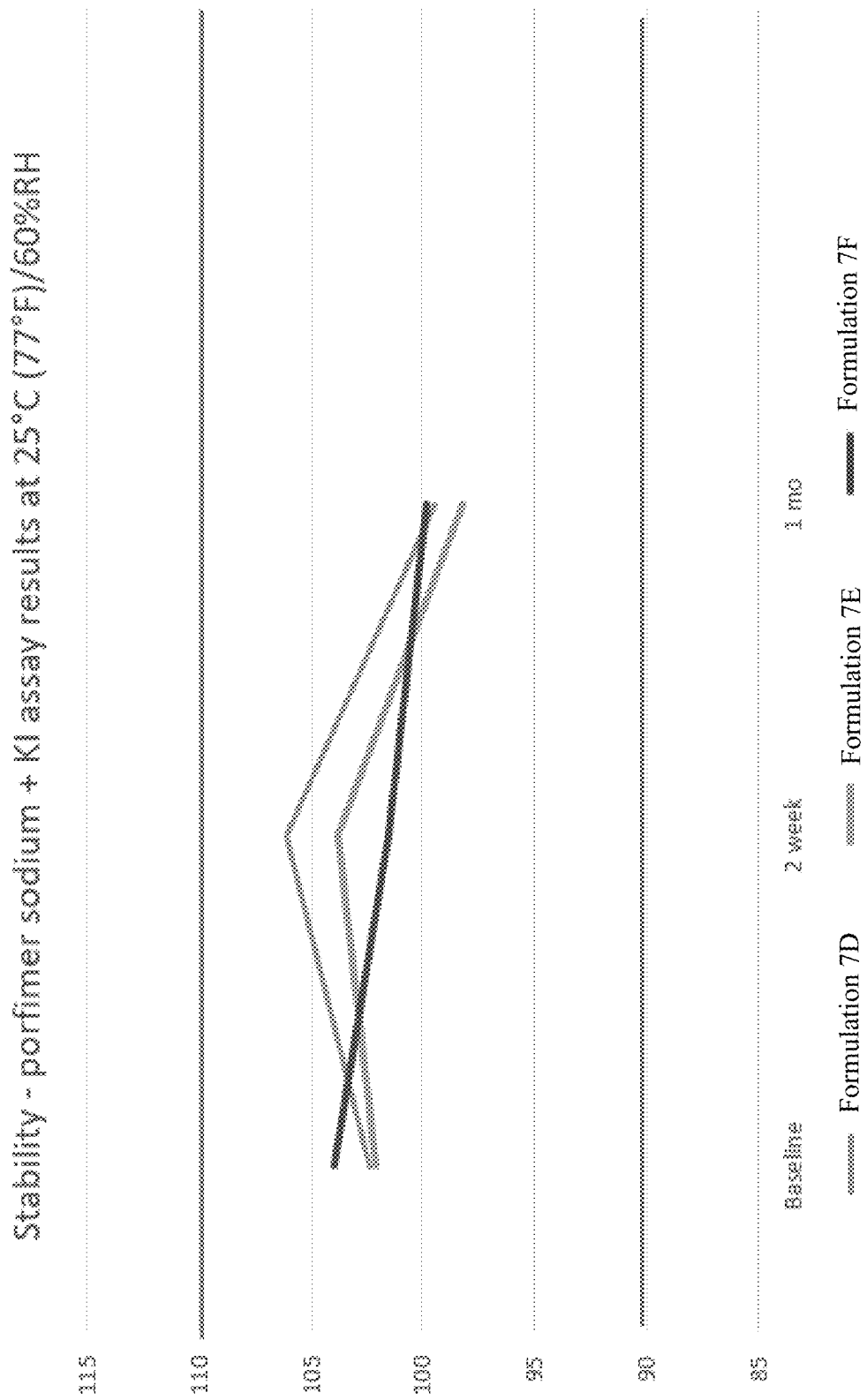
FIG. 14 shows the results of stability tests for formulations 7D, 7E, and 7F at 25° C./60% RH.
Figure 15:
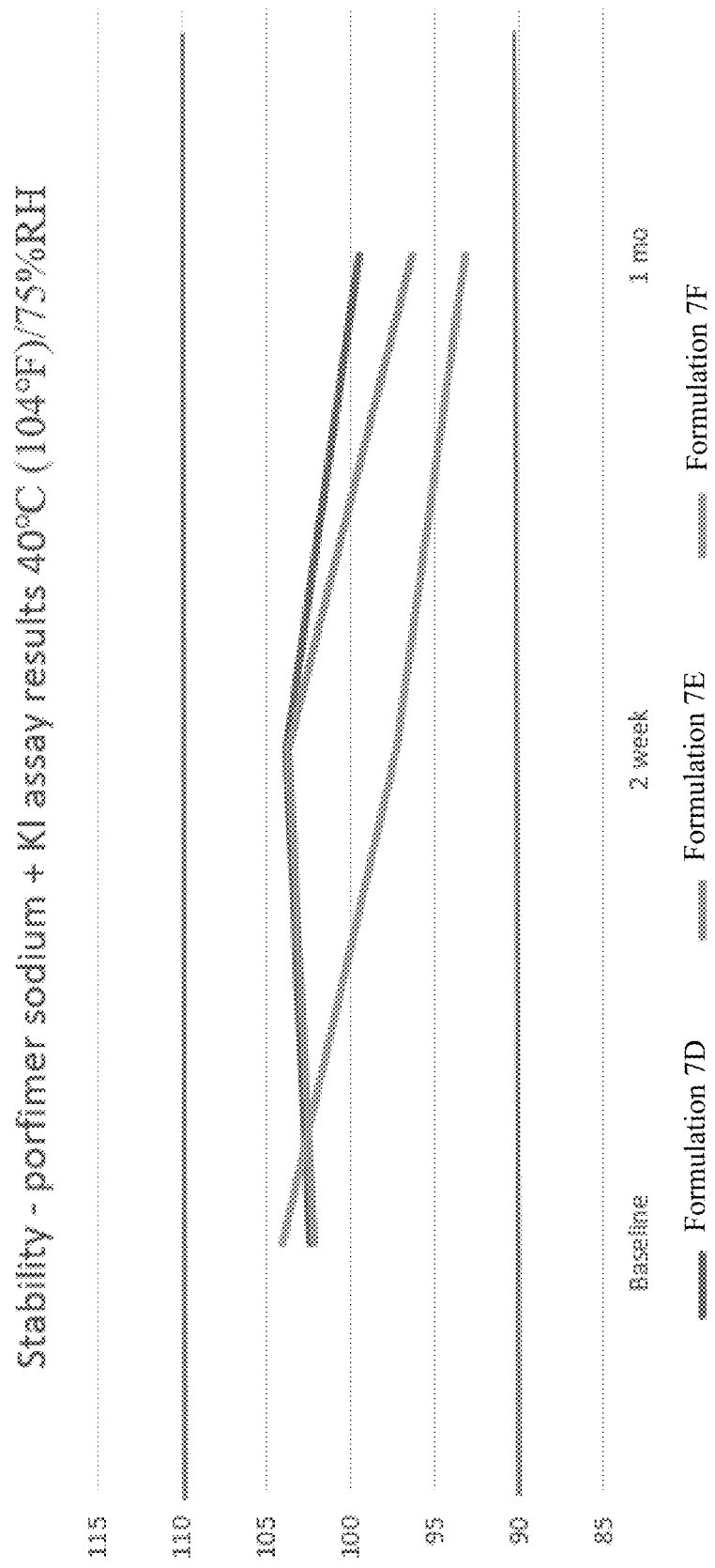
FIG. 15 shows the results of stability tests for formulations 7D, 7E, and 7F at 40° C./75% RH.
Figure 16:
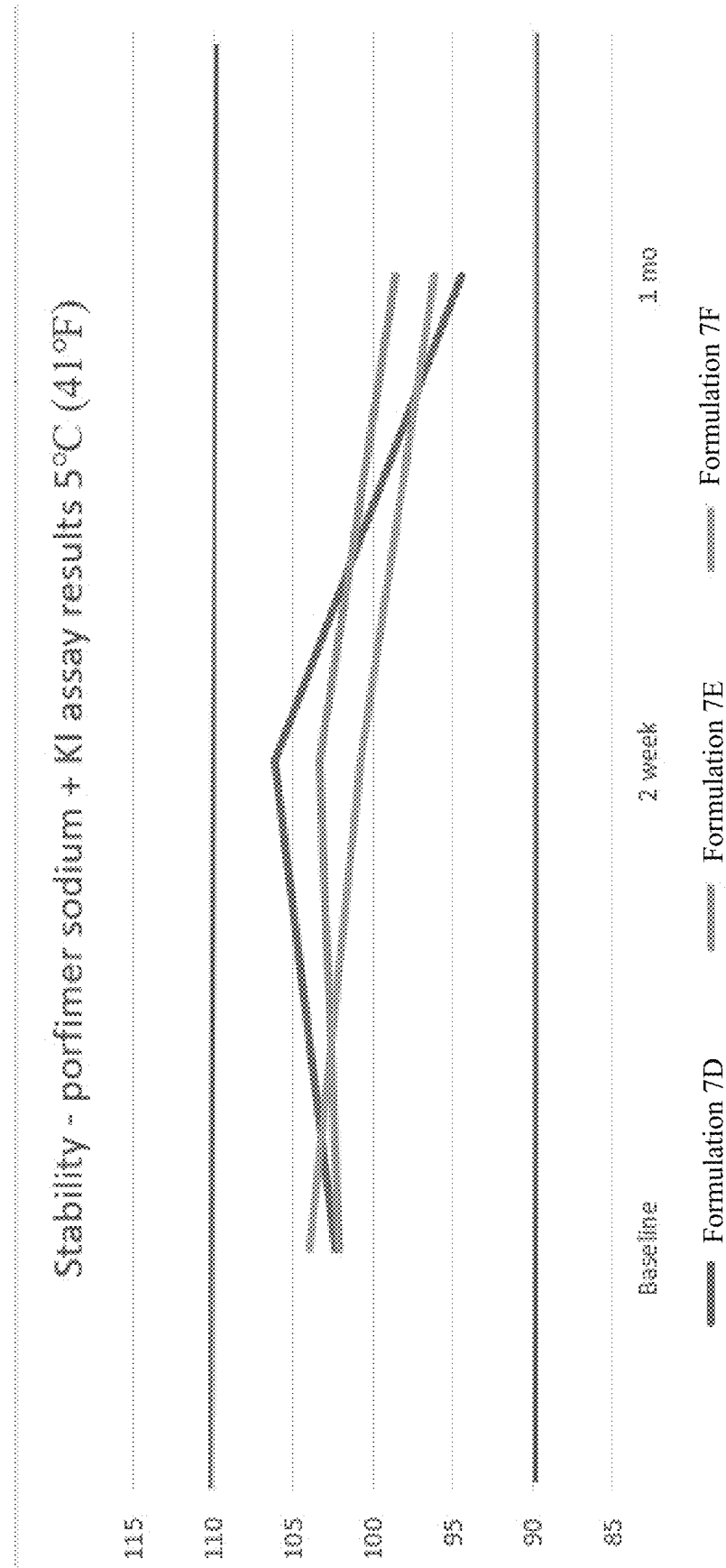
FIG. 16 shows the results of stability tests for formulations 7D, 7E, and 7F at 5° C.

Results:

Skin retention tests showed that porfimer sodium permeation was predominantly found in the epidermal layers of the skin 24 hours post application (see FIG. 9 and Table 9). No formulations showed porfimer sodium permeation in the receptor fluid.

TABLE 9

In vitro Human Skin Permeation of Porfimer Sodium

| Formulation | Applied dose (mg) | Applied API Amt (μg) | Epidermal Avg (ng/mg) | SD | % API in epidermis |
|---|---|---|---|---|---|
| 2 | 7.8 | 15.6 | 6.00 | 2.21 | 0.0218 |
| 3 | 7.8 | 15.6 | 11.85 | 5.77 | 0.0481 |
| 4 | 7.8 | 15.6 | 5.20 | 1.68 | 0.0183 |
| 5 | 7.8 | 15.6 | 5.31 | 1.68 | 0.0218 |

Out of the formulations tested, Formulation 3 shows higher epidermal retention at 0.0481% followed by Formulation 2, Formulation 5 and Formulation 4, at 0.0218% and 0.0183% respectively. It is for this reason that Formulation 3 was chosen as the delivery vehicle to be tested further on wounds, in which the epidermis and papillary dermis are removed to mimic a partial thickness wound to be examined as described in Example 8 below.

From a safety/efficacy standpoint this study is important as it shows the formulations can deliver the active ingredient into the skin deep enough to be available to the bacteria in the skin without going below the dermal layers.

Example 8: In Vivo Evaluation of Formulated Porfimer Sodium (Formulation 3) in Abraded Skin Wounds with MRSA Infections Further in vivo experiments were conducted to test the efficacy of Formulation 3 formulation in treating infections of methicillin-resistant *Staphylococcus aureus* (MRSA-ATCC 1768).

Methods:

A dermatome was used to create 20 partial thickness wounds on a Yorkshire pig according to the protocol described in Example 4. Thirteen wounds were separated into five groups as shown in Table 10 below. Group 1 was an uninfected, untreated control. Group 2 was an infected, untreated control. Groups 3-5 were each infected and treated with Formulation 3 and irradiated with 200 J/cm² of light, where the Formulation 3 composition was allowed to penetrate the wound for 1 h, 2 h, and 4 h for Groups 3, 4, and 5, respectively. A 630 nm laser was used for treatment. The treated wounds were swabbed at 1 hour post treatment and 24 hours post treatment, and biopsies obtained for histology measurements.

TABLE 10

Treatment Groups

| Treatment | Group (n) | Wounds | Bacteria ($10^6$ to $10^7$ CFU/wound) | Light intensity (J/cm²) |
|---|---|---|---|---|
| Uninfected/Untreated | 1 (2) | L6, R4 | N/A | N/A |
| Infected/Untreated | 2 (2) | R6, R7 | *Staphylococcus aureus* ATCC BAA 1768 | N/A |
| Infected/Photofrin - 1 h treatment | 3 (3) | L1, R1, R2 | *Staphylococcus aureus* ATCC BAA 1768 | 200 |
| Infected/Photofrin - 2 h treatment | 4 (3) | L2, L3, R3 | *Staphylococcus aureus* ATCC BAA 1768 | 200 |
| Infected/Photofrin - 4 h treatment | 5 (3) | L4, L5, R5 | *Staphylococcus aureus* ATCC BAA 1768 | 200 |

Figure 7A:
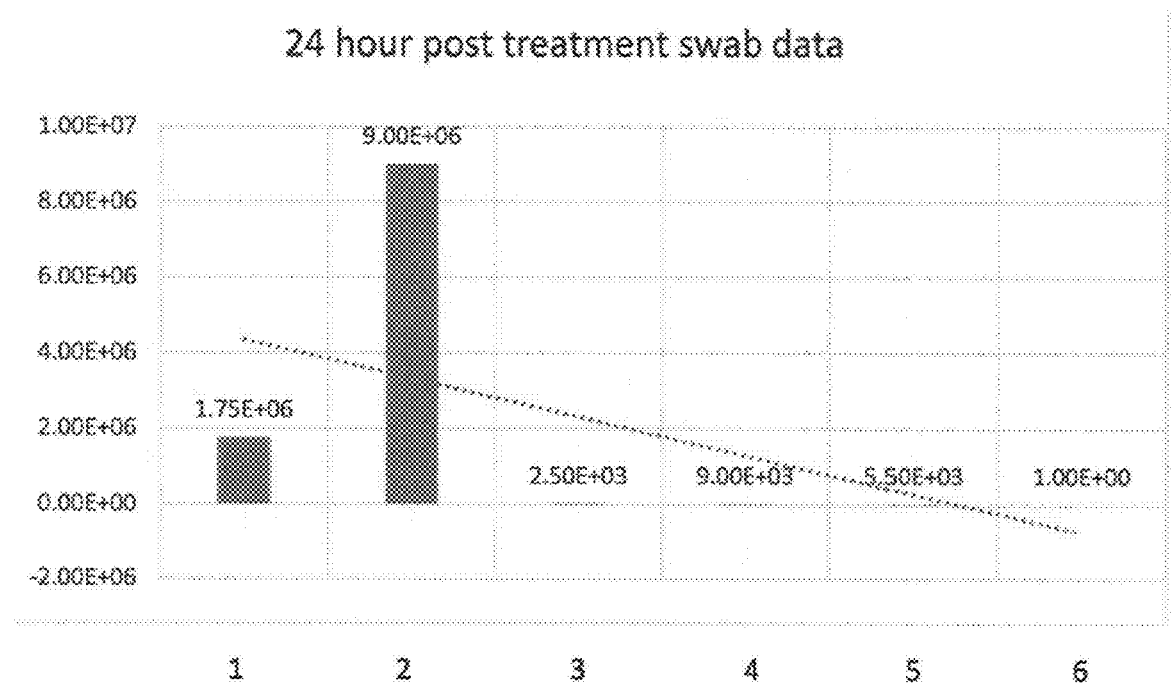
FIG. 7A shows Log CFU counts from swab samples taken 24 hours post aPDT in treated samples compared to uninfected untreated controls described in Example 8. Treatment consisted of 1-hour or 4-hour incubation with the test article followed by exposure to 630 nm light at a total dose of 200 J/cm$^2$. Columns 1 & 2 represent the infected untreated control wounds; 3 & 4 are data from wounds which had undergone 1 hour of incubation followed by light exposure; 5 &6 shows the data from wounds incubated for 4-hours followed by light exposure. The trend line indicates the general course or tendency showing a decrease in bacterial survival based upon incubation time with the test article.
Figure 7B:
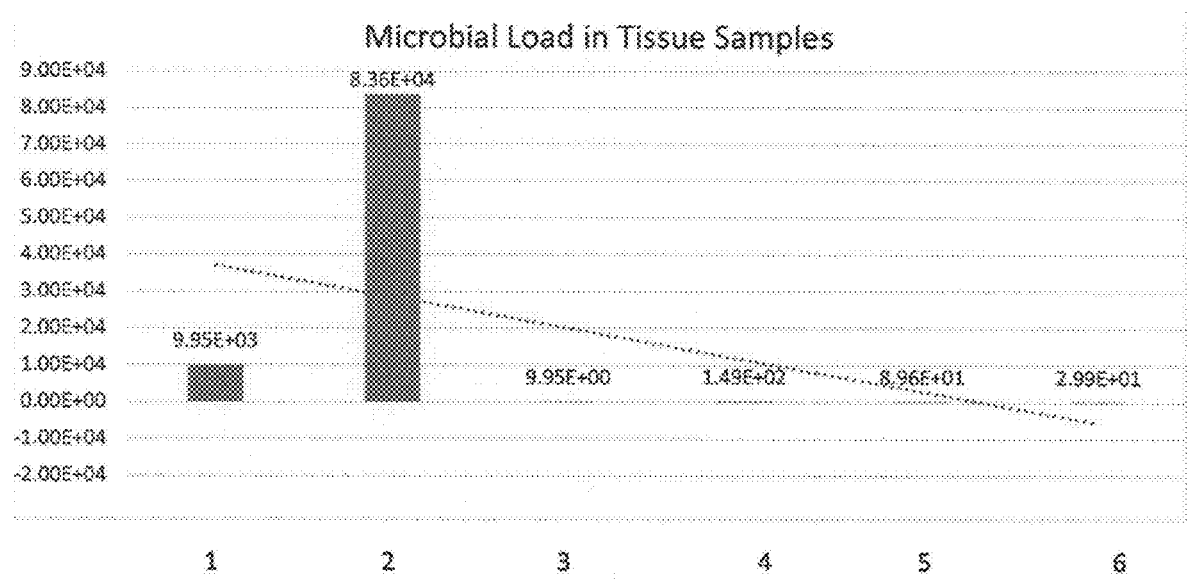
FIG. 7B shows Log CFU counts from tissue biopsy samples taken 24 hours post a PDT in treated samples compared to uninfected untreated controls described in Example 8. Treatment consisted of 1-hour or 4-hour incubation with the test article followed by exposure to 630 nm light at a total dose of 200 J/cm$^2$. Columns 1 & 2 represent the infected untreated control wounds; 3 & 4 are data from wounds which had undergone 1 hour of incubation followed by light exposure; 5 & 6 shows the data from wounds incubated for 4-hours followed by light exposure. The trend line indicates the general course or tendency showing a decrease in bacterial survival based upon incubation time with the test article.

Results:

FIG. 7A depicts $\log_{10}$ CFU counts from swab samples taken 24 hours post aPDT in treated samples compared to uninfected untreated controls. FIG. 7B depicts $\log_{10}$ CFU counts from tissue biopsy samples taken 24 hours post a PDT in treated samples compared to uninfected untreated controls.

Figure 8:
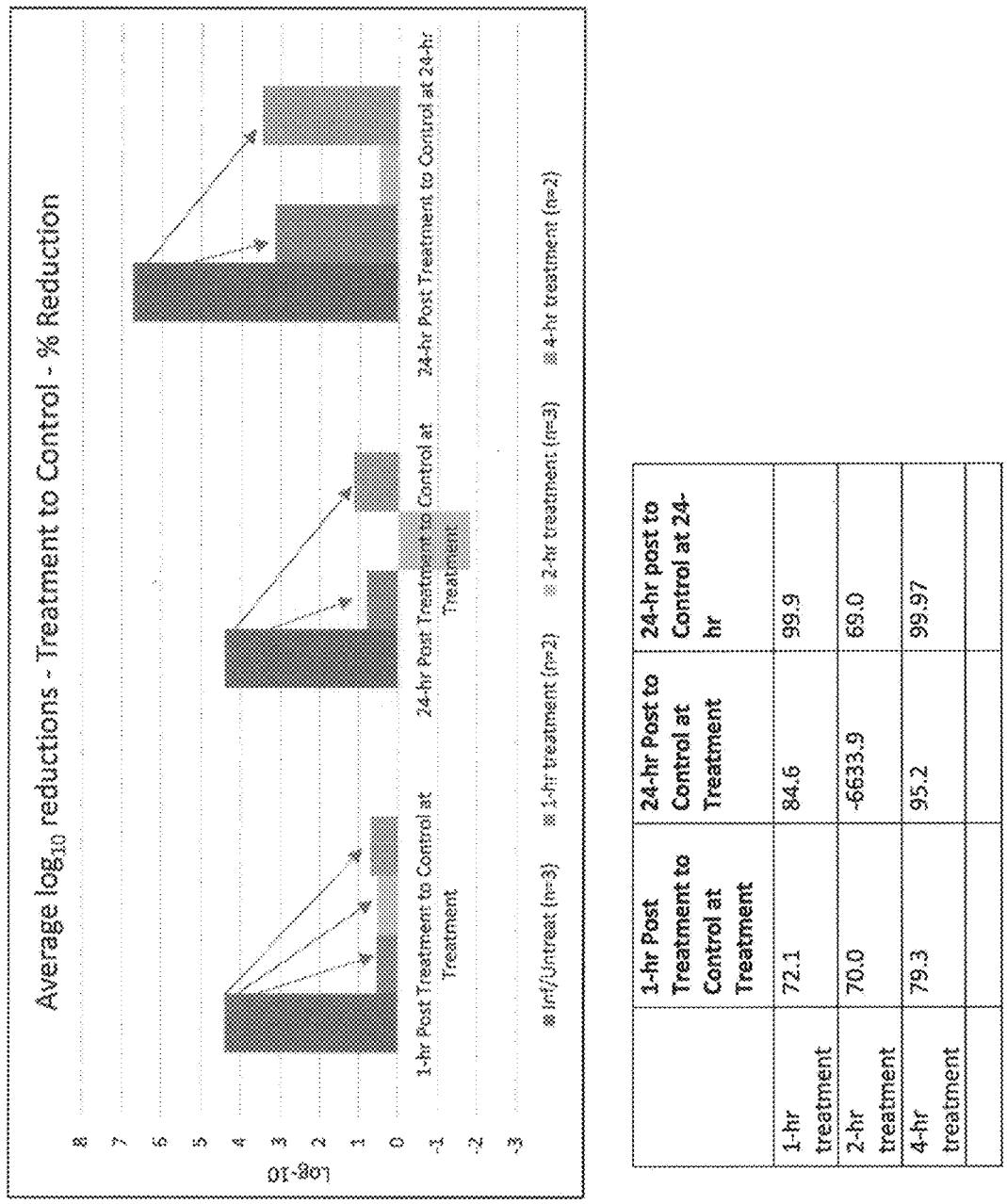
FIG. 8 shows the average Log 10 CFU reductions comparing Control wounds to treated wounds in each group presented as percentages.

FIG. 8 depicts $\log_{10}$ CFU counts from tissue biopsy samples taken 24 hours post a PDT in treated samples compared to uninfected untreated controls. The trend line indicates the general course or tendency showing a decrease in bacterial survival based upon incubation time with the test article.

Table 11 shows the mean microbial loads for swab and tissue samples for each group. Comparison of the microbial load difference in the individual 24 hr treated wounds with that of the untreated wounds revealed that two of the three individual 24 hr post-treatment wounds from Groups 3 and 5 had a 2.78 to >3.73 log 10 reduction in microbial loads in the swabs and corresponding reductions of 2.50 to 3.67 log 10 in the tissues compared to the mean of the untreated control (Table 10.2-3). The individual lesions in Groups 3&5 which did not show a log 10 reduction were those determined to be significant outliers. One of the three Group 4, 24 hr treatment swabs had a 1.73 log reduction in microbial load relative to the untreated control; however, the reduction was not observed in the corresponding tissue specimen.

TABLE 11

Mean Microbial Loads of Wound Specimens

| Specimen | Group 1 | | Group 2 | | Group 3 | | Group 4 | | Group 5 | |
|---|---|---|---|---|---|---|---|---|---|---|
| | Mean | SEM | Mean | SEM | Mean | SEM | Mean | SEM | Mean | SEM |
| Pretreat (swab) | 0.00E+00 | 0.00E+00 | 2.48E+04 | 1.03E+04 | 1.28E+04 | 4.75E+03 | 9.00E+03 | 3.33E+03 | 1.93E+04 | 4.78E+03 |
| 1 hr (swab) | N/A | N/A | N/A | N/A | 8.78E+03 | 1.72E+03 | 7.43E+03 | 7.36E+02 | 7.48E+03 | 2.89E+02 |
| 24 hr (swab) | 0.00E+00 | 0.00E+00 | 5.38E+06 | 3.63E+06 | 5.75E+03 | 3.20E+03 | 1.67E+06 | 9.40E+05 | 2.75E+03 | 2.75E+03 |
| 24 hr Tissue | 0.00E+00 | 0.00E+00 | 4.68E+04 | 3.68E+04 | 7.90E+01 | 6.95E+01 | 7.96E+04 | 2.71E+04 | 5.90E+01 | 2.90E+01 |

Data for swab specimens are expressed as CFU/Swab normalized to 1 ml of PBS. Data for Tissues are CFU/mm2 of surface area for one 8 mm biopsy plug.

Each of the treatment Groups revealed a decrease in microbial load as revealed by swab less than that of the control infected Group 2.

Accordingly, treatment with Formulation 3 following MRSA infection resulted in microbial load reductions of 99.9%, and 99.97% for Formulation 3 left for 1 h and 4 h before irradiation. Given the mixed efficacy results of the initial in-vivo studies where porfimer sodium was mixed with saline, nasal gel, and polyethelyne glocal, formulation 3 study efficacy results exceeding 99% bacteria kill rates are surprising and unexpected.

In sum, there was an overall reduction in the mean microbial loads in the 24 hr swabs and tissue samples in all treatment groups relative to the untreated group and an overall reduction in the mean microbial loads of the 1 hr and 4 hr treatment groups 24 hours after infection relative to the untreated control Group 2. Two of the three wounds in the 1 hr (Group 3) and 4 hr (Group 5) treatment groups displayed a reduction greater than 2.5 $\log_{10}$ in the microbial loads in both the 24 hr wound swabs and tissue specimens, relative to the untreated infected control wounds. One of the three Group 4 24 hr treatment swabs had a 1.73 $\log_{10}$ reduction in the microbial load relative to the untreated control. However, the reduction was not observed in the corresponding tissue specimen.

These results indicate that formulated porfimer sodium of the present invention such as formulation Formulation 3, is an effective treatment to reduce the microbial colonization of MRSA in a partial wound infection.

Example 9: Topical Porfimer Sodium Formulations 7A-7C with or without KI

Sodium porfimer formulations 7A-7C with or without KI were prepared according to Table 12 below.

TABLE 12

Topical Porfimer Sodium Formulations with varying amounts of porfimer sodium with or without KI.

| Components | Function | 7A | 7B | 7C | 7D | 7E | 7F |
|---|---|---|---|---|---|---|---|
| | | | | % w/w | | | |
| porfimer sodium | API | 0.1 | 0.2 | 0.5 | 0.1 | 0.2 | 0.5 |
| Potassium Iodide | | | | | 1.66* | 1.66* | 1.66* |
| Propylene glycol | Solvent | 45-49 | 45-49 | 45-49 | 45-49 | 45-49 | 45-49 |
| Penetration Enhancer | Penetration Enhancement | 30 | 30 | 30 | 30 | 30 | 30 |
| Polysorbate 80 | Surfactant | 2.0 | 2.0 | 2.0 | 2.0 | 2.0 | 2.0 |
| Glycerin | Humectant | 15 | 15 | 15 | 15 | 15 | 15 |
| Benzyl alcohol | Preservative | 2.0 | 2.0 | 2.0 | 2.0 | 2.0 | 2.0 |
| Phenoxyethanol | Antioxidant | 1.0 | 1.0 | 1.0 | 1.0 | 1.0 | 1.0 |
| Hexylene glycol | Solvent | 1.0 | 1.0 | 1.0 | 1.0 | 1.0 | 1.0 |
| Hydroxy propyl Cellulose | Gelling agent | 1.0 | 1.0 | 1.0 | 1.0 | 1.0 | 1.0 |
| Additional Excipients | Inactive agent or other filling agent | Add to obtain total w of 100 | Add to obtain total w of 100 | Add to obtain total w of 100 | Add to obtain total w of 100 | Add to obtain total w of 100 | Add to obtain total w of 100 |
| Total | | 100 | 100 | 100 | 100 | 100 | 100 |

*100 mM KI => 1.66% w/w

Example 10: Stability Studies on Porfimer Sodium Formulations 7A-7F

Stability studies for porfimer sodium formulations 7A, 7B, and 7C (0.1, 0.2, 0.5% w/w) without KI and porfimer sodium formulations 7D, 7E, and 7F (0.1, 0.2, 0.5% w/w) with KI (100 mM) were conducted.

Environmental Chambers are maintained at the following condition temperature (° C.) and relative humidity (RH): Long term storage: 25±2° C./60±5% RH. Refrigerated: 5±3° C. Accelerated storage: 40±2° C./75±5% RH Each formulation prototype was tested for physical and chemical stability. Physical testing typically includes appearance (visual description and color, of the product), pH and microscopy. Chemical testing includes, assay (% Label Claim) and impurities.

Results

The Stability test results for porfimer sodium formulations 7A-7F stored at 25° C./60% RH, 40° C./75% RH and 5° C. at 2 weeks and 1 month are depicted in FIGS. 11-16. As shown in FIGS. 11-16 the assay values for all samples at two and four weeks is within approximately 93-105% label claim of sodium porfimer.

Example 11: In Vivo Evaluation of the Ability of Porfimer Sodium Gel Formulations with or without 100 mM KI to Reduce/Eliminate Microbial Colonization in a Partial Thickness Wound Healing Model This study evaluated the ability of three different concentrations of porfimer sodium (0.1%, 0.2%, and 0.5%) in a gel formulation with (Formulations 7A-C) or without 100 mM KI (Formulations 7D-F) to reduce/eliminate microbial colonization from surgical sites in a partial thickness wound healing model.

The study was conducted in a 4 female Yorkshire pigs over the course of 4 days. A Dermatome was used to create partial thickness wounds of approximately 2.0 cm×2.0 cm in width and length with a depth of 0.5 mm parallel to the spine of the animal with one row of five (5) wounds along the each side of the animal for the test article treatment group animals and or one row of eight (8) and a second row of seven (7) wounds along the opposite sides of the control group animal.

Designated wounds on each of the animals were infected with methicillin-resistant *Staphylococcus aureus* (MRSA- ATCC 1768) following wound creation. Three (3) wounds on the control group animal were designated as uninfected controls and were not inoculated. The wounds were bandaged, and bacterial colonization was allowed to develop overnight. Designated infected wounds in the test article treatment groups were subjected to a single course of treatment. Treatments consisted of application of the test article followed by an incubation period of 30 minutes then photoactivation at 200 J/cm$^2$ for 20 minutes. Designated infected wounds in the control group received application of the test article but were not subjected to photoactivation. Microbial load was determined from wound swabs taken just prior to treatment, one hour and 24 hours following treatment and tissue biopsies harvested at 24 hours after treatment. Experiments were conducted under dim light (less than 200 lux). The treatment Groups are summarized in Table 13 below.

treatment swabs. Analysis of 24-hour post-treatment swabs revealed an overall increase in the group mean □CFU for all control and treatment groups.

Evaluation of microbial load in tissue specimens harvested 24 hours after treatment revealed a dose-dependent reduction in the relative microbial load in the porfimer sodium treated wounds, with the largest relative reductions in the 0.5% PS formulations 7C and 7F (FIGS. 18A and B). This reduction was further enhanced by the presence of 100 mM KI in the lower porfimer sodium concentration formulations of 0.1% (formulation 7D) and 0.2% (formulation 7E). One way ANOVA analysis revealed statistically significant reductions in the tissue microbial loads between the wounds treated with Porfimer sodium 0.1% and porfimer sodium 0.2%+100 mM KI (formulation 7D and 7E) (p=0.027), Porfimer sodium 0.5% (formulation 7C)

TABLE 13

Treatment Groups

| Treatment | Group | Animal | Number of lesions | Bacteria (10$^6$ to 10$^7$ CFU/wound) | Vol. (cc's) formulation/ group* | Light intensity (J/cm$^2$) |
|---|---|---|---|---|---|---|
| Uninfected/ Untreated | 1 | 54567 (67) | 3 | N/A | 0 | N/A |
| Infected/ Untreated | 2 | 54567 (67) | 3 | S. aureus ATCC BAA 1768 | 0 | N/A |
| Infected/ Placebo no PS + KI | 2a | 54567 (67) | 3 | S. aureus ATCC BAA 1768 | 3 | N/A |
| Infected/ Placebo no PS no KI | 2b | 54567 (67) | 3 | S. aureus ATCC BAA 1768 | 3 | N/A |
| Infected/ Placebo + PS no KI | 2c | 54567 (67) | 3 | S. aureus ATCC BAA 1768 | 3 | N/A |
| Infected/ Formulation 7C | 3 | 54569 (69) | 5 | S. aureus ATCC BAA 1768 | 5 | 200 |
| Infected/ Formulation 7F | 3 | 54569 (69) | 5 | S. aureus ATCC BAA 1768 | 5 | 200 |
| Infected/ Formulation 7A | 4 | 54570 (70) | 5 | S. aureus ATCC BAA 1768 | 5 | 200 |
| Infected/ Formulation 7D | 4 | 54570 (70) | 5 | S. aureus ATCC BAA 1768 | 5 | 200 |
| Infected/ Formulation 7B | 5 | 54565 (65) | 5 | S. aureus ATCC BAA 1768 | 5 | 200 |
| Infected/ Formulation 7E | 5 | 54565 (65) | 5 | S. aureus ATCC BAA 1768 | 5 | 200 |

*The concentration of PS (porfimer sodium) in the placebo groups was 0.2%

Figure 17:
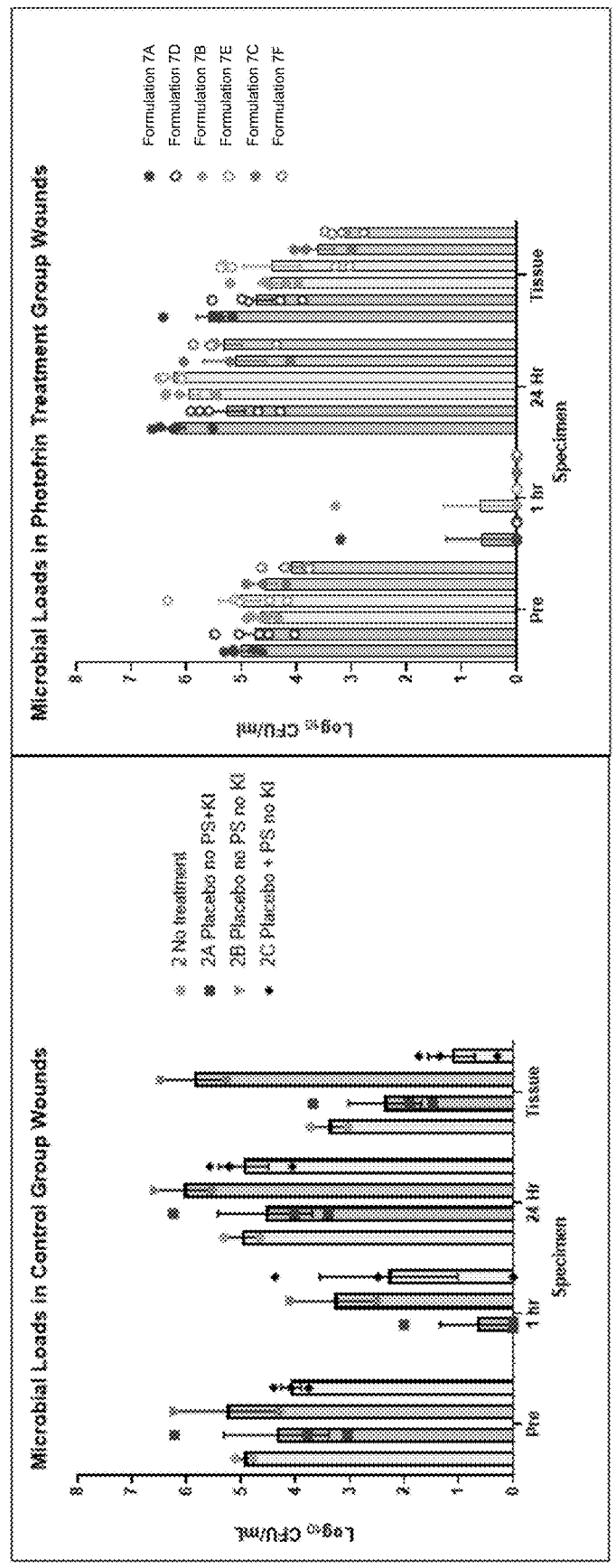
FIG. 17 shows microbial loads in control and porfimer sodium treated wounds
Figure 18:
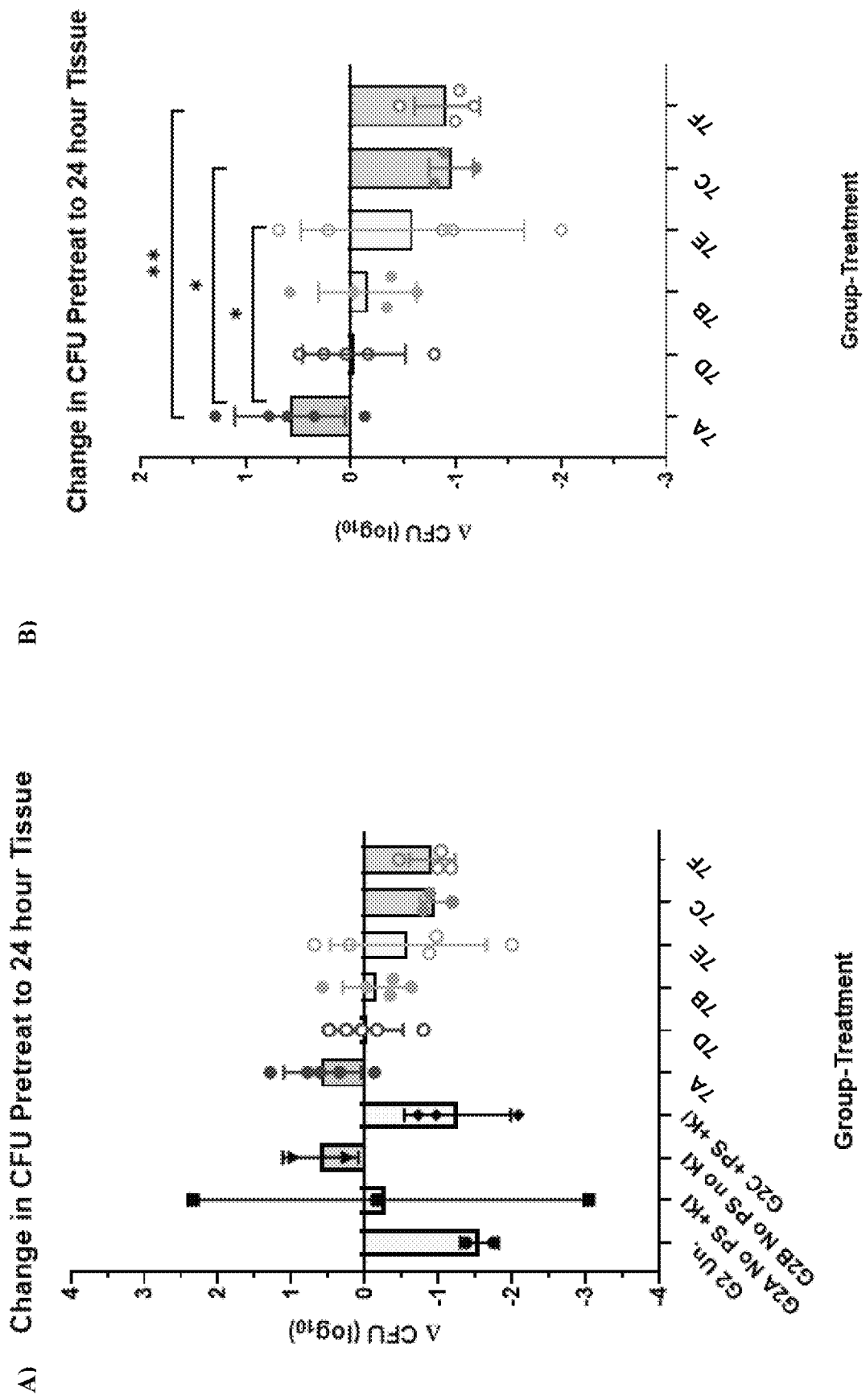
FIG. 18A) shows change in microbial loads in controls and porfimer sodium treated wounds at 24-hour post-treatment B) shows change in microbial loads in porfimer sodium treated wounds at 24-hour post-treatment. One way ANOVA analysis *$\rho$<0.05, **$\rho$<0.01.

Results:

Microbial load values for control group wounds are presented graphically in FIG. 17. As shown in FIG. 17, there was an overall reduction in the mean microbial loads in the 1 hr swabs in all treatment groups relative to the untreated group with the microbial load in the majority of treated wounds reaching undetectable levels. The percentage of 1-hour swabs from the treated wounds that had undetectable microbial loads correlated with the concentration of porfimer sodium and the presence of 100 mM KI in the formulation. Porfimer sodium formulations containing 0.5% PS and 100 mM KI (formulation 7F) or Porfimer sodium 0.5% alone (formulation 7C) reduced the microbial loads to undetectable in 100% of the treated wounds. Undetectable levels were seen in 80% and 60% of the 1-hour post treatment swabs in wounds treated with porfimer sodium 0.2% or 0.1% alone (formulations 7B and 7A), respectively. In contrast, only three of eight wounds (37.5%) had undetectable levels of bacteria in the placebo treated groups 2A Placebo No PS+KI (2 of 3), 2B Placebo No PS No KI (0 of 2), and 2C Placebo+PS No KI (1 of 3) in the 1 hour post (p=0.011), and porfimer sodium 0.5% HPC+100 mM KI (p=0.0066) (formula 7F) (FIG. 18 B).

Example 12: Study to Assess the Potential Duration and Intensity of Dermal Reaction in Subjects Receiving Topical Administration of a Formulation for the Delivery of Porfimer Sodium with and without Potassium Iodide This study was designed to assess skin irritation in healthy volunteers following a single topical application of a gel formulation containing porfimer sodium with or without potassium iodide, in variation.

Study Groups

Figure 19:
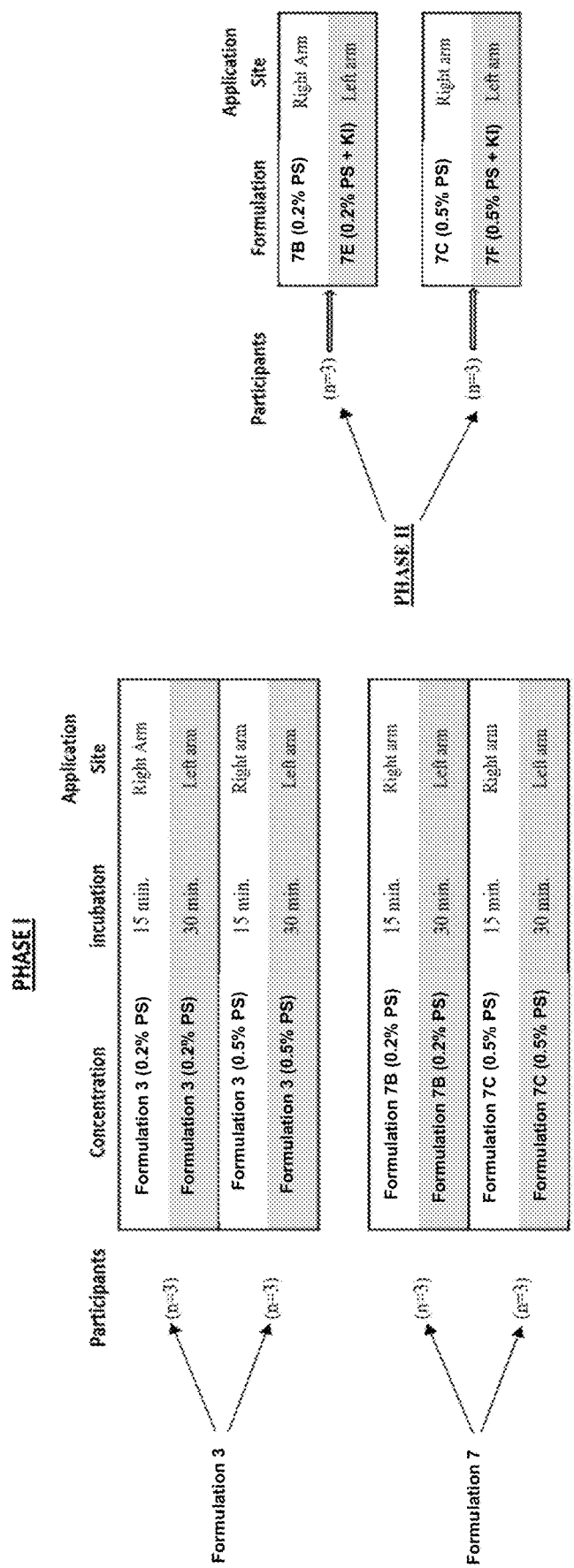
FIG. 19 depicts the design of the study described in Example 12

As shown in FIG. 19, in the first set of subjects, two of the variations used were the application of formulation 3 with 2 concentrations of the drug porfimer sodium (0.2% and 0.5%). In the second set of subjects, two of the variations used were a second gel formulation with 2 different concentrations of the drug porfimer sodium 0.2% (formulation 7B) and 0.5% (formulation 7C). In the third set of subjects, two of the variations employed were formulations with porfimer sodium 0.2%+100 mM Potassium Iodide (formulation 7E) and porfimer sodium (0.5%)+100 mM Potassium Iodide (formulation 7F). The study assessed skin irritation after the application of the formulations, an incubation period of either 15 or 30 minutes, followed by light irradiation of 630 nm of approximately 50 J/cm$^2$.

Procedures/Methods

The photosensitivity procedure was conducted, generally, on the inside of each forearm. The adhesive backed exposure cuff was placed on the skin avoiding, to the extent possible, any cuts, bruises, lesions, freckles, moles or scars. After placing a disposable dose patch a marker was used to identify the coordinates, for future follow-up cuff placement. The formulation was applied to an opening on the cuff and incubated for 30 minutes. Each of the areas was exposed to a light dose (50 J/cm2; approximately 5-minutes). Any sensation that was felt and verbalized by the test subject, was recorded. After the exposure was complete, the areas which had received the topical formulation were wiped with a saline soaked gauze to clean off any remaining or excess formulation. Photo documentation and recording of any visible reaction to the treated area was completed. The data collected consisted of the subject's skin coloration based on an erythema scale and photographic documentation. A visual Analog Scale was be used to collect any information regarding pain associated with the study. Patients skin response and level and duration of symptoms, if any, were recorded immediately following procedure, 48 hours post, 1-week post and 2 weeks post procedure.

Results:

There was no report of pain, edema, or pruritis (itch) across all 72 lesions.

Erythema was reported. Pre-treatment, no erythematous lesions were noted for any of the 72 treatment sites in the entire sample. There were also no reports of erythema at 48 h, 1 week, or 2 weeks post treatment. All observed erythema was immediate post-exposure only (i.e. transient) (see Tables 14-17) and not accompanied with discomfort (itch or pain). As shown in Table 14, in all groups no ratings above 2 (pink) were noted and, when reported, the most common report was slightly pink (61%). The present disclosure thus provides a method for treating a wound without the adverse side effects commonly known in the art.

TABLE 14

Post-treatment Erythema: Immediate all groups

|  | Frequency | Percent | Valid Percent | Cumulative Percent |
|---|---|---|---|---|
| none | 20 | 27.8 | 27.8 | 27.8 |
| 1 | 44 | 61.1 | 61.1 | 88.9 |
| 2 | 8 | 11.1 | 11.1 | 100.0 |
| Total | 72 | 100.0 | 100.0 |  |

0 = no lesion,
1 = slightly pink,
2 = pink,
3 = red and
4 = dark red or purple

TABLE 15

Number of exposed sites in Group 1 that developed erythema post treatment:

| # of Sites Treated | Formulation | Incubation | Level of Erythema 0 pre tx | Level of Erythema 0 post tx | Level of Erythema 1 post tx | Level of Erythema 2 post tx | 48 h post erythema |
|---|---|---|---|---|---|---|---|
| 6 | 3 0.2% PS | 15 m | 6 | 5 | 1 | 0 | 0 |
| 6 | 3 0.2% PS | 30 m | 6 | 4 | 2 | 0 | 0 |
| 6 | 3-0.5% PS | 15 m | 6 | 0 | 5 | 1 | 0 |
| 6 | 3 0.5% PS | 30 m | 6 | 4 | 2 | 0 | 0 |

Erythema Scale: 0 = no color; 1 = slightly pink; 2 = pink; 3 = red; 4 = dark red or purple

TABLE 16

Number of exposed sites in Group 2 that developed erythema post treatment:

| # of Sites Treated | Formulation | Incubation | Level of Erythema 0 pre-tx | Level of Erythema 0 post tx | Level of Erythema 1 post tx | Level of Erythema 2 post tx | 48 h post erythema |
|---|---|---|---|---|---|---|---|
| 6 | 7A 0.2% PS | 15 m | 6 | 1 | 5 | 0 | 0 |
| 6 | 7A 0.2% | 30 m | 6 | 3 | 3 | 0 | 0 |
| 6 | 7C 0.5% | 15 m | 6 | 1 | 5 | 0 | 0 |
| 6 | 7C 0.5% | 30 m | 6 | 0 | 4 | 2 | 0 |

Erythema Scale: 0 = no color; 1 = slightly pink; 2 = pink; 3 = red; 4 = dark red or purple

TABLE 17

Number of exposed sites in Groups 3 & 4 that developed erythema post treatment:

| # of Sites Treated | Formulation | Incubation | Level of Erythema 0 pre-tx | Level of Erythema 0 post-tx | Level of Erythema 1 post-tx | Level of Erythema 2 post-tx | 48 h post erythema |
|---|---|---|---|---|---|---|---|
| 6 | 7B-0.2% | 15 m | 6 | 0 | 5 | 1 | 0 |
| 6 | 7E 0.2% + KI | 30 m | 6 | 0 | 6 | 0 | 0 |
| 6 | 7C-0.5% | 15 m | 6 | 0 | 3 | 3 | 0 |
| 6 | 7F 0.5% + KI | 30 m | 6 | 1 | 4 | 1 | 0 |

Example 13: Study to Assess the Porfimer Sodium with or without Potassium Iodide with or without DMSO to Reduce/Eliminate Microbial Colonization and Biofilms in Partial Thickness Wounds Sodium porfimer formulations 8A-8B with or without KI were prepared according to Table 18 below.

TABLE 18

Topical Porfimer Sodium Formulations with porfimer sodium with or without KI or DMSO

| Components | Function | 8A | 8B | 8C | 8D |
|---|---|---|---|---|---|
| | | % w/w | | | |
| Porfimer sodium | API | 0.5 | 0.5 | 0.5 | 0.5 |
| Potassium Iodide | | — | 1.66 | — | 1.66 |
| Propylene glycol | Solvent | 40-50 | 40-50 | 30-40 | 30-40 |
| DMSO | Permeation enhancer | 0.0 | 0.0 | 5-20 | 5-20 |
| Penetration Enhancer | Penetration Enhancement | 30 | 30 | 30 | 30 |
| Polysorbate 80 | Surfactant | 2.0 | 2.0 | 2.0 | 2.0 |
| Glycerin | Humectant | 15 | 15 | 15 | 15 |
| Benzyl alcohol | Preservative | 2.0 | 2.0 | 2.0 | 2.0 |
| Phenoxyethanol | Antioxidant | 1.0 | 1.0 | 1.0 | 1.0 |
| Hexylene glycol | Solvent | 1.0 | 1.0 | 1.0 | 1.0 |
| Hydroxy propyl Cellulose | Gelling agent | 1.0 | 1.0 | 1.0 | 1.0 |
| Additional Excipients | Inactive agent or other filling agent | Add to obtain total w of 100 | Add to obtain total w of 100 | Add to obtain total w of 100 | Add to obtain total w of 100 |
| Total | | 100 | 100 | 100 | 100 |

*100 mM KI => 1.66% w/w

Partial thickness wounds were created parallel to the spine of pig subjects for a total of 28 partial thickness wounds all of were infected with *S. aureus* ATCC BAA 1768 and the untreated or treated in a different treatment group as provided below in Table 19.

TABLE 19

Treatment Groups for Partial Thickness Wounds in Pig Study Groups

| Treatment | Group | Animal | Number of lesions | Bacteria ($10^6$ to $10^7$ CFU/wound) | Vol. (cc's) formulation/group* | Light intensity ($J/cm^2$) |
|---|---|---|---|---|---|---|
| Infected/ Untreated | 1 | 1 | 2 | S. aureus ATCC BAA 1768 | 0 | N/A |
| Infected/ Formulation 8A | 2 | 1 | 3 | S. aureus ATCC BAA 1768 | 0 | 200 |
| Infected/ Formulation 8B | 3 | 1 | 3 | S. aureus ATCC BAA 1768 | 3 | 200 |
| Infected/ Formulation 8C | 4 | 1 | 3 | S. aureus ATCC BAA 1768 | 3 | 200 |
| Infected/ Formulation 8D | 5 | 1 | 3 | S. aureus ATCC BAA 1768 | 3 | 200 |
| Infected/ Formulation8A/ 2 day | 2a | 2 | 3 | S. aureus ATCC BAA 1768 | 5 | 200 |
| Infected/ Formulation 8B/ 2 day | 3a | 2 | 3 | S. aureus ATCC BAA 1768 | 5 | 200 |
| Infected/ Formulation8C/ 2 day | 4a | 2 | 3 | S. aureus ATCC BAA 1768 | 5 | 200 |

TABLE 19-continued

Treatment Groups for Partial Thickness Wounds in Pig Study Groups

| Treatment | Group | Animal | Number of lesions | Bacteria ($10^6$ to $10^7$ CFU/wound) | Vol. (cc's) formulation/ group* | Light intensity ($J/cm^2$) |
|---|---|---|---|---|---|---|
| Infected/ Formulation 8D/ 2 day | 5a | 2 | 3 | S. aureus ATCC BAA 1768 | 5 | 200 |
| Infected/Untreated | 6 | 2 | 2 | S. aureus ATCC BAA 1768 | 0 | N/A |

One hundred microliters (100 μL) of freshly cultured *Staphylococcus aureus* (ATCC BAA 1768) at a concentration of $10^7$ to $10^8$ CFU/mL were spotted into the center of each wound in all wounds using a sterile pipet. The bacterial inoculum was lightly scrubbed into the test site for 10 seconds using a sterile spatula (maintaining care to limit the exposure to the wound and not exposing the normal skin adjacent to the wound with the infectious agent) and allowed to dry for 3 minutes. The procedures of the study is further provided below in Table 20.

TABLE 20

Schedule of Procedures

| Study Day (dates) | Event | | Detail |
|---|---|---|---|
| Day −1 (24 Aug. 2021) | Surgery/ Administration of bacteria | Animals 1 and 2 | 14 partial thickness wounds up to 2.0 cm × 2.0 cm each, incised on each animal. Bacteria instilled into all wounds on both animals. |
| Day 0 (25 Aug. 2021) | Treatment | Experiments to be conducted under dim light (less than 200 lux) | Pre-treatment swab of all wounds for CFU Apply test article formulation to all Treatment Groups. No Test article (formulation) is to be applied to group 1 animal 1 or group 6 animal 2. Incubate drug for 30 minutes followed by 16 min and 40 sec exposure with 200 $J/cm^2$ light. Obtain swabs of each of the treated wound for bacterial load estimate at 1 h post light treatment. Obtain swabs from group 1 and group 6 wounds at 1 hour post pre-treatment swab for bacterial load estimate. |
| Day 1 (26 Aug. 2021) | Course #2 Treatment Animal 2 | Animal 2 Formulation application and experiments to be conducted under dim light (less than 200 lux) | Obtain 24-hour post-treatment swabs for all lesions on animal 2. Apply formulation to lesions in groups 2a, 3a, 4a, and 5a. Incubate for 30 min. In order, treat all lesions with 200 $J/cm^2$ of light, with the exception of group 6. Obtain swabs of each of the treated wound for bacterial load estimate at 1 h post light treatment. |

TABLE 20-continued

Schedule of Procedures

| Study Day (dates) | Event | Detail | |
|---|---|---|---|
| Day 1 (26 Aug. 2021) | Tissue collection for biopsy and microbial load in Animal 1. | Procedures to be conducted under dim light (less than 200 lux) | Euthanize Swab of all wounds for CFU Harvest wound tissues - ½ for histology, ½ for CFU) |
| Day 2 (27 Aug. 2021) | Tissue collection for biopsy and microbial load in Animal 2. | Procedures to be conducted under dim light (less than 200 lux) | Euthanize Swab of all wounds for CFU Harvest wound tissues - ½ for histology, ½ for CFU) |

The respective Photofrin formulation (8A-8D) was applied to the wound bed and incubated for times as indicated in Table 20. The formulation was then activated in each wound following application using lens fiber optic attached to a 630-nm emitting laser with wounds in groups 2-5 in animal 1 and 2a-5a in animal 2 subjected to 200 J/cm$^2$ (approximately between 20 to 25 minutes). The wounds were then swabbed at 1 hour post treatment and will then be rebandaged and wrapped.

24 hours following the treatment as in Table 20, the animals were euthanized and the bandages were removed and the wounds swabbed for determination of microbial load. Wound tissues were harvested with one half of the harvested tissue placed into 10% formalin for histology and the other half placed into a pre-weighed culture tube containing sterile PBS for determination of microbial load.

Wounds were treated, surgical sites were examined, and bandages were changed on the days of treatment indicated in Table 20. All procedures were performed under ABSL-2 conditions. On each day of the of treatment (Study Day 0, and 1), the outer bandaging was removed using sterile scissors and the bandages were removed using sterile forceps. Prior to treatment, each wound was swabbed using a sterile cotton tipped applicator in a serpentine motion starting at the upper left hand margin of the wound (relative to the spine) and ending at the bottom right wound margin. The swabs were placed into a sterile culture tube containing 1 to 2 mL of sterile PBS for determination of microbial load.

For determination of microbial load, the tubes containing PBS and wound from Days 1, and 2 were vortexed and serial dilutions of the eluted bacteria were prepared in sterile PBS and plated onto Oxacillin Screen Agar (Mueller Hinton Agar with 6 µg/mL Oxacillin and 4% NaCl) in duplicate. Colonies on the plates were enumerated following incubation at 37° C. and the bacterial load was reported as colonies forming units per milliliter of wound fluid (CFU/mL).

The tubes containing the Day 1 and 2 tissue specimens were weighed to determined tissue mass. Wound tissues were homogenized and serial dilutions of the homogenates were prepared in PBS and plated onto Oxacillin Screen Agar in duplicate. Colonies on the plates will be enumerated following incubation at 37° C. and the bacterial load will be reported as colonies forming units per milligram of wound tissue (CFU/mg).

Microbial titer data from each group are provided in Tables 21 and 22 below

TABLE 21

Microbial Titer Data Points 2 Day Treatment Groups
Microbial Titers

| | | Day 0 | | Day 1 | | Day 2 | |
|---|---|---|---|---|---|---|---|
| Group # | Wound # | Pre-treat | Post-treat | Pre-treat | Post-treat | 48 hr swab | Tissue/cm2 |
| 6 | L7 | 8566667 | NA | 705000 | N/A | 113000 | 265625 |
| 6 | RI | 87000 | NA | 33000 | N/A | 1115000 | 21094 |
| 2a | LI | 270000 | 5500 | 150000 | 100 | 2180000 | 523438 |
| 2a | L5 | 50000 | <1000 | 146500 | <100 | 232500 | 93750 |
| 2a | R4 | 1900000 | <1000 | 125000 | <100 | 1090000 | 84375 |
| 3a | L2 | 7800000 | <1000 | 685000 | <100 | 59000 | 482813 |
| 3a | L6 | 360000 | <1000 | 100000 | 33000 | 2000 | 1563 |
| 3a | R5 | 4690000 | <1000 | 1480000 | 2000 | 1295000 | 1068750 |
| 4a | L3 | 950000 | <1000 | 13000 | 1500 | 500 | 531250 |
| 4a | R2 | 760000 | <1000 | 620000 | <100 | 154500 | 667188 |
| 4a | R6 | 400000 | <1000 | 79000 | <100 | 42000 | 8438 |
| 5a | L4 | 170000 | <1000 | 325000 | <100 | 132000 | 592188 |
| 5a | R3 | 3490000 | <1000 | 950000 | <100 | 158500 | 109375 |
| 5a | R7 | N/A | <1000 | 420000 | <100 | 11000 | 250000 |

TABLE 22

Microbial Titer Data Points 1 Day Treatment Groups
Microbial Titers

| | | Day 0 | | Day 1 | |
|---|---|---|---|---|---|
| Group# | Wound # | Pre-treat | Post-treat | 24 hr swab | Tissue/cm2 |
| 1 | L7 | 25000 | N/A | 150000 | 335938 |
| 1 | R1 | 650000 | N/A | 635000 | 264063 |
| 2 | L1 | 10000 | <100 | 430000 | 129688 |
| 2 | L5 | 10000 | <100 | 13500 | 3281 |
| 2 | R4 | 300000 | <100 | 7500000 | 24375 |
| 3 | L2 | 730000 | <100 | 930000 | 329688 |
| 3 | L6 | 60000 | <100 | 410000 | 60938 |
| 3 | R5 | 150000 | <100 | 1840000 | 59375 |
| 4 | L3 | 30000 | <100 | 7500 | 42188 |
| 4 | R2 | 1550000 | <100 | 2000 | 232813 |
| 4 | R6 | 800000 | <100 | 100000 | 15625 |
| 5 | L4 | 10000 | <100 | 117000 | 26719 |
| 5 | R3 | 1200000 | <100 | 10200000 | 271875 |
| 5 | R7 | 600000 | <100 | 1205000 | 8508 |

The mean microbial titers are also provided for the 2 day and 1 day treatments groups in Table 23 and Table 24 below.

TABLE 23

Mean Microbial Titer Data of 2 Day Treatment Groups
Mean Microbial Titers

| Group# | Wound # | Day 0 Pre-treat | Day 0 Post-treat | Day 1 Pre-treat | Day 1 Post-treat | Day 2 48 hr swab | Day 2 Tissue/cm2 |
|---|---|---|---|---|---|---|---|
| 1 | Infected/untreated | 4326833 | N/A | 369000 | N/A | 614000 | 143359 |
| 2a | Infected/Formulation 8A | 740000 | 5500 | 140500 | 100 | 1167500 | 233854 |
| 3a | Infected/Formulation 8B | 4283333 | <1000 | 755000 | 17500 | 452000 | 517708 |
| 4a | Infected/Formulation 8C | 703333 | <1000 | 237333 | 1500 | 65667 | 402292 |
| 5a | Infected/Formulation 8D | 1830000 | <1000 | 565000 | <100 | 100500 | 317188 |

TABLE 24

Mean Microbial Titer Data of 1 Day Treatment Groups
Mean Microbial Titers

| Group# | Wound # | Day 0 Pre-treat | Day 0 Post-treat | Day 1 Pre-treat | Tissue/cm2 |
|---|---|---|---|---|---|
| 1 | Infected/untreated | 337500 | N/A | 392500 | 300000 |
| 2 | Infected/Formulation 8A | 106667 | <100 | 2647833 | 52448 |
| 3 | Infected/Formulation 8B | 313333 | <100 | 1060000 | 150000 |
| 4 | Formulation 8C | 793333 | <100 | 36500 | 96875 |
| 5 | Infected/Formulation 8D | 603333 | <100 | 3840667 | 102367 |

The results show that both formulation 8C and 8D have significant antimicrobial effect (1 day and 2 day treatment) when compared to the control with no treatment of formulation.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:

1. A topical pharmaceutical composition comprising porfimer sodium, one or more gelling agents, one or more permeation enhancers, polysorbate 80, glycerin, benzyl alcohol, phenoxyethanol, and hexylene glycol, and wherein the gelling agent is hydroxy propyl cellulose.

2. The topical pharmaceutical composition of claim 1, wherein the porfimer sodium ranges from about 0.1% to about 1.0% w/w in the pharmaceutical composition.

3. The topical pharmaceutical composition of claim 2, wherein porfimer sodium is about 0.5% w/w.

4. The topical pharmaceutical composition of claim 1, wherein the one or more permeation enhancers ranges about 0.5% to about 50% w/w in the pharmaceutical composition.

5. The topical pharmaceutical composition of claim 1, wherein the one or more permeation enhancers is about 0.5% to about 50% w/w, the polysorbate 80 is about 1% to about 3% w/w, glycerin is about 10% to about 20% w/w, benzyl alcohol is about 1% to about 3% w/w, phenoxyethanol is about 0.5% to about 2% w/w, hexylene glycol is about 0.5% to about 2% w/w, and hydroxy propyl cellulose is about 0.5% to about 2% w/w in the pharmaceutical composition.

6. The topical pharmaceutical composition of claim 5, wherein the composition additionally comprises potassium iodide (KI).

7. The topical pharmaceutical composition of claim 6, wherein the KI is about 1% w/w to about 2% w/w in the pharmaceutical composition.

8. The topical pharmaceutical composition of claim 3, wherein the composition comprises one or more permeation enhancers selected from the group consisting of propylene glycol, polyethylene glycol 400 SR, polyethylene glycol 300 LA, diethylene glycol monoethyl ether, DMSO, and Polysorbate 80 SR.

9. The topical pharmaceutical composition of claim 8, wherein the permeation enhancer comprises DMSO and the DMSO ranges about 10% w/w to about 40% w/w in the pharmaceutical composition.

10. The topical pharmaceutical composition of claim 9, wherein the DMSO is about 40% w/w in the pharmaceutical composition.

11. A method for treating an infected area, comprising administering to a subject in need thereof the topical pharmaceutical composition of claim 1, wherein the pharmaceutical composition is applied to the infected area; and light at about 630 nm in wavelength is applied to the infected area.

12. The method of claim 11, wherein the infected area is due to a microbial infection.

13. The method of claim 12, wherein the infected area is infected with *Staphylococcus aureus*(+), *Staphylococcus aureus* MRSA(+), *Peptostreptococcus anaerobius*(+), *Proprionibacterium acnes*(+), *Bacillus thuringiensis*(+), *Bacillus atrophaeus*(+), *Streptococcus mutans*(+), *Streptococcus pneumoniae*(+), *Prevotella*(−), *Porphyromonas gingivalis* (−), *Salmonella enterica*(−), *Escherichia coli*(−), *Yersinia intermedia*(−), *Acinetobacter baumannii*(−), *Neisseria gon-* orrhea(−), *Haemophilus influenza*(−), *Fusobacterium nucleatum*(−), *Moraxella catarrhalis*(−), *Candida albicans, Candida glabrata, Candida parasilosis, Candida krusei, Candida tropicalis,* or *Candida guilliermondi.*

14. The method of claim 11, wherein the porfimer sodium ranges from about 0.1% to about 1.0% w/w in the pharmaceutical composition.

15. The method of claim 11, wherein the one or more permeation enhancers ranges about 0.5% w/w to about 50% w/w, the polysorbate 80 is about 1% to about 3% w/w, glycerin is about 10% to about 20% w/w, benzyl alcohol is about 1% to about 3% w/w, phenoxyethanol is about 0.5% to about 2% w/w, hexylene glycol is about 0.5% to about 2% w/w, and hydroxy propyl cellulose is about 0.5% to about 2% w/w in the pharmaceutical composition.

16. The method of claim 15, wherein the pharmaceutical composition additionally comprises potassium iodide (KI), and the KI is about 1% w/w to about 2% w/w in the pharmaceutical composition.

17. The method of claim 15, wherein the pharmaceutical composition comprises DMSO, and the DMSO is at about 10% w/w to about 40% w/w in the pharmaceutical composition.

18. The method of claim 17, wherein the DMSO is about 40% w/w in the pharmaceutical composition.

* * * * *